(12) United States Patent
Boudreaux et al.

(10) Patent No.: US 8,414,577 B2
(45) Date of Patent: *Apr. 9, 2013

(54) SURGICAL INSTRUMENTS AND COMPONENTS FOR USE IN STERILE ENVIRONMENTS

(75) Inventors: Chad P. Boudreaux, Cincinnati, OH (US); Frederick E. Shelton, IV, Hillsboro, OH (US); Bret W. Smith, Kings Mills, OH (US); Daniel J. Abbott, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 596 days.

This patent is subject to a terminal disclaimer.

(21) Appl. No.: 12/621,732

(22) Filed: Nov. 19, 2009

(65) Prior Publication Data

US 2010/0198220 A1 Aug. 5, 2010

Related U.S. Application Data

(63) Continuation-in-part of application No. 12/366,548, filed on Feb. 5, 2009.

(51) Int. Cl.
*A61B 18/18* (2006.01)
(52) U.S. Cl.
USPC ............................................. 606/41; 606/34
(58) Field of Classification Search .............. 600/133, 600/172, 122, 112; 606/34, 41
See application file for complete search history.

(56) References Cited

U.S. PATENT DOCUMENTS

| 66,052 A | 6/1867 | Smith |
| 662,587 A | 11/1900 | Blake |
| 951,393 A | 3/1910 | Hahn |
| 2,037,727 A | 4/1936 | La Chapelle |
| 2,132,295 A | 10/1938 | Hawkins |
| 2,161,632 A | 6/1939 | Nattenheimer |

(Continued)

FOREIGN PATENT DOCUMENTS

| CA | 2458946 A1 | 3/2003 |
| CA | 2512960 A1 | 1/2006 |

(Continued)

OTHER PUBLICATIONS

U.S. Appl. No. 12/032,024, filed Feb. 15, 2008.

(Continued)

*Primary Examiner* — Linda Dvorak
*Assistant Examiner* — Jocelyn D Ram

(57) ABSTRACT

A surgical instrument comprises a first portion encapsulated by a membrane and a second portion comprising a surgical instrument body and a cavity in the surgical instrument body. The cavity is configured to receive the first portion. The second portion comprises a first region comprising an opening in communication with the cavity, and a closure member movable between a first position and a second position. The closure member is in sealable engagement with the second region when it is in the first position and is at least partially free from sealable engagement with the second region when it is in the second position. One or more electrical contacts on the first portion or the second portion are configured to penetrate the membrane to allow a connection to be made between the first portion and the second portion when the closure member moves from the second position into the first position.

10 Claims, 61 Drawing Sheets

U.S. PATENT DOCUMENTS

| | | |
|---|---|---|
| 2,211,117 A | 8/1940 | Hess |
| 2,214,870 A | 9/1940 | West |
| 2,441,096 A | 5/1948 | Happe |
| 2,526,902 A | 10/1950 | Rublee |
| 2,674,149 A | 4/1954 | Benson |
| 2,804,848 A | 9/1957 | O'Farrell et al. |
| 2,808,482 A | 10/1957 | Zanichkowsky et al. |
| 2,853,074 A | 9/1958 | Olson |
| 3,032,769 A | 5/1962 | Palmer |
| 3,075,062 A | 1/1963 | Iaccarino |
| 3,078,465 A | 2/1963 | Bobrov |
| 3,166,072 A | 1/1965 | Sullivan, Jr. |
| 3,266,494 A | 8/1966 | Brownrigg et al. |
| 3,269,630 A | 8/1966 | Fleischer |
| 3,357,296 A | 12/1967 | Lefever |
| 3,490,675 A | 1/1970 | Green et al. |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| RE28,932 E | 8/1976 | Noiles et al. |
| 4,060,089 A | 11/1977 | Noiles |
| 4,129,059 A | 12/1978 | Van Eck |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,408,692 A | 10/1983 | Siegel et al. |
| 4,415,112 A | 11/1983 | Green |
| 4,428,376 A | 1/1984 | Mericle |
| 4,429,695 A | 2/1984 | Green |
| 4,434,796 A | 3/1984 | Karapetian et al. |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,890,613 A | 1/1990 | Golden et al. |
| 4,892,244 A | 1/1990 | Fox et al. |
| 4,915,100 A | 4/1990 | Green |
| 4,930,503 A | 6/1990 | Pruitt |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |

| | | | | | |
|---|---|---|---|---|---|
| 5,084,057 A | 1/1992 | Green et al. | 5,342,396 A | 8/1994 | Cook |
| 5,088,979 A | 2/1992 | Filipi et al. | 5,344,060 A | 9/1994 | Gravener et al. |
| 5,088,997 A | 2/1992 | Delahuerga et al. | 5,350,400 A | 9/1994 | Esposito et al. |
| 5,094,247 A | 3/1992 | Hernandez et al. | 5,352,235 A | 10/1994 | Koros et al. |
| 5,100,420 A | 3/1992 | Green et al. | 5,352,238 A | 10/1994 | Green et al. |
| 5,104,025 A | 4/1992 | Main et al. | 5,354,303 A | 10/1994 | Spaeth et al. |
| 5,106,008 A | 4/1992 | Tompkins et al. | 5,356,006 A | 10/1994 | Alpern et al. |
| 5,111,987 A | 5/1992 | Moeinzadeh et al. | 5,358,510 A | 10/1994 | Luscombe et al. |
| 5,116,349 A | 5/1992 | Aranyi | 5,359,231 A | 10/1994 | Flowers et al. |
| 5,129,570 A | 7/1992 | Schulze et al. | D352,780 S | 11/1994 | Glaeser et al. |
| 5,137,198 A | 8/1992 | Nobis et al. | 5,360,428 A | 11/1994 | Hutchinson, Jr. |
| 5,139,513 A | 8/1992 | Segato | 5,364,003 A | 11/1994 | Williamson, IV |
| 5,141,144 A | 8/1992 | Foslien et al. | 5,366,134 A | 11/1994 | Green et al. |
| 5,156,315 A | 10/1992 | Green et al. | 5,366,479 A | 11/1994 | McGarry et al. |
| 5,156,614 A | 10/1992 | Green et al. | 5,370,645 A | 12/1994 | Klicek et al. |
| 5,158,567 A | 10/1992 | Green | 5,372,596 A | 12/1994 | Klicek et al. |
| D330,699 S | 11/1992 | Gill | 5,372,602 A | 12/1994 | Burke |
| 5,163,598 A | 11/1992 | Peters et al. | 5,374,277 A | 12/1994 | Hassler |
| 5,171,247 A | 12/1992 | Hughett et al. | 5,379,933 A | 1/1995 | Green et al. |
| 5,171,249 A | 12/1992 | Stefanchik et al. | 5,381,782 A | 1/1995 | DeLaRama et al. |
| 5,188,111 A | 2/1993 | Yates et al. | 5,382,247 A | 1/1995 | Cimino et al. |
| 5,190,517 A | 3/1993 | Zieve et al. | 5,383,880 A | 1/1995 | Hooven |
| 5,195,968 A | 3/1993 | Lundquist et al. | 5,383,881 A | 1/1995 | Green et al. |
| 5,197,648 A | 3/1993 | Gingold | 5,383,888 A | 1/1995 | Zvenyatsky et al. |
| 5,200,280 A | 4/1993 | Karasa | 5,383,895 A | 1/1995 | Holmes et al. |
| 5,205,459 A | 4/1993 | Brinkerhoff et al. | 5,389,098 A | 2/1995 | Tsuruta et al. |
| 5,207,697 A | 5/1993 | Carusillo et al. | 5,391,180 A | 2/1995 | Tovey et al. |
| 5,209,747 A | 5/1993 | Knoepfler | 5,392,979 A | 2/1995 | Green et al. |
| 5,211,649 A | 5/1993 | Kohler et al. | 5,395,030 A | 3/1995 | Kuramoto et al. |
| 5,217,457 A | 6/1993 | Delahuerga et al. | 5,395,033 A | 3/1995 | Byrne et al. |
| 5,217,478 A | 6/1993 | Rexroth | 5,395,312 A | 3/1995 | Desai |
| 5,219,111 A | 6/1993 | Bilotti et al. | 5,397,046 A | 3/1995 | Savage et al. |
| 5,221,036 A | 6/1993 | Takase | 5,397,324 A | 3/1995 | Carroll et al. |
| 5,221,281 A | 6/1993 | Klicek | 5,403,312 A | 4/1995 | Yates et al. |
| 5,222,963 A | 6/1993 | Brinkerhoff et al. | 5,405,072 A | 4/1995 | Zlock et al. |
| 5,222,975 A | 6/1993 | Crainich | 5,405,344 A | 4/1995 | Williamson et al. |
| 5,222,976 A | 6/1993 | Yoon | 5,407,293 A | 4/1995 | Crainich |
| 5,223,675 A | 6/1993 | Taft | 5,409,498 A | 4/1995 | Braddock et al. |
| 5,234,447 A | 8/1993 | Kaster et al. | 5,411,508 A | 5/1995 | Bessler et al. |
| 5,236,440 A | 8/1993 | Hlavacek | 5,413,267 A | 5/1995 | Solyntjes et al. |
| 5,239,981 A | 8/1993 | Anapliotis | 5,413,268 A | 5/1995 | Green et al. |
| 5,240,163 A | 8/1993 | Stein et al. | 5,413,272 A | 5/1995 | Green et al. |
| 5,242,457 A | 9/1993 | Akopov et al. | 5,415,334 A | 5/1995 | Williamson, IV et al. |
| 5,244,462 A | 9/1993 | Delahuerga et al. | 5,415,335 A | 5/1995 | Knodell, Jr. |
| 5,246,156 A | 9/1993 | Rothfuss et al. | 5,417,361 A | 5/1995 | Williamson, IV |
| 5,246,443 A | 9/1993 | Mai | 5,421,829 A | 6/1995 | Olichney et al. |
| 5,253,793 A | 10/1993 | Green et al. | 5,422,567 A | 6/1995 | Matsunaga |
| 5,258,009 A | 11/1993 | Conners | 5,423,809 A | 6/1995 | Klicek |
| 5,258,012 A | 11/1993 | Luscombe et al. | 5,425,745 A | 6/1995 | Green et al. |
| 5,259,366 A | 11/1993 | Reydel et al. | 5,431,322 A | 7/1995 | Green et al. |
| 5,260,637 A | 11/1993 | Pizzi | 5,431,668 A | 7/1995 | Burbank, III et al. |
| 5,263,629 A | 11/1993 | Trumbull et al. | 5,433,721 A | 7/1995 | Hooven et al. |
| 5,263,973 A | 11/1993 | Cook | 5,438,302 A | 8/1995 | Goble |
| 5,268,622 A | 12/1993 | Philipp | 5,441,193 A | 8/1995 | Gravener |
| 5,271,543 A | 12/1993 | Grant et al. | 5,441,494 A | 8/1995 | Ortiz |
| 5,271,544 A | 12/1993 | Fox et al. | 5,445,304 A | 8/1995 | Plyley et al. |
| RE34,519 E | 1/1994 | Fox et al. | 5,445,644 A | 8/1995 | Pietrafitta et al. |
| 5,275,323 A | 1/1994 | Schulze et al. | 5,447,417 A | 9/1995 | Kuhl et al. |
| 5,275,608 A | 1/1994 | Forman et al. | 5,447,513 A | 9/1995 | Davison et al. |
| 5,281,216 A | 1/1994 | Klicek | 5,449,355 A | 9/1995 | Rhum et al. |
| 5,282,806 A | 2/1994 | Haber et al. | 5,449,365 A | 9/1995 | Green et al. |
| 5,282,829 A | 2/1994 | Hermes | 5,452,836 A | 9/1995 | Huitema et al. |
| 5,297,714 A | 3/1994 | Kramer | 5,452,837 A | 9/1995 | Williamson, IV et al. |
| 5,304,204 A | 4/1994 | Bregen | 5,454,827 A | 10/1995 | Aust et al. |
| 5,307,976 A | 5/1994 | Olson et al. | 5,456,401 A | 10/1995 | Green et al. |
| 5,309,927 A | 5/1994 | Welch | 5,458,579 A | 10/1995 | Chodorow et al. |
| 5,312,023 A | 5/1994 | Green et al. | 5,462,215 A | 10/1995 | Viola et al. |
| 5,312,329 A | 5/1994 | Beaty et al. | 5,464,300 A | 11/1995 | Crainich |
| 5,314,424 A | 5/1994 | Nicholas | 5,465,894 A | 11/1995 | Clark et al. |
| 5,318,221 A | 6/1994 | Green et al. | 5,465,895 A | 11/1995 | Knodel et al. |
| 5,330,502 A | 7/1994 | Hassler et al. | 5,465,896 A | 11/1995 | Allen et al. |
| 5,332,142 A | 7/1994 | Robinson et al. | 5,466,020 A | 11/1995 | Page et al. |
| 5,333,422 A | 8/1994 | Warren et al. | 5,467,911 A | 11/1995 | Tsuruta et al. |
| 5,334,183 A | 8/1994 | Wuchinich | 5,470,006 A | 11/1995 | Rodak |
| 5,336,232 A | 8/1994 | Green et al. | 5,470,007 A | 11/1995 | Plyley et al. |
| 5,339,799 A | 8/1994 | Kami et al. | 5,472,132 A | 12/1995 | Savage et al. |
| 5,341,724 A | 8/1994 | Vatel | 5,472,442 A | 12/1995 | Klicek |
| 5,341,810 A * | 8/1994 | Dardel .................. 600/461 | 5,473,204 A | 12/1995 | Temple |
| 5,342,395 A | 8/1994 | Jarrett et al. | 5,474,057 A | 12/1995 | Makower et al. |

| Patent No. | Date | Inventor |
|---|---|---|
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,571,090 A | 11/1996 | Sherts |
| 5,571,100 A | 11/1996 | Goble et al. |
| 5,571,116 A | 11/1996 | Bolanos et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,611,709 A | 3/1997 | McAnulty |
| 5,613,966 A | 3/1997 | Makower et al. |
| 5,618,294 A | 4/1997 | Aust et al. |
| 5,618,303 A | 4/1997 | Marlow et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |

| | | | | | |
|---|---|---|---|---|---|
| 5,695,504 A | 12/1997 | Gifford, III et al. | 5,810,855 A | 9/1998 | Rayburn et al. |
| 5,695,524 A | 12/1997 | Kelley et al. | 5,813,813 A | 9/1998 | Daum et al. |
| 5,697,543 A | 12/1997 | Burdorff | 5,814,057 A | 9/1998 | Oi et al. |
| 5,697,943 A | 12/1997 | Sauer et al. | 5,817,084 A | 10/1998 | Jensen |
| 5,700,270 A | 12/1997 | Peyser et al. | 5,817,091 A | 10/1998 | Nardella et al. |
| 5,702,387 A | 12/1997 | Arts et al. | 5,817,093 A | 10/1998 | Williamson, IV et al. |
| 5,702,408 A | 12/1997 | Wales et al. | 5,817,109 A | 10/1998 | McGarry et al. |
| 5,702,409 A | 12/1997 | Rayburn et al. | 5,817,119 A | 10/1998 | Klieman et al. |
| 5,704,087 A | 1/1998 | Strub | 5,820,009 A | 10/1998 | Melling et al. |
| 5,704,534 A | 1/1998 | Huitema et al. | 5,823,066 A | 10/1998 | Huitema et al. |
| 5,706,997 A | 1/1998 | Green et al. | 5,826,776 A | 10/1998 | Schulze et al. |
| 5,706,998 A | 1/1998 | Plyley et al. | 5,827,271 A | 10/1998 | Buysse et al. |
| 5,707,392 A | 1/1998 | Kortenbach | 5,829,662 A | 11/1998 | Allen et al. |
| 5,709,334 A | 1/1998 | Sorrentino et al. | 5,833,690 A | 11/1998 | Yates et al. |
| 5,709,680 A | 1/1998 | Yates et al. | 5,833,695 A | 11/1998 | Yoon |
| 5,711,472 A | 1/1998 | Bryan | 5,833,696 A | 11/1998 | Whitfield et al. |
| 5,713,128 A | 2/1998 | Schrenk et al. | 5,836,503 A | 11/1998 | Ehrenfels et al. |
| 5,713,505 A | 2/1998 | Huitema | 5,836,960 A | 11/1998 | Kolesa et al. |
| 5,713,895 A | 2/1998 | Lontine et al. | 5,839,639 A | 11/1998 | Sauer et al. |
| 5,715,987 A | 2/1998 | Kelley et al. | 5,843,132 A | 12/1998 | Ilvento |
| 5,715,988 A | 2/1998 | Palmer | 5,846,254 A | 12/1998 | Schulze et al. |
| 5,716,366 A | 2/1998 | Yates | 5,849,011 A | 12/1998 | Jones et al. |
| 5,718,359 A | 2/1998 | Palmer et al. | 5,855,311 A | 1/1999 | Hamblin et al. |
| 5,718,360 A | 2/1998 | Green et al. | 5,855,583 A | 1/1999 | Wang et al. |
| 5,718,548 A | 2/1998 | Cotellessa | 5,860,975 A | 1/1999 | Goble et al. |
| 5,720,744 A | 2/1998 | Eggleston et al. | 5,865,361 A | 2/1999 | Milliman et al. |
| D393,067 S | 3/1998 | Geary et al. | 5,868,760 A | 2/1999 | McGuckin, Jr. |
| 5,725,536 A | 3/1998 | Oberlin et al. | 5,871,135 A | 2/1999 | Williamson, IV et al. |
| 5,725,554 A | 3/1998 | Simon et al. | 5,873,885 A | 2/1999 | Weidenbenner |
| 5,728,121 A | 3/1998 | Bimbo et al. | 5,876,401 A | 3/1999 | Schulze et al. |
| 5,730,758 A | 3/1998 | Allgeyer | 5,878,193 A | 3/1999 | Wang et al. |
| 5,732,871 A | 3/1998 | Clark et al. | 5,878,937 A | 3/1999 | Green et al. |
| 5,732,872 A | 3/1998 | Bolduc et al. | 5,878,938 A | 3/1999 | Bittner et al. |
| 5,735,445 A | 4/1998 | Vidal et al. | 5,891,160 A | 4/1999 | Williamson, IV et al. |
| 5,735,848 A | 4/1998 | Yates et al. | 5,893,506 A | 4/1999 | Powell |
| 5,735,874 A | 4/1998 | Measamer et al. | 5,894,979 A | 4/1999 | Powell |
| 5,738,474 A | 4/1998 | Blewett | 5,897,562 A | 4/1999 | Bolanos et al. |
| 5,738,648 A | 4/1998 | Lands et al. | 5,899,914 A | 5/1999 | Zirps et al. |
| 5,743,456 A | 4/1998 | Jones et al. | 5,901,895 A | 5/1999 | Heaton et al. |
| 5,747,953 A | 5/1998 | Philipp | 5,902,312 A | 5/1999 | Frater et al. |
| 5,749,889 A | 5/1998 | Bacich et al. | 5,904,693 A | 5/1999 | Dicesare et al. |
| 5,749,893 A | 5/1998 | Vidal et al. | 5,906,625 A | 5/1999 | Bito et al. |
| 5,752,644 A | 5/1998 | Bolanos et al. | 5,908,402 A | 6/1999 | Blythe |
| 5,752,965 A | 5/1998 | Francis et al. | 5,908,427 A | 6/1999 | McKean et al. |
| 5,755,717 A | 5/1998 | Yates et al. | 5,911,353 A | 6/1999 | Bolanos et al. |
| 5,758,814 A | 6/1998 | Gallagher et al. | 5,915,616 A | 6/1999 | Viola et al. |
| 5,762,255 A | 6/1998 | Chrisman et al. | 5,918,791 A | 7/1999 | Sorrentino et al. |
| 5,762,256 A | 6/1998 | Mastri et al. | 5,919,198 A | 7/1999 | Graves, Jr. et al. |
| 5,766,188 A | 6/1998 | Igaki | 5,928,256 A | 7/1999 | Riza |
| 5,766,205 A | 6/1998 | Zvenyatsky et al. | 5,931,847 A | 8/1999 | Bittner et al. |
| 5,769,892 A | 6/1998 | Kingwell | 5,931,853 A | 8/1999 | McEwen et al. |
| 5,772,379 A | 6/1998 | Evensen | 5,937,951 A | 8/1999 | Izuchukwu et al. |
| 5,772,578 A | 6/1998 | Heimberger et al. | 5,938,667 A | 8/1999 | Peyser et al. |
| 5,772,659 A | 6/1998 | Becker et al. | 5,941,442 A | 8/1999 | Geiste et al. |
| 5,776,130 A | 7/1998 | Buysse et al. | 5,944,172 A | 8/1999 | Hannula |
| 5,779,130 A | 7/1998 | Alesi et al. | 5,944,715 A | 8/1999 | Goble et al. |
| 5,779,131 A | 7/1998 | Knodel et al. | 5,948,030 A | 9/1999 | Miller et al. |
| 5,779,132 A | 7/1998 | Knodel et al. | 5,951,552 A | 9/1999 | Long et al. |
| 5,782,396 A | 7/1998 | Mastri et al. | 5,951,574 A | 9/1999 | Stefanchik et al. |
| 5,782,397 A | 7/1998 | Koukline | 5,954,259 A | 9/1999 | Viola et al. |
| 5,782,749 A | 7/1998 | Riza | 5,964,774 A | 10/1999 | McKean et al. |
| 5,782,859 A | 7/1998 | Nicholas et al. | 5,971,916 A * | 10/1999 | Koren .......................... 600/122 |
| 5,784,934 A | 7/1998 | Izumisawa | 5,988,479 A | 11/1999 | Palmer |
| 5,785,232 A | 7/1998 | Vidal et al. | 6,003,517 A | 12/1999 | Sheffield et al. |
| 5,787,897 A | 8/1998 | Kieturakis | 6,004,319 A | 12/1999 | Goble et al. |
| 5,792,135 A | 8/1998 | Madhani et al. | 6,010,054 A | 1/2000 | Johnson et al. |
| 5,792,165 A | 8/1998 | Klieman et al. | 6,012,494 A | 1/2000 | Balazs |
| 5,794,834 A | 8/1998 | Hamblin et al. | 6,013,076 A | 1/2000 | Goble et al. |
| 5,796,188 A | 8/1998 | Bays | 6,015,406 A | 1/2000 | Goble et al. |
| 5,797,536 A | 8/1998 | Smith et al. | 6,017,322 A * | 1/2000 | Snoke et al. ................ 604/95.01 |
| 5,797,537 A | 8/1998 | Oberlin et al. | 6,017,356 A | 1/2000 | Frederick et al. |
| 5,797,538 A | 8/1998 | Heaton et al. | 6,022,352 A | 2/2000 | Vandewalle |
| 5,797,906 A | 8/1998 | Rhum et al. | 6,024,741 A | 2/2000 | Williamson, IV et al. |
| 5,797,959 A | 8/1998 | Castro et al. | 6,024,748 A | 2/2000 | Manzo et al. |
| 5,799,857 A | 9/1998 | Robertson et al. | 6,027,501 A | 2/2000 | Goble et al. |
| 5,807,378 A | 9/1998 | Jensen et al. | 6,032,849 A | 3/2000 | Mastri et al. |
| 5,807,393 A | 9/1998 | Williamson, IV et al. | 6,033,378 A | 3/2000 | Lundquist et al. |
| 5,809,441 A | 9/1998 | McKee | 6,033,399 A | 3/2000 | Gines |
| 5,810,811 A | 9/1998 | Yates et al. | 6,033,427 A | 3/2000 | Lee |

| | | | |
|---|---|---|---|
| 6,039,733 A | 3/2000 | Buysse et al. | |
| 6,039,734 A | 3/2000 | Goble | |
| 6,045,560 A | 4/2000 | McKean et al. | |
| 6,050,472 A | 4/2000 | Shibata | |
| 6,053,390 A | 4/2000 | Green et al. | |
| 6,056,746 A | 5/2000 | Goble et al. | |
| 6,063,097 A | 5/2000 | Oi et al. | |
| 6,063,098 A | 5/2000 | Houser et al. | |
| 6,068,627 A | 5/2000 | Orszulak et al. | |
| 6,071,233 A | 6/2000 | Ishikawa et al. | |
| 6,074,386 A | 6/2000 | Goble et al. | |
| 6,077,286 A | 6/2000 | Cuschieri et al. | |
| 6,079,606 A | 6/2000 | Milliman et al. | |
| 6,082,577 A | 7/2000 | Coates et al. | |
| 6,083,234 A | 7/2000 | Nicholas et al. | |
| 6,083,242 A | 7/2000 | Cook | |
| 6,086,600 A | 7/2000 | Kortenbach | |
| 6,090,106 A | 7/2000 | Goble et al. | |
| 6,093,186 A | 7/2000 | Goble | |
| 6,099,537 A | 8/2000 | Sugai et al. | |
| 6,099,551 A | 8/2000 | Gabbay | |
| 6,102,271 A | 8/2000 | Longo et al. | |
| 6,109,500 A | 8/2000 | Alli et al. | |
| 6,117,158 A | 9/2000 | Measamer et al. | |
| 6,119,913 A | 9/2000 | Adams et al. | |
| 6,120,433 A | 9/2000 | Mizuno et al. | |
| 6,123,241 A | 9/2000 | Walter et al. | |
| H1904 H | 10/2000 | Yates et al. | |
| 6,126,058 A | 10/2000 | Adams et al. | |
| 6,126,670 A | 10/2000 | Walker et al. | |
| 6,131,789 A | 10/2000 | Schulze et al. | |
| 6,132,368 A | 10/2000 | Cooper | |
| 6,139,546 A | 10/2000 | Koenig et al. | |
| 6,155,473 A | 12/2000 | Tompkins et al. | |
| 6,156,056 A | 12/2000 | Kearns et al. | |
| 6,159,146 A | 12/2000 | El Gazayerli | |
| 6,159,200 A | 12/2000 | Verdura et al. | |
| 6,162,208 A | 12/2000 | Hipps | |
| 6,165,175 A | 12/2000 | Wampler et al. | |
| 6,165,184 A * | 12/2000 | Verdura et al. | 606/148 |
| 6,168,605 B1 | 1/2001 | Measamer et al. | |
| 6,171,316 B1 | 1/2001 | Kovac et al. | |
| 6,171,330 B1 | 1/2001 | Benchetrit | |
| 6,174,308 B1 | 1/2001 | Goble et al. | |
| 6,174,309 B1 | 1/2001 | Wrublewski et al. | |
| 6,179,776 B1 | 1/2001 | Adams et al. | |
| 6,181,105 B1 | 1/2001 | Cutolo et al. | |
| 6,193,129 B1 | 2/2001 | Bittner et al. | |
| 6,197,042 B1 | 3/2001 | Ginn et al. | |
| 6,202,914 B1 | 3/2001 | Geiste et al. | |
| 6,214,028 B1 | 4/2001 | Yoon et al. | |
| 6,220,368 B1 | 4/2001 | Ark et al. | |
| 6,223,835 B1 | 5/2001 | Habedank et al. | |
| 6,228,081 B1 | 5/2001 | Goble | |
| 6,228,084 B1 | 5/2001 | Kirwan, Jr. | |
| 6,231,565 B1 | 5/2001 | Tovey et al. | |
| 6,234,178 B1 | 5/2001 | Goble et al. | |
| 6,241,139 B1 | 6/2001 | Milliman et al. | |
| 6,241,723 B1 | 6/2001 | Heim et al. | |
| 6,249,076 B1 | 6/2001 | Madden et al. | |
| 6,250,532 B1 | 6/2001 | Green et al. | |
| 6,258,107 B1 | 7/2001 | Balázs et al. | |
| 6,261,286 B1 | 7/2001 | Goble et al. | |
| 6,264,086 B1 | 7/2001 | McGuckin, Jr. | |
| 6,264,087 B1 | 7/2001 | Whitman | |
| 6,270,508 B1 | 8/2001 | Klieman et al. | |
| 6,273,897 B1 | 8/2001 | Dalessandro et al. | |
| 6,277,114 B1 | 8/2001 | Bullivant et al. | |
| 6,293,942 B1 | 9/2001 | Goble et al. | |
| 6,296,640 B1 | 10/2001 | Wampler et al. | |
| 6,302,311 B1 | 10/2001 | Adams et al. | |
| 6,306,134 B1 | 10/2001 | Goble et al. | |
| 6,309,403 B1 | 10/2001 | Minor et al. | |
| 6,315,184 B1 | 11/2001 | Whitman | |
| 6,320,123 B1 | 11/2001 | Reimers | |
| 6,324,339 B1 | 11/2001 | Hudson et al. | |
| 6,325,799 B1 | 12/2001 | Goble | |
| 6,325,810 B1 | 12/2001 | Hamilton et al. | |
| 6,330,965 B1 | 12/2001 | Milliman et al. | |
| 6,331,181 B1 | 12/2001 | Tierney et al. | |
| 6,331,761 B1 | 12/2001 | Kumar et al. | |
| 6,334,860 B1 | 1/2002 | Dorn | |
| 6,336,926 B1 | 1/2002 | Goble | |
| 6,346,077 B1 | 2/2002 | Taylor et al. | |
| 6,352,503 B1 | 3/2002 | Matsui et al. | |
| 6,358,224 B1 | 3/2002 | Tims et al. | |
| 6,364,877 B1 | 4/2002 | Goble et al. | |
| 6,364,888 B1 | 4/2002 | Niemeyer et al. | |
| 6,373,152 B1 | 4/2002 | Wang et al. | |
| 6,387,113 B1 | 5/2002 | Hawkins et al. | |
| 6,387,114 B2 | 5/2002 | Adams | |
| 6,391,038 B2 | 5/2002 | Vargas et al. | |
| 6,398,781 B1 | 6/2002 | Goble et al. | |
| 6,398,797 B2 | 6/2002 | Bombard et al. | |
| 6,406,440 B1 | 6/2002 | Stefanchik | |
| 6,409,724 B1 | 6/2002 | Penny et al. | |
| H2037 H | 7/2002 | Yates et al. | |
| 6,416,486 B1 | 7/2002 | Wampler | |
| 6,416,509 B1 | 7/2002 | Goble et al. | |
| RE37,814 E | 8/2002 | Allgeyer | |
| 6,436,097 B1 | 8/2002 | Nardella | |
| 6,436,107 B1 | 8/2002 | Wang et al. | |
| 6,436,122 B1 | 8/2002 | Frank et al. | |
| 6,439,446 B1 | 8/2002 | Perry et al. | |
| 6,440,146 B2 | 8/2002 | Nicholas et al. | |
| 6,443,973 B1 | 9/2002 | Whitman | |
| 6,450,391 B1 | 9/2002 | Kayan et al. | |
| 6,468,275 B1 | 10/2002 | Wampler et al. | |
| 6,471,106 B1 | 10/2002 | Reining | |
| 6,482,200 B2 | 11/2002 | Shippert | |
| 6,485,490 B2 | 11/2002 | Wampler et al. | |
| 6,488,196 B1 | 12/2002 | Fenton, Jr. | |
| 6,488,197 B1 | 12/2002 | Whitman | |
| 6,491,201 B1 | 12/2002 | Whitman | |
| 6,491,690 B1 | 12/2002 | Goble et al. | |
| 6,491,701 B2 | 12/2002 | Tierney et al. | |
| 6,492,785 B1 | 12/2002 | Kasten et al. | |
| 6,494,896 B1 | 12/2002 | D'Alessio et al. | |
| 6,503,257 B2 | 1/2003 | Grant et al. | |
| 6,503,259 B2 | 1/2003 | Huxel et al. | |
| 6,505,768 B2 | 1/2003 | Whitman | |
| 6,510,854 B2 | 1/2003 | Goble | |
| 6,511,468 B1 | 1/2003 | Cragg et al. | |
| 6,517,535 B2 | 2/2003 | Edwards | |
| 6,517,565 B1 | 2/2003 | Whitman et al. | |
| 6,517,566 B1 | 2/2003 | Hovland et al. | |
| 6,522,101 B2 | 2/2003 | Malackowski | |
| 6,543,456 B1 | 4/2003 | Freeman | |
| 6,547,786 B1 | 4/2003 | Goble | |
| 6,550,546 B2 | 4/2003 | Thurler et al. | |
| 6,551,333 B2 | 4/2003 | Kuhns et al. | |
| 6,554,861 B2 | 4/2003 | Knox et al. | |
| 6,558,379 B1 | 5/2003 | Batchelor et al. | |
| 6,565,560 B1 | 5/2003 | Goble et al. | |
| 6,569,085 B2 | 5/2003 | Kortenbach et al. | |
| 6,569,171 B2 | 5/2003 | DeGuillebon et al. | |
| 6,578,751 B2 | 6/2003 | Hartwick | |
| 6,582,427 B1 | 6/2003 | Goble et al. | |
| 6,588,643 B2 | 7/2003 | Bolduc et al. | |
| 6,589,164 B1 * | 7/2003 | Flaherty | 600/121 |
| 6,592,597 B2 | 7/2003 | Grant et al. | |
| 6,596,432 B2 | 7/2003 | Kawakami et al. | |
| D478,665 S | 8/2003 | Isaacs et al. | |
| D478,986 S | 8/2003 | Johnston et al. | |
| 6,601,749 B2 | 8/2003 | Sullivan et al. | |
| 6,602,252 B2 | 8/2003 | Mollenauer | |
| 6,605,078 B2 | 8/2003 | Adams | |
| 6,605,669 B2 | 8/2003 | Awokola et al. | |
| 6,616,686 B2 | 9/2003 | Coleman et al. | |
| 6,619,529 B2 | 9/2003 | Green et al. | |
| 6,620,166 B1 | 9/2003 | Wenstrom, Jr. et al. | |
| 6,629,630 B2 | 10/2003 | Adams | |
| 6,629,974 B2 | 10/2003 | Penny et al. | |
| 6,629,988 B2 | 10/2003 | Weadock | |
| 6,636,412 B2 | 10/2003 | Smith | |
| 6,638,108 B2 | 10/2003 | Tachi | |
| 6,638,285 B2 | 10/2003 | Gabbay | |
| 6,644,532 B2 | 11/2003 | Green et al. | |

| Patent No. | Date | Inventor |
|---|---|---|
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,692,507 B2 | 2/2004 | Pugsley et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,821,284 B2 | 11/2004 | Sturtz et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,843,403 B2 | 1/2005 | Whitman |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,684 B2 | 8/2006 | McGuckin, Jr. et al. |
| 7,094,202 B2 | 8/2006 | Nobis et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |

| Patent | Type | Date | Inventor |
|---|---|---|---|
| 7,108,701 | B2 | 9/2006 | Evens et al. |
| 7,108,709 | B2 | 9/2006 | Cummins |
| 7,111,769 | B2 | 9/2006 | Wales et al. |
| 7,112,214 | B2 | 9/2006 | Peterson et al. |
| RE39,358 | E | 10/2006 | Goble |
| 7,114,642 | B2 | 10/2006 | Whitman |
| 7,118,582 | B1 | 10/2006 | Wang et al. |
| 7,121,446 | B2 | 10/2006 | Arad et al. |
| 7,122,028 | B2 | 10/2006 | Looper et al. |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,140,527 | B2 | 11/2006 | Ehrenfels et al. |
| 7,140,528 | B2 | 11/2006 | Shelton, IV |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,147,139 | B2 | 12/2006 | Schwemberger et al. |
| 7,147,637 | B2 | 12/2006 | Goble |
| 7,147,650 | B2 | 12/2006 | Lee |
| 7,150,748 | B2 | 12/2006 | Ebbutt et al. |
| 7,153,300 | B2 | 12/2006 | Goble |
| 7,156,863 | B2 | 1/2007 | Sonnenschein et al. |
| 7,159,750 | B2 | 1/2007 | Racenet et al. |
| 7,160,299 | B2 | 1/2007 | Baily |
| 7,161,036 | B2 | 1/2007 | Oikawa et al. |
| 7,168,604 | B2 | 1/2007 | Milliman et al. |
| 7,172,104 | B2 | 2/2007 | Scirica et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,188,758 | B2 | 3/2007 | Viola et al. |
| 7,195,627 | B2 | 3/2007 | Amoah et al. |
| 7,204,835 | B2 | 4/2007 | Latterell et al. |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,213,736 | B2 | 5/2007 | Wales et al. |
| 7,214,224 | B2 | 5/2007 | Goble |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,235,089 | B1 | 6/2007 | McGuckin, Jr. |
| 7,235,302 | B2 | 6/2007 | Jing et al. |
| 7,237,708 | B1 | 7/2007 | Guy et al. |
| 7,238,195 | B2 | 7/2007 | Viola |
| 7,241,288 | B2 | 7/2007 | Braun |
| 7,246,734 | B2 | 7/2007 | Shelton, IV |
| 7,247,161 | B2 | 7/2007 | Johnston et al. |
| 7,252,660 | B2 | 8/2007 | Kunz |
| 7,255,696 | B2 | 8/2007 | Goble et al. |
| 7,258,262 | B2 | 8/2007 | Mastri et al. |
| 7,260,431 | B2 | 8/2007 | Libbus et al. |
| 7,265,374 | B2 | 9/2007 | Lee et al. |
| 7,267,679 | B2 | 9/2007 | McGuckin, Jr. et al. |
| 7,273,483 | B2 | 9/2007 | Wiener et al. |
| 7,278,562 | B2 | 10/2007 | Mastri et al. |
| 7,278,563 | B1 | 10/2007 | Green |
| 7,278,994 | B2 | 10/2007 | Goble |
| 7,282,048 | B2 | 10/2007 | Goble et al. |
| 7,295,907 | B2 | 11/2007 | Lu et al. |
| 7,296,724 | B2 | 11/2007 | Green et al. |
| 7,297,149 | B2 | 11/2007 | Vitali et al. |
| 7,300,450 | B2 | 11/2007 | Vleugels et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,303,556 | B2 | 12/2007 | Metzger |
| 7,308,998 | B2 | 12/2007 | Mastri et al. |
| 7,324,572 | B2 | 1/2008 | Chang |
| 7,328,828 | B2 | 2/2008 | Ortiz et al. |
| 7,328,829 | B2 | 2/2008 | Arad et al. |
| 7,330,004 | B2 | 2/2008 | DeJonge et al. |
| 7,334,717 | B2 | 2/2008 | Rethy et al. |
| 7,336,184 | B2 | 2/2008 | Smith et al. |
| 7,338,513 | B2 | 3/2008 | Lee et al. |
| 7,343,920 | B2 | 3/2008 | Toby et al. |
| 7,348,763 | B1 | 3/2008 | Reinhart et al. |
| 7,351,258 | B2 | 4/2008 | Ricotta et al. |
| 7,354,447 | B2 | 4/2008 | Shelton, IV et al. |
| 7,357,287 | B2 | 4/2008 | Shelton, IV et al. |
| 7,364,060 | B2 | 4/2008 | Milliman |
| 7,364,061 | B2 | 4/2008 | Swayze et al. |
| 7,377,928 | B2 | 5/2008 | Zubik et al. |
| 7,380,695 | B2 | 6/2008 | Doll et al. |
| 7,380,696 | B2 | 6/2008 | Shelton, IV et al. |
| 7,388,217 | B2 | 6/2008 | Buschbeck et al. |
| 7,396,356 | B2 | 7/2008 | Mollenauer |
| 7,397,364 | B2 | 7/2008 | Govari |
| 7,398,907 | B2 | 7/2008 | Racenet et al. |
| 7,398,908 | B2 | 7/2008 | Holsten et al. |
| 7,404,508 | B2 | 7/2008 | Smith et al. |
| 7,404,509 | B2 | 7/2008 | Ortiz et al. |
| 7,407,075 | B2 | 8/2008 | Holsten et al. |
| 7,407,078 | B2 | 8/2008 | Shelton, IV et al. |
| 7,410,086 | B2 | 8/2008 | Ortiz et al. |
| 7,416,101 | B2 | 8/2008 | Shelton, IV et al. |
| 7,418,078 | B2 | 8/2008 | Blanz et al. |
| 7,419,080 | B2 | 9/2008 | Smith et al. |
| 7,422,136 | B1 | 9/2008 | Marczyk |
| 7,422,139 | B2 | 9/2008 | Shelton, IV et al. |
| 7,424,965 | B2 | 9/2008 | Racenet et al. |
| 7,431,188 | B1 | 10/2008 | Marczyk |
| 7,431,189 | B2 | 10/2008 | Shelton, IV et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,438,209 | B1 | 10/2008 | Hess et al. |
| 7,439,354 | B2 | 10/2008 | Lenges et al. |
| 7,441,684 | B2 | 10/2008 | Shelton, IV et al. |
| 7,441,685 | B1 | 10/2008 | Boudreaux |
| 7,442,201 | B2 | 10/2008 | Pugsley et al. |
| 7,448,525 | B2 | 11/2008 | Shelton, IV et al. |
| 7,455,208 | B2 | 11/2008 | Wales et al. |
| 7,461,767 | B2 | 12/2008 | Viola et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,473,253 | B2 | 1/2009 | Dycus et al. |
| 7,479,608 | B2 | 1/2009 | Smith |
| 7,481,347 | B2 | 1/2009 | Roy |
| 7,481,349 | B2 | 1/2009 | Holsten et al. |
| 7,481,824 | B2 | 1/2009 | Boudreaux et al. |
| 7,485,133 | B2 | 2/2009 | Cannon et al. |
| 7,490,749 | B2 | 2/2009 | Schall et al. |
| 7,494,039 | B2 | 2/2009 | Racenet et al. |
| 7,494,499 | B2 | 2/2009 | Nagase et al. |
| 7,500,979 | B2 | 3/2009 | Hueil et al. |
| 7,506,790 | B2 | 3/2009 | Shelton, IV |
| 7,506,791 | B2 | 3/2009 | Omaits et al. |
| 7,510,107 | B2 | 3/2009 | Timm et al. |
| 7,524,320 | B2 | 4/2009 | Tierney et al. |
| 7,530,985 | B2 | 5/2009 | Takemoto et al. |
| 7,546,940 | B2 | 6/2009 | Milliman et al. |
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,552,854 | B2 | 6/2009 | Wixey et al. |
| 7,556,185 | B2 | 7/2009 | Viola |
| 7,556,186 | B2 | 7/2009 | Milliman |
| 7,559,450 | B2 | 7/2009 | Wales et al. |
| 7,559,452 | B2 | 7/2009 | Wales et al. |

| Patent No. | Date | Inventor |
|---|---|---|
| 7,563,862 B2 | 7/2009 | Sieg et al. |
| 7,566,300 B2 | 7/2009 | Devierre et al. |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,003 B2 | 11/2009 | Stefanchik et al. |
| 7,624,902 B2 | 12/2009 | Marczyk et al. |
| 7,631,793 B2 | 12/2009 | Rethy et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,651,498 B2 | 1/2010 | Shifrin et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,307 B2 | 3/2010 | Danitz et al. |
| 7,686,826 B2 | 3/2010 | Lee et al. |
| 7,691,098 B2 | 4/2010 | Wallace et al. |
| 7,699,204 B2 | 4/2010 | Viola |
| 7,708,180 B2 | 5/2010 | Murray et al. |
| 7,708,758 B2 | 5/2010 | Lee et al. |
| 7,714,239 B2 | 5/2010 | Smith |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,743,960 B2 | 6/2010 | Whitman et al. |
| 7,744,627 B2 | 6/2010 | Orban, III et al. |
| 7,766,821 B2 | 8/2010 | Brunnen et al. |
| 7,766,894 B2 | 8/2010 | Weitzner et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,803,151 B2 | 9/2010 | Whitman |
| 7,806,891 B2 | 10/2010 | Nowlin et al. |
| 7,815,565 B2 | 10/2010 | Stefanchik et al. |
| 7,824,401 B2 | 11/2010 | Manzo et al. |
| 7,828,794 B2 | 11/2010 | Sartor |
| 7,828,808 B2 | 11/2010 | Hinman et al. |
| 7,832,611 B2 | 11/2010 | Boyden et al. |
| 7,836,400 B2 | 11/2010 | May et al. |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,846,149 B2 | 12/2010 | Jankowski |
| 7,870,989 B2 | 1/2011 | Viola et al. |
| 7,887,530 B2 | 2/2011 | Zemlok et al. |
| 7,909,191 B2 | 3/2011 | Baker et al. |
| 7,909,221 B2 | 3/2011 | Viola et al. |
| 7,914,543 B2 | 3/2011 | Roth et al. |
| 7,922,063 B2 | 4/2011 | Zemlok et al. |
| 7,938,307 B2 | 5/2011 | Bettuchi |
| 7,942,303 B2 | 5/2011 | Shah |
| 7,942,890 B2 | 5/2011 | D'Agostino et al. |
| 7,950,560 B2 | 5/2011 | Zemlok et al. |
| 7,959,050 B2 | 6/2011 | Smith et al. |
| 7,963,963 B2 | 6/2011 | Francischelli et al. |
| 7,967,180 B2 | 6/2011 | Scirica |
| 7,972,298 B2 | 7/2011 | Wallace et al. |
| 8,002,795 B2 | 8/2011 | Beetel |
| 8,011,551 B2 | 9/2011 | Marczyk et al. |
| 8,011,555 B2 | 9/2011 | Tarinelli et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,091,756 B2 | 1/2012 | Viola |
| 8,097,017 B2 | 1/2012 | Viola |
| 8,108,072 B2 | 1/2012 | Zhao et al. |
| 8,123,103 B2 | 2/2012 | Milliman |
| 8,152,041 B2 | 4/2012 | Kostrzewski |
| 8,157,152 B2 | 4/2012 | Holsten et al. |
| 8,167,895 B2 | 5/2012 | D'Agostino et al. |
| 8,211,125 B2 * | 7/2012 | Spivey .......... 606/151 |
| 8,220,468 B2 * | 7/2012 | Cooper et al. .......... 128/852 |
| 8,220,690 B2 | 7/2012 | Hess et al. |
| 8,225,799 B2 | 7/2012 | Bettuchi |
| 8,241,271 B2 | 8/2012 | Millman et al. |
| 8,245,898 B2 | 8/2012 | Smith et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 2002/0022836 A1 | 2/2002 | Goble et al. |
| 2002/0029036 A1 | 3/2002 | Goble et al. |
| 2002/0117534 A1 | 8/2002 | Green et al. |
| 2002/0134811 A1 | 9/2002 | Napier et al. |
| 2002/0165541 A1 | 11/2002 | Whitman |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0149424 A1* | 8/2003 | Barlev et al. .......... 606/1 |
| 2003/0153908 A1 | 8/2003 | Goble et al. |
| 2003/0195387 A1 | 10/2003 | Kortenbach et al. |
| 2003/0205029 A1* | 11/2003 | Chapolini et al. .......... 53/449 |
| 2003/0216732 A1 | 11/2003 | Truckai et al. |
| 2003/0220660 A1 | 11/2003 | Kortenbach et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0101822 A1 | 5/2004 | Wiesner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0243151 A1 | 12/2004 | Demmy et al. |

| | | | | | | |
|---|---|---|---|---|---|---|
| 2004/0243163 A1 | 12/2004 | Casiano et al. | | 2006/0111710 A1 | 5/2006 | Goble et al. |
| 2004/0243176 A1 | 12/2004 | Hahnen et al. | | 2006/0111711 A1 | 5/2006 | Goble |
| 2004/0254566 A1 | 12/2004 | Plicchi et al. | | 2006/0111723 A1 | 5/2006 | Chapolini et al. |
| 2004/0254608 A1 | 12/2004 | Huitema et al. | | 2006/0122636 A1 | 6/2006 | Bailly et al. |
| 2004/0267310 A1 | 12/2004 | Racenet et al. | | 2006/0142772 A1 | 6/2006 | Ralph et al. |
| 2005/0032511 A1 | 2/2005 | Malone et al. | | 2006/0149163 A1 | 7/2006 | Hibner et al. |
| 2005/0033357 A1 | 2/2005 | Braun | | 2006/0161185 A1 | 7/2006 | Saadat et al. |
| 2005/0054946 A1 | 3/2005 | Krzyzanowski | | 2006/0173470 A1 | 8/2006 | Oray et al. |
| 2005/0059997 A1 | 3/2005 | Bauman et al. | | 2006/0180634 A1 | 8/2006 | Shelton et al. |
| 2005/0070929 A1 | 3/2005 | Dalessandro et al. | | 2006/0183246 A1 | 8/2006 | Wiesner et al. |
| 2005/0080454 A1 | 4/2005 | Drews et al. | | 2006/0200123 A1 | 9/2006 | Ryan |
| 2005/0085693 A1 | 4/2005 | Belson et al. | | 2006/0212069 A1 | 9/2006 | Shelton, IV |
| 2005/0090817 A1 | 4/2005 | Phan | | 2006/0217729 A1 * | 9/2006 | Eskridge et al. ............... 606/80 |
| 2005/0103819 A1 | 5/2005 | Racenet et al. | | 2006/0226196 A1 | 10/2006 | Hueil et al. |
| 2005/0107814 A1 | 5/2005 | Johnston et al. | | 2006/0235469 A1 | 10/2006 | Viola |
| 2005/0107824 A1 | 5/2005 | Hillstead et al. | | 2006/0241655 A1 | 10/2006 | Viola |
| 2005/0113820 A1 | 5/2005 | Goble et al. | | 2006/0241692 A1 | 10/2006 | McGuckin, Jr. et al. |
| 2005/0119525 A1 | 6/2005 | Takemoto | | 2006/0244460 A1 | 11/2006 | Weaver |
| 2005/0119669 A1 | 6/2005 | Demmy | | 2006/0245971 A1 | 11/2006 | Burns et al. |
| 2005/0124855 A1 | 6/2005 | Jaffe et al. | | 2006/0258904 A1 | 11/2006 | Stefanchik et al. |
| 2005/0125009 A1 | 6/2005 | Perry et al. | | 2006/0259073 A1 | 11/2006 | Miyamoto et al. |
| 2005/0131173 A1 | 6/2005 | McDaniel et al. | | 2006/0264927 A1 | 11/2006 | Ryan |
| 2005/0131211 A1 | 6/2005 | Bayley et al. | | 2006/0264929 A1 | 11/2006 | Goble et al. |
| 2005/0131390 A1 | 6/2005 | Heinrich et al. | | 2006/0271042 A1 | 11/2006 | Latterell et al. |
| 2005/0131436 A1 | 6/2005 | Johnston et al. | | 2006/0271102 A1 | 11/2006 | Bosshard et al. |
| 2005/0131437 A1 | 6/2005 | Johnston et al. | | 2006/0278680 A1 | 12/2006 | Viola et al. |
| 2005/0131457 A1 | 6/2005 | Douglas et al. | | 2006/0278681 A1 | 12/2006 | Viola et al. |
| 2005/0137454 A1 | 6/2005 | Saadat et al. | | 2006/0289602 A1 | 12/2006 | Wales et al. |
| 2005/0137455 A1 | 6/2005 | Ewers et al. | | 2006/0291981 A1 | 12/2006 | Viola et al. |
| 2005/0143759 A1 | 6/2005 | Kelly | | 2007/0023476 A1 | 2/2007 | Whitman et al. |
| 2005/0145675 A1 | 7/2005 | Hartwick et al. | | 2007/0023477 A1 | 2/2007 | Whitman et al. |
| 2005/0154258 A1 | 7/2005 | Tartaglia et al. | | 2007/0027468 A1 | 2/2007 | Wales et al. |
| 2005/0165419 A1 | 7/2005 | Sauer et al. | | 2007/0027469 A1 | 2/2007 | Smith et al. |
| 2005/0165435 A1 | 7/2005 | Johnston et al. | | 2007/0034668 A1 | 2/2007 | Holsten et al. |
| 2005/0169974 A1 | 8/2005 | Tenerz et al. | | 2007/0055219 A1 | 3/2007 | Whitman et al. |
| 2005/0171522 A1 | 8/2005 | Christopherson | | 2007/0070574 A1 | 3/2007 | Nerheim et al. |
| 2005/0177181 A1 | 8/2005 | Kagan et al. | | 2007/0073341 A1 | 3/2007 | Smith et al. |
| 2005/0182298 A1 | 8/2005 | Ikeda et al. | | 2007/0078484 A1 | 4/2007 | Talarico et al. |
| 2005/0184121 A1 | 8/2005 | Heinrich | | 2007/0083193 A1 | 4/2007 | Werneth et al. |
| 2005/0187545 A1 | 8/2005 | Hooven et al. | | 2007/0084897 A1 | 4/2007 | Shelton, IV et al. |
| 2005/0187572 A1 | 8/2005 | Johnston et al. | | 2007/0102472 A1 | 5/2007 | Shelton, IV |
| 2005/0187576 A1 | 8/2005 | Whitman et al. | | 2007/0102473 A1 | 5/2007 | Shelton, IV et al. |
| 2005/0189397 A1 | 9/2005 | Jankowski | | 2007/0106317 A1 | 5/2007 | Shelton, IV et al. |
| 2005/0192609 A1 | 9/2005 | Whitman et al. | | 2007/0114261 A1 | 5/2007 | Ortiz et al. |
| 2005/0192628 A1 | 9/2005 | Viola | | 2007/0135803 A1 | 6/2007 | Belson |
| 2005/0203550 A1 | 9/2005 | Laufer et al. | | 2007/0158358 A1 | 7/2007 | Mason, II et al. |
| 2005/0216055 A1 | 9/2005 | Scirica et al. | | 2007/0170225 A1 | 7/2007 | Shelton, IV et al. |
| 2005/0228224 A1 | 10/2005 | Okada et al. | | 2007/0173806 A1 | 7/2007 | Orszulak et al. |
| 2005/0240222 A1 | 10/2005 | Shipp | | 2007/0173813 A1 | 7/2007 | Odom |
| 2005/0245965 A1 | 11/2005 | Orban, III et al. | | 2007/0175949 A1 | 8/2007 | Shelton, IV et al. |
| 2005/0251128 A1 | 11/2005 | Amoah | | 2007/0175950 A1 | 8/2007 | Shelton, IV et al. |
| 2005/0256522 A1 | 11/2005 | Francischelli et al. | | 2007/0175951 A1 | 8/2007 | Shelton, IV et al. |
| 2005/0261676 A1 | 11/2005 | Hall et al. | | 2007/0175953 A1 | 8/2007 | Shelton, IV et al. |
| 2005/0261677 A1 | 11/2005 | Hall et al. | | 2007/0175955 A1 | 8/2007 | Shelton, IV et al. |
| 2005/0263563 A1 | 12/2005 | Racenet et al. | | 2007/0175957 A1 | 8/2007 | Shelton, IV et al. |
| 2005/0267455 A1 | 12/2005 | Eggers et al. | | 2007/0175958 A1 | 8/2007 | Shelton, IV et al. |
| 2005/0274768 A1 | 12/2005 | Cummins et al. | | 2007/0175964 A1 | 8/2007 | Shelton, IV et al. |
| 2006/0004407 A1 | 1/2006 | Hiles et al. | | 2007/0179476 A1 | 8/2007 | Shelton, IV et al. |
| 2006/0008787 A1 | 1/2006 | Hayman et al. | | 2007/0181632 A1 | 8/2007 | Milliman |
| 2006/0011699 A1 | 1/2006 | Olson et al. | | 2007/0194079 A1 | 8/2007 | Hueil et al. |
| 2006/0015009 A1 | 1/2006 | Jaffe et al. | | 2007/0194081 A1 | 8/2007 | Hueil et al. |
| 2006/0020247 A1 | 1/2006 | Kagan et al. | | 2007/0194082 A1 | 8/2007 | Morgan et al. |
| 2006/0020336 A1 | 1/2006 | Liddicoat | | 2007/0203510 A1 | 8/2007 | Bettuchi |
| 2006/0025811 A1 | 2/2006 | Shelton, IV | | 2007/0213750 A1 | 9/2007 | Weadock |
| 2006/0025812 A1 | 2/2006 | Shelton, IV | | 2007/0221700 A1 | 9/2007 | Ortiz et al. |
| 2006/0025813 A1 | 2/2006 | Shelton et al. | | 2007/0221701 A1 | 9/2007 | Ortiz et al. |
| 2006/0047275 A1 | 3/2006 | Goble | | 2007/0225562 A1 | 9/2007 | Spivey et al. |
| 2006/0047303 A1 | 3/2006 | Ortiz et al. | | 2007/0246505 A1 | 10/2007 | Pace-Floridia et al. |
| 2006/0047307 A1 | 3/2006 | Ortiz et al. | | 2007/0260278 A1 | 11/2007 | Wheeler et al. |
| 2006/0049229 A1 | 3/2006 | Milliman et al. | | 2007/0270784 A1 | 11/2007 | Smith et al. |
| 2006/0052825 A1 | 3/2006 | Ransick et al. | | 2007/0270884 A1 | 11/2007 | Smith et al. |
| 2006/0060630 A1 | 3/2006 | Shelton, IV et al. | | 2007/0288044 A1 | 12/2007 | Jinno et al. |
| 2006/0064086 A1 | 3/2006 | Odom | | 2007/0295780 A1 | 12/2007 | Shelton et al. |
| 2006/0079735 A1 | 4/2006 | Martone et al. | | 2007/0299427 A1 | 12/2007 | Yeung et al. |
| 2006/0085031 A1 | 4/2006 | Bettuchi | | 2008/0015598 A1 | 1/2008 | Prommersberger |
| 2006/0085033 A1 | 4/2006 | Criscuolo et al. | | 2008/0029570 A1 | 2/2008 | Shelton et al. |
| 2006/0086032 A1 | 4/2006 | Valencic et al. | | 2008/0029573 A1 | 2/2008 | Shelton et al. |
| 2006/0100643 A1 | 5/2006 | Laufer et al. | | 2008/0029574 A1 | 2/2008 | Shelton et al. |
| 2006/0108393 A1 | 5/2006 | Heinrich et al. | | 2008/0029575 A1 | 2/2008 | Shelton et al. |

| Publication No. | Date | Inventor |
|---|---|---|
| 2008/0029576 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0210738 A1 | 9/2008 | Shelton et al. |
| 2008/0228029 A1 | 9/2008 | Mikkaichi et al. |
| 2008/0237296 A1 | 10/2008 | Boudreaux et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314955 A1 | 12/2008 | Boudreaux et al. |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0093728 A1 | 4/2009 | Hyde et al. |
| 2009/0108048 A1 | 4/2009 | Zemlok et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1 | 6/2009 | Kane et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2009/0308907 A1 | 12/2009 | Nalagatla et al. |
| 2010/0012704 A1 | 1/2010 | Tarinelli Racenet et al. |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096431 A1 | 4/2010 | Smith et al. |
| 2010/0096435 A1 | 4/2010 | Fuchs et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0145146 A1 | 6/2010 | Melder |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0186219 A1 | 7/2010 | Smith |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1* | 8/2010 | Yates et al. .................. 227/176.1 |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |

| | | | | | | |
|---|---|---|---|---|---|---|
| 2010/0243707 A1 | 9/2010 | Olson et al. | | 2011/0295295 A1 | 12/2011 | Shelton, IV et al. |
| 2010/0243708 A1 | 9/2010 | Aranyi et al. | | 2012/0022523 A1 | 1/2012 | Smith et al. |
| 2010/0243709 A1 | 9/2010 | Hess et al. | | 2012/0024934 A1 | 2/2012 | Shelton, IV et al. |
| 2010/0258611 A1 | 10/2010 | Smith et al. | | 2012/0024935 A1 | 2/2012 | Shelton, IV et al. |
| 2010/0264193 A1 | 10/2010 | Huang et al. | | 2012/0024936 A1 | 2/2012 | Baxter, III et al. |
| 2010/0264194 A1 | 10/2010 | Huang et al. | | 2012/0029272 A1 | 2/2012 | Shelton, IV et al. |
| 2010/0276471 A1 | 11/2010 | Whitman | | 2012/0029544 A1 | 2/2012 | Shelton, IV et al. |
| 2010/0294827 A1 | 11/2010 | Boyden et al. | | 2012/0029547 A1 | 2/2012 | Shelton, IV et al. |
| 2010/0294829 A1 | 11/2010 | Giordano et al. | | 2012/0046692 A1 | 2/2012 | Smith et al. |
| 2010/0301095 A1 | 12/2010 | Shelton, IV et al. | | 2012/0061448 A1 | 3/2012 | Zingman |
| 2010/0301096 A1 | 12/2010 | Moore et al. | | 2012/0071711 A1 | 3/2012 | Shelton, IV et al. |
| 2010/0305552 A1 | 12/2010 | Shelton, IV et al. | | 2012/0071866 A1 | 3/2012 | Kerr et al. |
| 2010/0308100 A1 | 12/2010 | Boudreaux | | 2012/0074196 A1 | 3/2012 | Shelton, IV et al. |
| 2010/0312261 A1 | 12/2010 | Suzuki et al. | | 2012/0074198 A1 | 3/2012 | Huitema et al. |
| 2011/0006099 A1 | 1/2011 | Hall et al. | | 2012/0074200 A1 | 3/2012 | Schmid et al. |
| 2011/0006101 A1 | 1/2011 | Hall et al. | | 2012/0074201 A1 | 3/2012 | Baxter, III et al. |
| 2011/0006103 A1 | 1/2011 | Laurent et al. | | 2012/0080332 A1 | 4/2012 | Shelton, IV et al. |
| 2011/0011914 A1 | 1/2011 | Baxter, III et al. | | 2012/0080333 A1 | 4/2012 | Woodard, Jr. et al. |
| 2011/0011915 A1 | 1/2011 | Shelton, IV | | 2012/0080334 A1 | 4/2012 | Shelton, IV et al. |
| 2011/0017801 A1 | 1/2011 | Zemlok et al. | | 2012/0080335 A1 | 4/2012 | Shelton, IV et al. |
| 2011/0022032 A1 | 1/2011 | Zemlok et al. | | 2012/0080336 A1 | 4/2012 | Shelton, IV et al. |
| 2011/0024477 A1 | 2/2011 | Hall et al. | | 2012/0080337 A1 | 4/2012 | Shelton, IV et al. |
| 2011/0024478 A1 | 2/2011 | Shelton, IV | | 2012/0080338 A1 | 4/2012 | Shelton, IV et al. |
| 2011/0024479 A1 | 2/2011 | Swensgard et al. | | 2012/0080339 A1 | 4/2012 | Shelton, IV et al. |
| 2011/0036887 A1 | 2/2011 | Zemlok et al. | | 2012/0080340 A1 | 4/2012 | Shelton, IV et al. |
| 2011/0042441 A1 | 2/2011 | Shelton, IV et al. | | 2012/0080344 A1 | 4/2012 | Shelton, IV |
| 2011/0060363 A1 | 3/2011 | Hess et al. | | 2012/0080345 A1 | 4/2012 | Morgan et al. |
| 2011/0062212 A1 | 3/2011 | Shelton, IV et al. | | 2012/0080475 A1 | 4/2012 | Smith et al. |
| 2011/0068145 A1 | 3/2011 | Bedi et al. | | 2012/0080477 A1 | 4/2012 | Leimbach et al. |
| 2011/0068148 A1 | 3/2011 | Hall et al. | | 2012/0080478 A1 | 4/2012 | Morgan et al. |
| 2011/0084112 A1 | 4/2011 | Kostrzewski | | 2012/0080479 A1 | 4/2012 | Shelton, IV |
| 2011/0084113 A1 | 4/2011 | Bedi et al. | | 2012/0080480 A1 | 4/2012 | Woodard, Jr. et al. |
| 2011/0084115 A1 | 4/2011 | Bedi et al. | | 2012/0080481 A1 | 4/2012 | Widenhouse et al. |
| 2011/0087276 A1 | 4/2011 | Bedi et al. | | 2012/0080482 A1 | 4/2012 | Schall et al. |
| 2011/0087279 A1 | 4/2011 | Shah et al. | | 2012/0080483 A1 | 4/2012 | Riestenberg et al. |
| 2011/0095068 A1 | 4/2011 | Patel | | 2012/0080484 A1 | 4/2012 | Morgan et al. |
| 2011/0101065 A1 | 5/2011 | Milliman | | 2012/0080485 A1 | 4/2012 | Woodard, Jr. et al. |
| 2011/0114697 A1 | 5/2011 | Baxter, III et al. | | 2012/0080486 A1 | 4/2012 | Woodard, Jr. et al. |
| 2011/0114698 A1 | 5/2011 | Baxter, III et al. | | 2012/0080487 A1 | 4/2012 | Woodard, Jr. et al. |
| 2011/0114699 A1 | 5/2011 | Baxter, III et al. | | 2012/0080488 A1 | 4/2012 | Shelton, IV et al. |
| 2011/0114700 A1 | 5/2011 | Baxter, III et al. | | 2012/0080489 A1 | 4/2012 | Shelton, IV et al. |
| 2011/0118761 A1 | 5/2011 | Baxter, III et al. | | 2012/0080490 A1 | 4/2012 | Shelton, IV et al. |
| 2011/0121051 A1 | 5/2011 | Shelton, IV et al. | | 2012/0080491 A1 | 4/2012 | Shelton, IV et al. |
| 2011/0121052 A1 | 5/2011 | Shelton, IV et al. | | 2012/0080493 A1 | 4/2012 | Shelton, IV et al. |
| 2011/0125176 A1 | 5/2011 | Yates et al. | | 2012/0080496 A1 | 4/2012 | Schall et al. |
| 2011/0125177 A1 | 5/2011 | Yates et al. | | 2012/0080498 A1 | 4/2012 | Shelton, IV et al. |
| 2011/0132962 A1 | 6/2011 | Hall et al. | | 2012/0080499 A1 | 4/2012 | Schall et al. |
| 2011/0132963 A1 | 6/2011 | Giordano et al. | | 2012/0080500 A1 | 4/2012 | Morgan et al. |
| 2011/0132964 A1 | 6/2011 | Weisenburgh, II et al. | | 2012/0080501 A1 | 4/2012 | Morgan et al. |
| 2011/0132965 A1 | 6/2011 | Moore et al. | | 2012/0080502 A1 | 4/2012 | Morgan et al. |
| 2011/0139852 A1 | 6/2011 | Zingman | | 2012/0080503 A1 | 4/2012 | Woodard, Jr. et al. |
| 2011/0144430 A1 | 6/2011 | Spivey et al. | | 2012/0083833 A1 | 4/2012 | Shelton, IV et al. |
| 2011/0147433 A1 | 6/2011 | Shelton, IV et al. | | 2012/0083834 A1 | 4/2012 | Shelton, IV et al. |
| 2011/0147434 A1 | 6/2011 | Hueil et al. | | 2012/0083835 A1 | 4/2012 | Shelton, IV et al. |
| 2011/0155780 A1 | 6/2011 | Boudreaux | | 2012/0083836 A1 | 4/2012 | Shelton, IV et al. |
| 2011/0155781 A1 | 6/2011 | Swensgard et al. | | 2012/0132450 A1 | 5/2012 | Timm et al. |
| 2011/0155785 A1 | 6/2011 | Laurent et al. | | 2012/0138660 A1 | 6/2012 | Shelton, IV |
| 2011/0155787 A1 | 6/2011 | Baxter, III et al. | | 2012/0160721 A1 | 6/2012 | Shelton, IV et al. |
| 2011/0163147 A1 | 7/2011 | Laurent et al. | | 2012/0175399 A1 | 7/2012 | Shelton et al. |
| 2011/0174860 A1 | 7/2011 | Shelton, IV et al. | | 2012/0187179 A1 | 7/2012 | Gleiman |
| 2011/0174863 A1 | 7/2011 | Shelton, IV et al. | | 2012/0199630 A1 | 8/2012 | Shelton, IV et al. |
| 2011/0178536 A1 | 7/2011 | Kostrzewski | | 2012/0199631 A1 | 8/2012 | Shelton, IV et al. |
| 2011/0192882 A1 | 8/2011 | Hess et al. | | 2012/0199632 A1 | 8/2012 | Spivey et al. |
| 2011/0210156 A1 | 9/2011 | Smith et al. | | 2012/0199633 A1 | 8/2012 | Shelton, IV et al. |
| 2011/0226837 A1 | 9/2011 | Baxter, III et al. | | 2012/0203247 A1 | 8/2012 | Shelton, IV et al. |
| 2011/0233258 A1 | 9/2011 | Boudreaux | | 2012/0205421 A1 | 8/2012 | Shelton, IV |
| 2011/0253766 A1 | 10/2011 | Baxter, III et al. | | 2012/0211546 A1 | 8/2012 | Shelton, IV |
| 2011/0275901 A1 | 11/2011 | Shelton, IV | | 2012/0234890 A1 | 9/2012 | Aronhalt et al. |
| 2011/0276083 A1 | 11/2011 | Shelton, IV et al. | | 2012/0234891 A1 | 9/2012 | Aronhalt et al. |
| 2011/0288573 A1 | 11/2011 | Yates et al. | | 2012/0234892 A1 | 9/2012 | Aronhalt et al. |
| 2011/0290851 A1 | 12/2011 | Shelton, IV | | 2012/0234893 A1 | 9/2012 | Schuckmann et al. |
| 2011/0290853 A1 | 12/2011 | Shelton, IV et al. | | 2012/0234895 A1 | 9/2012 | O'Connor et al. |
| 2011/0290854 A1 | 12/2011 | Timm et al. | | 2012/0234896 A1 | 9/2012 | Ellerhorst et al. |
| 2011/0290855 A1 | 12/2011 | Moore et al. | | 2012/0234897 A1 | 9/2012 | Shelton, IV et al. |
| 2011/0290856 A1 | 12/2011 | Shelton, IV et al. | | 2012/0234898 A1 | 9/2012 | Shelton, IV et al. |
| 2011/0290857 A1 | 12/2011 | Shelton, IV et al. | | 2012/0234899 A1 | 9/2012 | Scheib et al. |
| 2011/0295242 A1 | 12/2011 | Spivey et al. | | 2012/0234900 A1 | 9/2012 | Swayze |
| 2011/0295269 A1 | 12/2011 | Swensgard et al. | | 2012/0238823 A1 | 9/2012 | Hagerty et al. |
| 2011/0295270 A1 | 12/2011 | Giordano et al. | | 2012/0238824 A1 | 9/2012 | Widenhouse et al. |

| | | | |
|---|---|---|---|
| 2012/0238826 A1 | 9/2012 | Yoo et al. | |
| 2012/0238829 A1 | 9/2012 | Shelton, IV et al. | |
| 2012/0239009 A1 | 9/2012 | Mollere et al. | |
| 2012/0239010 A1 | 9/2012 | Shelton, IV et al. | |
| 2012/0239012 A1 | 9/2012 | Laurent et al. | |
| 2012/0239075 A1 | 9/2012 | Widenhouse et al. | |
| 2012/0239082 A1 | 9/2012 | Shelton, IV et al. | |
| 2012/0241491 A1 | 9/2012 | Aldridge et al. | |
| 2012/0241492 A1 | 9/2012 | Shelton, IV et al. | |
| 2012/0241493 A1 | 9/2012 | Baxter, III et al. | |
| 2012/0241496 A1 | 9/2012 | Mandakolathur Vasudevan et al. | |
| 2012/0241497 A1 | 9/2012 | Mandakolathur Vasudevan et al. | |
| 2012/0241498 A1 | 9/2012 | Gonzalez et al. | |
| 2012/0241499 A1 | 9/2012 | Baxter, III et al. | |
| 2012/0241500 A1 | 9/2012 | Timmer et al. | |
| 2012/0241501 A1 | 9/2012 | Swayze et al. | |
| 2012/0241502 A1 | 9/2012 | Aldridge et al. | |
| 2012/0241503 A1 | 9/2012 | Baxter, III et al. | |
| 2012/0241505 A1 | 9/2012 | Alexander, III et al. | |
| 2012/0248169 A1 | 10/2012 | Widenhouse et al. | |
| 2012/0253298 A1 | 10/2012 | Henderson et al. | |
| 2012/0265230 A1 | 10/2012 | Yates et al. | |

FOREIGN PATENT DOCUMENTS

| | | | |
|---|---|---|---|
| CA | 2514274 A1 | 1/2006 | |
| CN | 1634601 A | 7/2005 | |
| CN | 1868411 A | 11/2006 | |
| CN | 1915180 A | 2/2007 | |
| CN | 101095621 A | 1/2008 | |
| DE | 273689 C | 5/1914 | |
| DE | 9412228 U | 9/1994 | |
| DE | 19509116 A1 | 9/1996 | |
| DE | 19851291 A1 | 1/2000 | |
| DE | 19924311 A1 | 11/2000 | |
| DE | 69328576 T2 | 1/2001 | |
| DE | 10052679 A1 | 5/2001 | |
| DE | 20112837 U1 | 10/2001 | |
| DE | 20121753 U1 | 4/2003 | |
| DE | 10314072 A1 | 10/2004 | |
| EP | 0122046 A1 | 10/1984 | |
| EP | 0070230 B1 | 10/1985 | |
| EP | 0387980 B1 | 10/1985 | |
| EP | 0033548 B1 | 5/1986 | |
| EP | 0276104 A2 | 7/1988 | |
| EP | 0248844 B1 | 1/1993 | |
| EP | 0545029 A1 | 6/1993 | |
| EP | 0277959 B1 | 10/1993 | |
| EP | 0233940 B1 | 11/1993 | |
| EP | 0261230 B1 | 11/1993 | |
| EP | 0639349 A2 | 2/1994 | |
| EP | 0324636 B1 | 3/1994 | |
| EP | 0593920 A1 | 4/1994 | |
| EP | 0594148 A1 | 4/1994 | |
| EP | 0427949 B1 | 6/1994 | |
| EP | 0523174 B1 | 6/1994 | |
| EP | 0600182 A2 | 6/1994 | |
| EP | 0310431 B1 | 11/1994 | |
| EP | 0375302 B1 | 11/1994 | |
| EP | 0376562 B1 | 11/1994 | |
| EP | 0630612 A1 | 12/1994 | |
| EP | 0634144 A1 | 1/1995 | |
| EP | 0646356 A2 | 4/1995 | |
| EP | 0646357 A1 | 4/1995 | |
| EP | 0653189 A2 | 5/1995 | |
| EP | 0669104 A1 | 8/1995 | |
| EP | 0511470 B1 | 10/1995 | |
| EP | 0679367 A2 | 11/1995 | |
| EP | 0392547 B1 | 12/1995 | |
| EP | 0685204 A1 | 12/1995 | |
| EP | 0364216 B1 | 1/1996 | |
| EP | 0699418 A1 | 3/1996 | |
| EP | 0702937 A1 | 3/1996 | |
| EP | 0705571 A1 | 4/1996 | |
| EP | 0711611 A2 | 5/1996 | |
| EP | 0484677 B2 | 6/1996 | |
| EP | 0541987 B1 | 7/1996 | |
| EP | 0667119 B1 | 7/1996 | |
| EP | 0708618 B1 | 3/1997 | |
| EP | 0770355 A1 | 5/1997 | |
| EP | 0503662 B1 | 6/1997 | |
| EP | 0447121 B1 | 7/1997 | |
| EP | 0625077 B1 | 7/1997 | |
| EP | 0633749 B1 | 8/1997 | |
| EP | 0710090 B1 | 8/1997 | |
| EP | 0578425 B1 | 9/1997 | |
| EP | 0625335 B1 | 11/1997 | |
| EP | 0552423 B1 | 1/1998 | |
| EP | 0592244 B1 | 1/1998 | |
| EP | 0648476 B1 | 1/1998 | |
| EP | 0649290 B1 | 3/1998 | |
| EP | 0598618 B1 | 9/1998 | |
| EP | 0676173 B1 | 9/1998 | |
| EP | 0678007 B1 | 9/1998 | |
| EP | 0603472 B1 | 11/1998 | |
| EP | 0605351 B1 | 11/1998 | |
| EP | 0878169 A1 | 11/1998 | |
| EP | 0879742 A1 | 11/1998 | |
| EP | 0695144 B1 | 12/1998 | |
| EP | 0722296 B1 | 12/1998 | |
| EP | 0760230 B1 | 2/1999 | |
| EP | 0623316 B1 | 3/1999 | |
| EP | 0650701 B1 | 3/1999 | |
| EP | 0537572 B1 | 6/1999 | |
| EP | 0923907 A1 | 6/1999 | |
| EP | 0843906 B1 | 3/2000 | |
| EP | 0552050 B1 | 5/2000 | |
| EP | 0833592 B1 | 5/2000 | |
| EP | 0830094 B1 | 9/2000 | |
| EP | 1034747 A1 | 9/2000 | |
| EP | 1034748 A1 | 9/2000 | |
| EP | 0694290 B1 | 11/2000 | |
| EP | 1050278 A1 | 11/2000 | |
| EP | 1053719 A1 | 11/2000 | |
| EP | 1053720 A1 | 11/2000 | |
| EP | 1055399 A1 | 11/2000 | |
| EP | 1055400 A1 | 11/2000 | |
| EP | 1080694 A1 | 3/2001 | |
| EP | 1090592 A1 | 4/2001 | |
| EP | 1095627 A1 | 5/2001 | |
| EP | 1256318 B1 | 5/2001 | |
| EP | 0806914 B1 | 9/2001 | |
| EP | 0768840 B1 | 12/2001 | |
| EP | 0908152 B1 | 1/2002 | |
| EP | 0872213 B1 | 5/2002 | |
| EP | 0862386 B1 | 6/2002 | |
| EP | 0949886 B1 | 9/2002 | |
| EP | 1238634 A2 | 9/2002 | |
| EP | 0858295 B1 | 12/2002 | |
| EP | 0656188 B1 | 1/2003 | |
| EP | 1284120 A1 | 2/2003 | |
| EP | 1287788 A1 | 3/2003 | |
| EP | 0717966 B1 | 4/2003 | |
| EP | 0869742 B1 | 5/2003 | |
| EP | 0829235 B1 | 6/2003 | |
| EP | 0887046 B1 | 7/2003 | |
| EP | 0852480 B1 | 8/2003 | |
| EP | 0891154 B1 | 9/2003 | |
| EP | 0813843 B1 | 10/2003 | |
| EP | 0873089 B1 | 10/2003 | |
| EP | 0856326 B1 | 11/2003 | |
| EP | 1374788 A1 | 1/2004 | |
| EP | 0741996 B1 | 2/2004 | |
| EP | 0814712 B1 | 2/2004 | |
| EP | 1402837 A1 | 3/2004 | |
| EP | 0705570 B1 | 4/2004 | |
| EP | 0959784 B1 | 4/2004 | |
| EP | 1407719 A2 | 4/2004 | |
| EP | 1086713 B1 | 5/2004 | |
| EP | 0996378 B1 | 6/2004 | |
| EP | 1426012 A1 | 6/2004 | |
| EP | 0833593 B2 | 7/2004 | |
| EP | 1442694 A1 | 8/2004 | |
| EP | 0888749 B1 | 9/2004 | |
| EP | 0959786 B1 | 9/2004 | |
| EP | 1459695 A1 | 9/2004 | |
| EP | 1473819 A1 | 11/2004 | |
| EP | 1477119 A1 | 11/2004 | |
| EP | 1479345 A1 | 11/2004 | |

| | | | | | | |
|---|---|---|---|---|---|---|
| EP | 1479347 | A1 | 11/2004 | EP | 1759645 B1 | 11/2008 |
| EP | 1479348 | A1 | 11/2004 | EP | 1693008 B1 | 12/2008 |
| EP | 0754437 | B2 | 12/2004 | EP | 1759640 B1 | 12/2008 |
| EP | 1025807 | B1 | 12/2004 | EP | 2000102 A2 | 12/2008 |
| EP | 1001710 | B1 | 1/2005 | EP | 2008595 A2 | 12/2008 |
| EP | 1520521 | A1 | 4/2005 | EP | 1736104 B1 | 3/2009 |
| EP | 1520523 | A1 | 4/2005 | EP | 1749486 B1 | 3/2009 |
| EP | 1520525 | A1 | 4/2005 | EP | 2039316 A2 | 3/2009 |
| EP | 1522264 | A1 | 4/2005 | EP | 1721576 B1 | 4/2009 |
| EP | 1523942 | A2 | 4/2005 | EP | 1733686 B1 | 4/2009 |
| EP | 1550408 | A1 | 7/2005 | EP | 2044890 A1 | 4/2009 |
| EP | 1557129 | A1 | 7/2005 | EP | 1550413 B1 | 6/2009 |
| EP | 1064883 | B1 | 8/2005 | EP | 1745748 B1 | 8/2009 |
| EP | 1067876 | B1 | 8/2005 | EP | 2090237 A1 | 8/2009 |
| EP | 0870473 | B1 | 9/2005 | EP | 2090256 A2 | 8/2009 |
| EP | 1157666 | B1 | 9/2005 | EP | 2095777 A2 | 9/2009 |
| EP | 0880338 | B1 | 10/2005 | EP | 2110082 A1 | 10/2009 |
| EP | 1158917 | B1 | 11/2005 | EP | 1813208 B1 | 11/2009 |
| EP | 1344498 | B1 | 11/2005 | EP | 2116195 A1 | 11/2009 |
| EP | 1330989 | B1 | 12/2005 | EP | 1607050 B1 | 12/2009 |
| EP | 0771176 | B2 | 1/2006 | EP | 1815804 B1 | 12/2009 |
| EP | 1621138 | A2 | 2/2006 | EP | 1566150 B1 | 4/2010 |
| EP | 1621139 | A2 | 2/2006 | EP | 1813206 B1 | 4/2010 |
| EP | 1621141 | A2 | 2/2006 | EP | 1769754 B1 | 6/2010 |
| EP | 1621145 | A2 | 2/2006 | EP | 1535565 B1 | 10/2010 |
| EP | 1621151 | A2 | 2/2006 | EP | 1702570 B1 | 10/2010 |
| EP | 1034746 | B1 | 3/2006 | EP | 1785098 B1 | 10/2010 |
| EP | 1632191 | A2 | 3/2006 | EP | 1627605 B1 | 12/2010 |
| EP | 1065981 | B1 | 5/2006 | EP | 1785102 B1 | 1/2012 |
| EP | 1082944 | B1 | 5/2006 | FR | 1112936 A | 3/1956 |
| EP | 1652481 | A2 | 5/2006 | FR | 2598905 A1 | 11/1987 |
| EP | 1382303 | B1 | 6/2006 | FR | 2765794 A | 1/1999 |
| EP | 1253866 | B1 | 7/2006 | GB | 939929 A | 10/1963 |
| EP | 1032318 | B1 | 8/2006 | GB | 1210522 A | 10/1970 |
| EP | 1045672 | B1 | 8/2006 | GB | 1217159 A | 12/1970 |
| EP | 1617768 | B1 | 8/2006 | GB | 1339394 A | 12/1973 |
| EP | 1693015 | A2 | 8/2006 | GB | 2109241 A | 6/1983 |
| EP | 1400214 | B1 | 9/2006 | GB | 2272159 A | 5/1994 |
| EP | 1702567 | A2 | 9/2006 | GB | 2284242 A | 5/1995 |
| EP | 1129665 | B1 | 11/2006 | GB | 2336214 A | 10/1999 |
| EP | 1400206 | B1 | 11/2006 | GB | 2425903 A | 11/2006 |
| EP | 1721568 | A1 | 11/2006 | JP | 58500053 A * | 1/1983 |
| EP | 1256317 | B1 | 12/2006 | JP | 61-98249 A | 5/1986 |
| EP | 1285633 | B1 | 12/2006 | JP | 63203149 * | 8/1988 |
| EP | 1728473 | A1 | 12/2006 | JP | 3-12126 A | 1/1991 |
| EP | 1728475 | A2 | 12/2006 | JP | 5-212039 A | 8/1993 |
| EP | 1479346 | B1 | 1/2007 | JP | 6007357 A | 1/1994 |
| EP | 1484024 | B1 | 1/2007 | JP | 7051273 A | 2/1995 |
| EP | 1754445 | A2 | 2/2007 | JP | 8033641 A | 2/1996 |
| EP | 1759812 | A1 | 3/2007 | JP | 8229050 A | 9/1996 |
| EP | 1767163 | A1 | 3/2007 | JP | 2000033071 A | 2/2000 |
| EP | 1769756 | A1 | 4/2007 | JP | 2000171730 A | 6/2000 |
| EP | 1769758 | A1 | 4/2007 | JP | 2000287987 A | 10/2000 |
| EP | 1581128 | B1 | 5/2007 | JP | 2000325303 A | 11/2000 |
| EP | 1785097 | A2 | 5/2007 | JP | 2001-514541 A | 9/2001 |
| EP | 1790293 | A2 | 5/2007 | JP | 2001286477 A | 10/2001 |
| EP | 1800610 | A1 | 6/2007 | JP | 2002143078 A | 5/2002 |
| EP | 1300117 | B1 | 8/2007 | JP | 2002369820 A | 12/2002 |
| EP | 1813199 | A1 | 8/2007 | JP | 2004-344663 | 12/2004 |
| EP | 1813201 | A1 | 8/2007 | JP | 2005-028149 A | 2/2005 |
| EP | 1813203 | A2 | 8/2007 | JP | 2005505322 T | 2/2005 |
| EP | 1813207 | A1 | 8/2007 | JP | 2005103293 A | 4/2005 |
| EP | 1813209 | A1 | 8/2007 | JP | 2005131163 A | 5/2005 |
| EP | 1487359 | B1 | 10/2007 | JP | 2005131164 A | 5/2005 |
| EP | 1599146 | B1 | 10/2007 | JP | 2005131173 A | 5/2005 |
| EP | 1839596 | A1 | 10/2007 | JP | 2005131211 A | 5/2005 |
| EP | 2110083 | A2 | 10/2007 | JP | 2005131212 A | 5/2005 |
| EP | 1857057 | A2 | 11/2007 | JP | 2005137423 A | 6/2005 |
| EP | 1402821 | B1 | 12/2007 | JP | 2005152416 A | 6/2005 |
| EP | 1872727 | A1 | 1/2008 | JP | 2005-523105 A | 8/2005 |
| EP | 1897502 | A1 | 3/2008 | JP | 2005524474 A | 8/2005 |
| EP | 1330201 | B1 | 6/2008 | JP | 2006-281405 A | 10/2006 |
| EP | 1702568 | B1 | 7/2008 | RU | 2008830 C1 | 3/1994 |
| EP | 1943957 | A2 | 7/2008 | RU | 2187249 C2 | 2/2002 |
| EP | 1943964 | A1 | 7/2008 | RU | 2225170 C2 | 3/2004 |
| EP | 1943976 | A2 | 7/2008 | SU | 189517 A | 1/1967 |
| EP | 1593337 | B1 | 8/2008 | SU | 328636 A | 9/1972 |
| EP | 1970014 | A1 | 9/2008 | SU | 886900 A1 * | 12/1981 |
| EP | 1980213 | A2 | 10/2008 | SU | 1333319 A2 | 8/1987 |

| | | | | | | | |
|---|---|---|---|---|---|---|---|
| SU | 1377053 | A1 | 2/1988 | WO | WO 99/25261 | A1 | 5/1999 |
| SU | 1561964 | A1 | 5/1990 | WO | WO 99/29244 | A1 | 6/1999 |
| SU | 1722476 | A1 | 3/1992 | WO | WO 99/34744 | A1 | 7/1999 |
| WO | WO 82/02824 | A1 | 9/1982 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72762 | A1 | 12/2000 |
| WO | WO 94/12108 | A1 | 6/1994 | WO | WO 00/72765 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/54594 | A1 | 8/2001 |
| WO | WO 95/06817 | A1 | 3/1995 | WO | WO 01/58371 | A1 | 8/2001 |
| WO | WO 95/09576 | A1 | 4/1995 | WO | WO 01/62158 | A2 | 8/2001 |
| WO | WO 95/09577 | A1 | 4/1995 | WO | WO 01/62161 | A1 | 8/2001 |
| WO | WO 95/14436 | A1 | 6/1995 | WO | WO 01/62162 | A1 | 8/2001 |
| WO | WO 95/17855 | A1 | 7/1995 | WO | WO 01/62164 | A2 | 8/2001 |
| WO | WO 95/18383 | A1 | 7/1995 | WO | WO 01/62169 | A2 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A2 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A1 | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |
| WO | WO 96/39088 | A1 | 12/1996 | WO | WO 03/079909 | A3 | 3/2003 |
| WO | WO 96/39089 | A1 | 12/1996 | WO | WO 03/030743 | A2 | 4/2003 |
| WO | WO 97/00646 | A1 | 1/1997 | WO | WO 03/037193 | A1 | 5/2003 |
| WO | WO 97/00647 | A1 | 1/1997 | WO | WO 03/047436 | A3 | 6/2003 |
| WO | WO 97/06582 | A1 | 2/1997 | WO | WO 03/055402 | A1 | 7/2003 |
| WO | WO 97/10763 | A1 | 3/1997 | WO | WO 03/057048 | A1 | 7/2003 |
| WO | WO 97/10764 | A1 | 3/1997 | WO | WO 03/057058 | A1 | 7/2003 |
| WO | WO 97/11648 | A2 | 4/1997 | WO | WO 03/063694 | A1 | 8/2003 |
| WO | WO 97/11649 | A1 | 4/1997 | WO | WO 03/077769 | A1 | 9/2003 |
| WO | WO 97/15237 | A1 | 5/1997 | WO | WO 03/079911 | A1 | 10/2003 |
| WO | WO 97/24073 | A1 | 7/1997 | WO | WO 03/082126 | A1 | 10/2003 |
| WO | WO 97/24993 | A1 | 7/1997 | WO | WO 03/088845 | A2 | 10/2003 |
| WO | WO 97/30644 | A1 | 8/1997 | WO | WO 03/090630 | A2 | 11/2003 |
| WO | WO 97/34533 | A1 | 9/1997 | WO | WO 03/094743 | A1 | 11/2003 |
| WO | WO 97/37598 | A1 | 10/1997 | WO | WO 03/094745 | A1 | 11/2003 |
| WO | WO 97/39688 | A2 | 10/1997 | WO | WO 03/094746 | A1 | 11/2003 |
| WO | WO 98/17180 | A1 | 4/1998 | WO | WO 03/094747 | A1 | 11/2003 |
| WO | WO 98/27880 | A1 | 7/1998 | WO | WO 03/101313 | A1 | 12/2003 |
| WO | WO 98/30153 | A1 | 7/1998 | WO | WO 03/105698 | A2 | 12/2003 |
| WO | WO 98/47436 | A1 | 10/1998 | WO | WO 03/105702 | A2 | 12/2003 |
| WO | WO 99/03407 | A1 | 1/1999 | WO | WO 2004/006980 | A2 | 1/2004 |
| WO | WO 99/03408 | A1 | 1/1999 | WO | WO 2004/011037 | A2 | 2/2004 |
| WO | WO 99/03409 | A1 | 1/1999 | WO | WO 2004/019769 | A1 | 3/2004 |
| WO | WO 99/12483 | A1 | 3/1999 | WO | WO 2004/021868 | A2 | 3/2004 |
| WO | WO 99/12487 | A1 | 3/1999 | WO | WO 2004/028585 | A2 | 4/2004 |
| WO | WO 99/12488 | A1 | 3/1999 | WO | WO 2004/032754 | A2 | 4/2004 |
| WO | WO 99/15086 | A1 | 4/1999 | WO | WO 2004/032760 | A2 | 4/2004 |
| WO | WO 99/15091 | A1 | 4/1999 | WO | WO 2004/032762 | A1 | 4/2004 |
| WO | WO 99/23933 | A2 | 5/1999 | WO | WO 2004/032763 | A2 | 4/2004 |
| WO | WO 99/23959 | A1 | 5/1999 | WO | WO 2004/034875 | A2 | 4/2004 |

| | | | |
|---|---|---|---|
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2010/063795 A1 | 6/2010 |
| WO | WO 2012/044844 A2 | 4/2012 |

OTHER PUBLICATIONS

U.S. Appl. No. 12/031,580, filed Feb. 14, 2008.
U.S. Appl. No. 12/031,368, filed Feb. 14, 2008.
U.S. Appl. No. 12/031,542, filed Feb. 14, 2008.
U.S. Appl. No. 12/031,556, filed Feb. 14, 2008.
U.S. Appl. No. 12/031,573, filed Feb. 14, 2008.
U.S. Appl. No. 13/118,241, filed May 27, 2011.
The Sodem Aseptic Battery Transfer Kit, Sodem Systems, 2000, 3 pages.
U.S. Appl. No. 12/366,548, filed Feb. 5, 2009.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
International Search Report for PCT/US2010/022321 included in PCT Publication WO 2010/090931, dated Mar. 16, 2010 (132 pages).
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
International Search Report for PCT/US2010/057101, dated May 25, 2011 (7 pages).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
U.S. Appl. No. 13/488,903, filed Jun. 5, 2012.
U.S. Appl. No. 13/310,107, filed Dec. 2, 2011.
U.S. Appl. No. 13/369,561, filed Feb. 9, 2012.
U.S. Appl. No. 13/369,569, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/372,195, filed Feb. 13, 2012.
U.S. Appl. No. 13/486,175, filed Jun. 1, 2012.
U.S. Appl. No. 13/480,263, filed May 24, 2012.

* cited by examiner

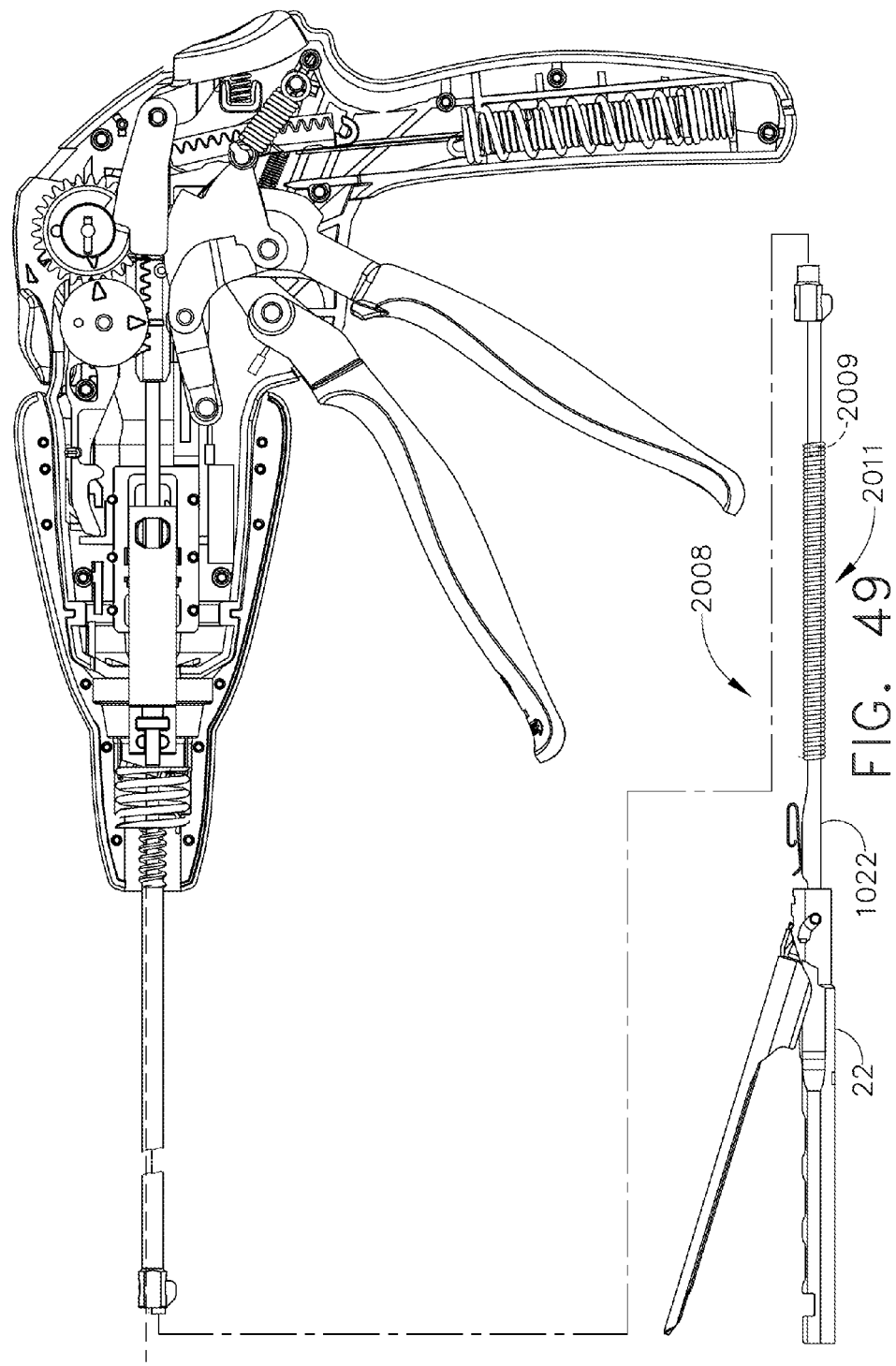

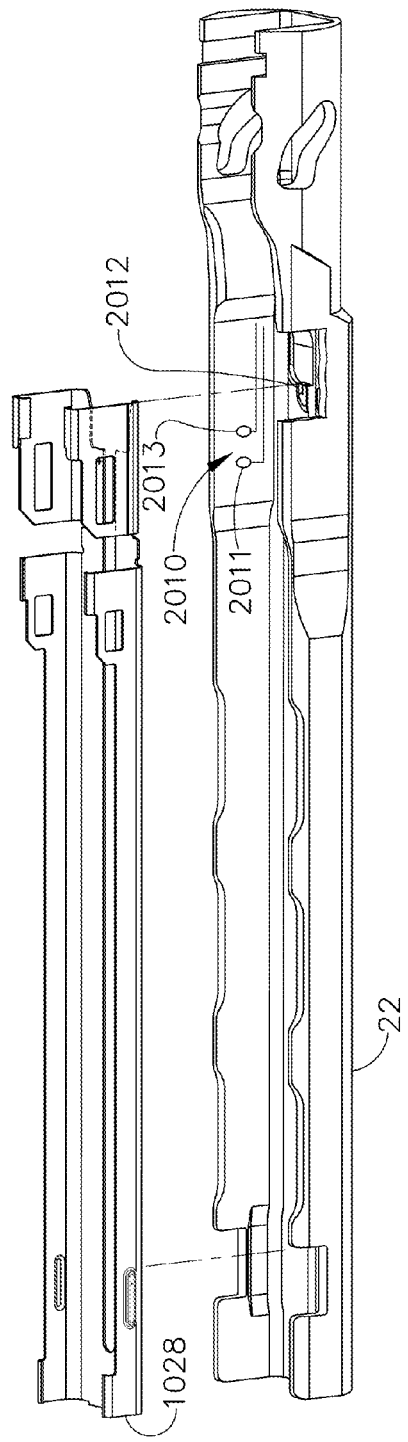
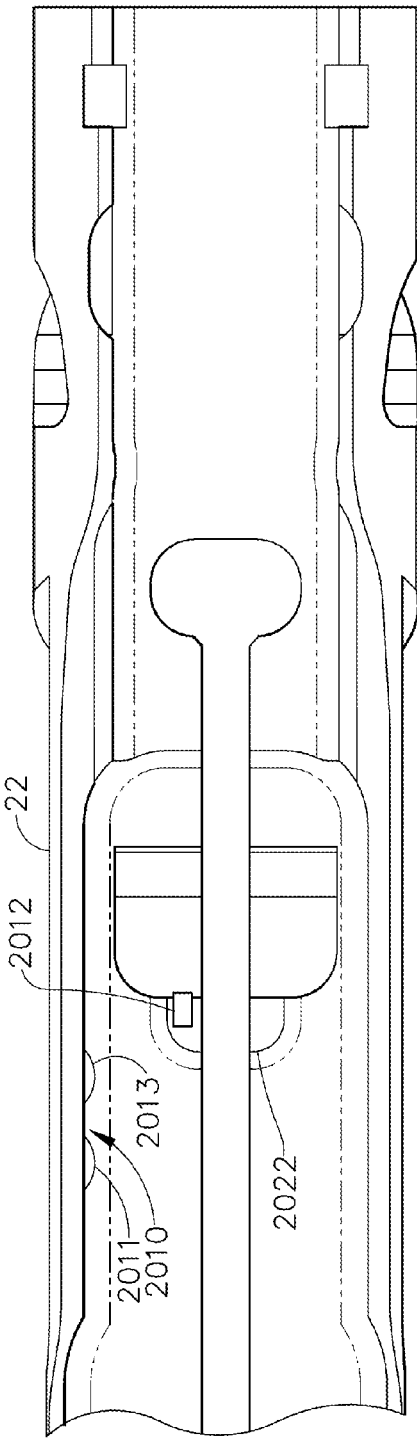

| EVENT # | CLOSURE LOAD | FIRING STROKE | FIRING LOAD (MAX) | KNIFE POSITION % | LOCKOUTS ANVIL CLOSED/OPEN | LOCKOUT MEMORY IS YES NO | SLED PRESENT YES/NO | CARTRIDGE PRESENT YES/NO |
|---|---|---|---|---|---|---|---|---|
| 1 | 10 | | | | 0 | | | 1 |
| 2 | 12 | | | | 0 | | | 1 |
| 3 | 15 | | | | 0 | | | 1 |
| 4 | 50 | | | | 1 | | | 1 |
| 25 | 25 | 1 | 250 | .33 | 1 | | 0 | 1 |
| 26 | 100 | 2 | 400 | .66 | 1 | | 0 | 1 |
| 27 | 120 | 3 | 200 | .75 | 1 | | 0 | 1 |
| 55 | 50 | | | | 1 | | 0 | 1 |
| 56 | 50 | | | | 1 | | 0 | 1 |

EXAMPLE: 3 STEP FIRING

FIG. 53

SURGICAL INSTRUMENTS AND COMPONENTS FOR USE IN STERILE ENVIRONMENTS

PRIORITY

The present disclosure is a continuation-in-part application claiming priority under 35 U.S.C. §120 from co-pending U.S. patent application Ser. No. 12/366,548, now U.S. Publication No. 2010/0193569 A1, entitled STERILIZABLE SURGICAL INSTRUMENT, filed on Feb. 5, 2009, the entire disclosure of which is hereby incorporated by reference herein.

FIELD

The present disclosure relates, in general, to surgical instruments suitable for use in sterile environments and, more particularly, to surgical instruments having a first portion and a second portion, wherein the first portion, in one embodiment, is encapsulated by a membrane such that it can be engaged with the second portion and used in a sterile environment. The present disclosure also relates to electronic components suitable for use in a sterile environment.

BACKGROUND

After a surgical instrument has been manufactured, and/or after a surgical instrument has been used during a surgical procedure, the surgical instrument can be subjected to physical sterilization and/or chemical sterilization in order to kill or eliminate transmissible agents thereon. Physical sterilization can include gamma radiation sterilization which can be suitable in many circumstances. In some circumstances, however, gamma radiation can damage the electronic components and/or power source, for example, of a surgical instrument. As a result, the options available to sterilize such surgical instruments can be limited to heat or steam sterilization and/or chemical sterilization, such as ethylene oxide, ozone, and/or hydrogen peroxide, for example. While such options are suitable in many circumstances, they may be more expensive and/or time-consuming to perform as compared gamma radiation sterilization, for example. In other instances, the electronic components and/or the power source may not be subjected to sterilization to a level in which they can be openly exposed in an operating room during a surgical procedure. What is needed is an improvement over the foregoing.

The foregoing discussion is intended only to illustrate some of the shortcomings present in the field of the disclosure at the time, and should not be taken as a disavowal of claim scope.

SUMMARY

In one general aspect of the present disclosure, a surgical instrument can comprise a first portion, such as a power source, for example, comprising at least one first electrical contact, a membrane encapsulating the first portion, and a second portion. The second portion can comprise a surgical instrument body and a wall defining a cavity in the surgical instrument body. The cavity can be configured to at least partially receive the first portion while the first portion remains encapsulated by the membrane. The second portion can further comprise a first region comprising at least one second electrical contact, a second region comprising an opening in communication with the cavity, and a closure member movable between a first position and a second position. The closure member can be in sealable engagement with the second region when it is in the first position and can be at least partially free from sealable engagement with the second region when it is in the second position. The first electrical contact and/or the second electrical contact can be configured to penetrate the membrane to allow an electrical connection to be made between the first portion and the second portion at least when the closure member moves from the second position into the first position.

In another general aspect of the present disclosure, a surgical instrument system can comprise a first portion comprising at least one first electrical terminal and a sealed package. The first portion can be positioned within the sealed package and the sealed package can comprises a microbe impermeable barrier layer. The surgical instrument system can further comprise a second portion comprising a surgical instrument body and a receiving slot defined in the surgical instrument body. The receiving slot can be configured to receive at least part of the first portion while the first portion is positioned within the sealed package. The second portion can further comprise a first region comprising at least one second electrical terminal, a second region defining a passage into the receiving slot, and a closure member movable between a first position and a second position. The closure member can be in sealable contact with the second region when it is in the first position and can be at least partially free from sealable contact with the second region when it is in the second position. The closure member can comprise a camming surface configured to force the first portion into the receiving slot and configured to cause one of the first electrical terminal and the second electrical terminal to pierce the sealed package to allow and electrical connection to be made between the first portion and the second portion at least when the closure member moves from the second position into the first position.

In yet another general aspect of the present disclosure, an electronic component assembly can be configured to be placed in electrical communication with a surgical instrument. The electronic component assembly can comprise an electronic component configured to power and/or control the surgical instrument when the electronic component assembly is placed in electrical communication with the surgical instrument. A housing can surround the electronic component. The housing can comprise an outer surface comprising a material configured to at least resist microbial contamination, at least one vent defined in the housing, and a gas permeable, microbe impermeable barrier positioned over the at least one vent and configured to at least inhibit microbe egress from the housing.

In still another general aspect of the present disclosure, a surgical instrument module can comprise an electronic component configured to at least one of power and control a surgical instrument when the surgical instrument module is situated in electrical communication with the surgical instrument. A housing can encapsulate the electronic component. The housing can comprise an outer surface comprising a first antimicrobial material, at least one vent formed in the housing, and a gas permeable, microbe impermeable barrier positioned over the at least one vent. The gas permeable, microbe impermeable barrier can be configured to prevent microbes on the electronic component from exiting the housing while allowing a gas to flow into and out of the housing. The surgical instrument module can further comprise a fin attached to the housing and extending away from the electronic component. The fin can be configured to dissipate heat created by the electronic component and can comprise a second antimicrobial material.

This Summary is intended to briefly outline certain embodiments of the present disclosure. It should be understood that the present disclosure is not limited to the embodiments disclosed in this Summary, and is intended to cover modifications that are within its spirit and scope, as defined by the claims. It should be further understood that this Summary should not be read or construed in a manner that will act to narrow the scope of the claims.

BRIEF DESCRIPTION OF THE DRAWINGS

The above-mentioned and other features and advantages of the disclosure, and the manner of attaining them, will become more apparent and the disclosure itself will be better understood by reference to the following description of embodiments of the disclosure taken in conjunction with the accompanying drawings, wherein:

FIG. 49 illustrates a side view of the handle, end effector, and firing bar of the instrument of FIG. 42 showing a sensor;

FIG. 50 illustrates an exploded view of the staple channel and portions of a staple cartridge of the instrument showing various sensors according to various embodiments of the present invention;

FIG. 51 illustrates a top down view of the staple channel of the instrument of FIG. 42 showing various sensors;

FIG. 53 illustrates a memory chart showing exemplary recorded conditions of a surgical instrument according to various embodiments;

Corresponding reference characters indicate corresponding parts throughout the several views. The exemplifications set out herein illustrate preferred embodiments of the disclosure, in one form, and such exemplifications are not to be construed as limiting the scope of the disclosure in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present disclosure is defined solely by the claims. The features illustrated or described in connection with one exemplary embodiment may be combined with the features of other embodiments. Such modifications and variations are intended to be included within the scope of the present disclosure.

Figure 1:
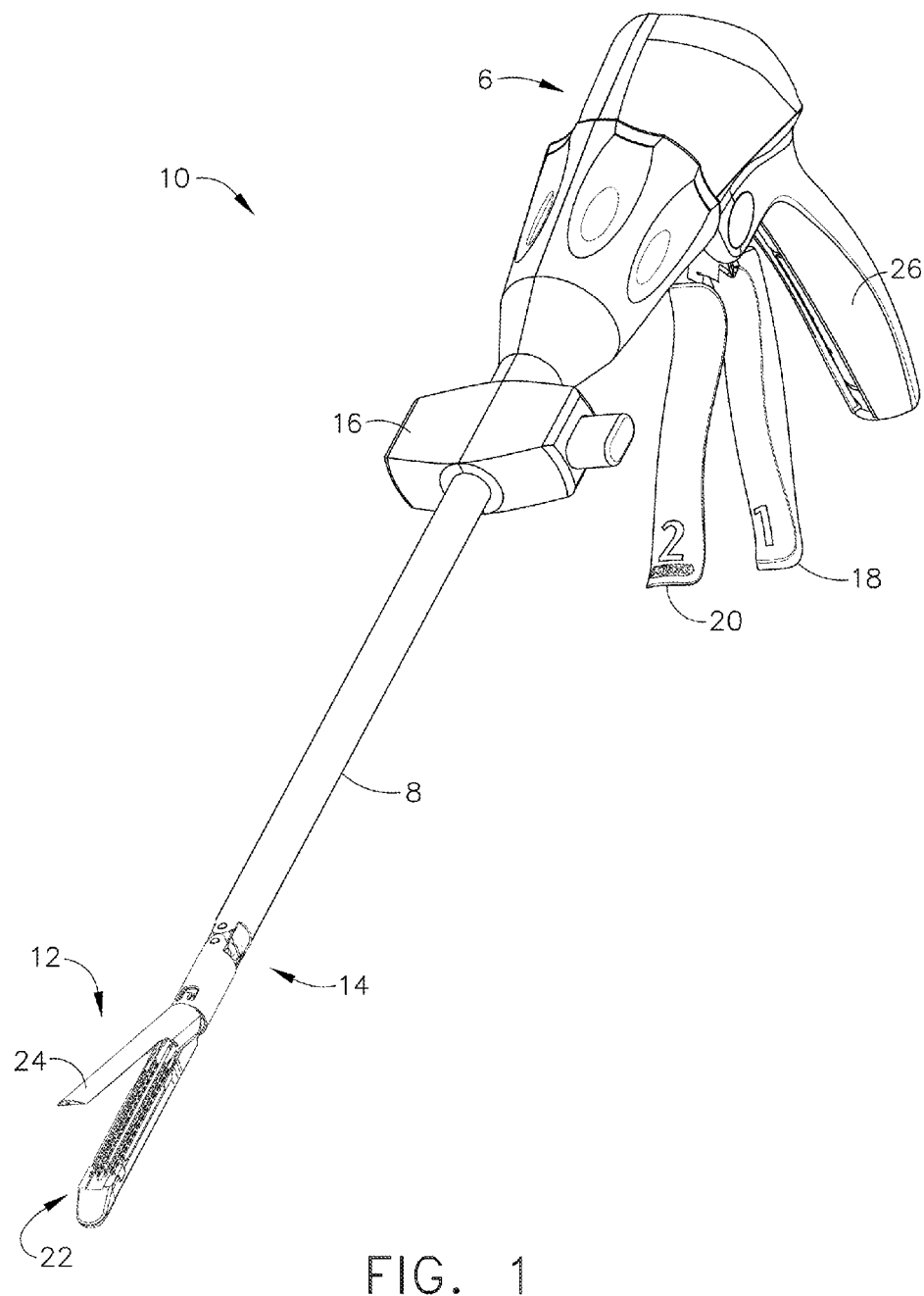
FIGS. 1 and 2 are perspective views of a surgical cutting and fastening instrument.
Figure 2:
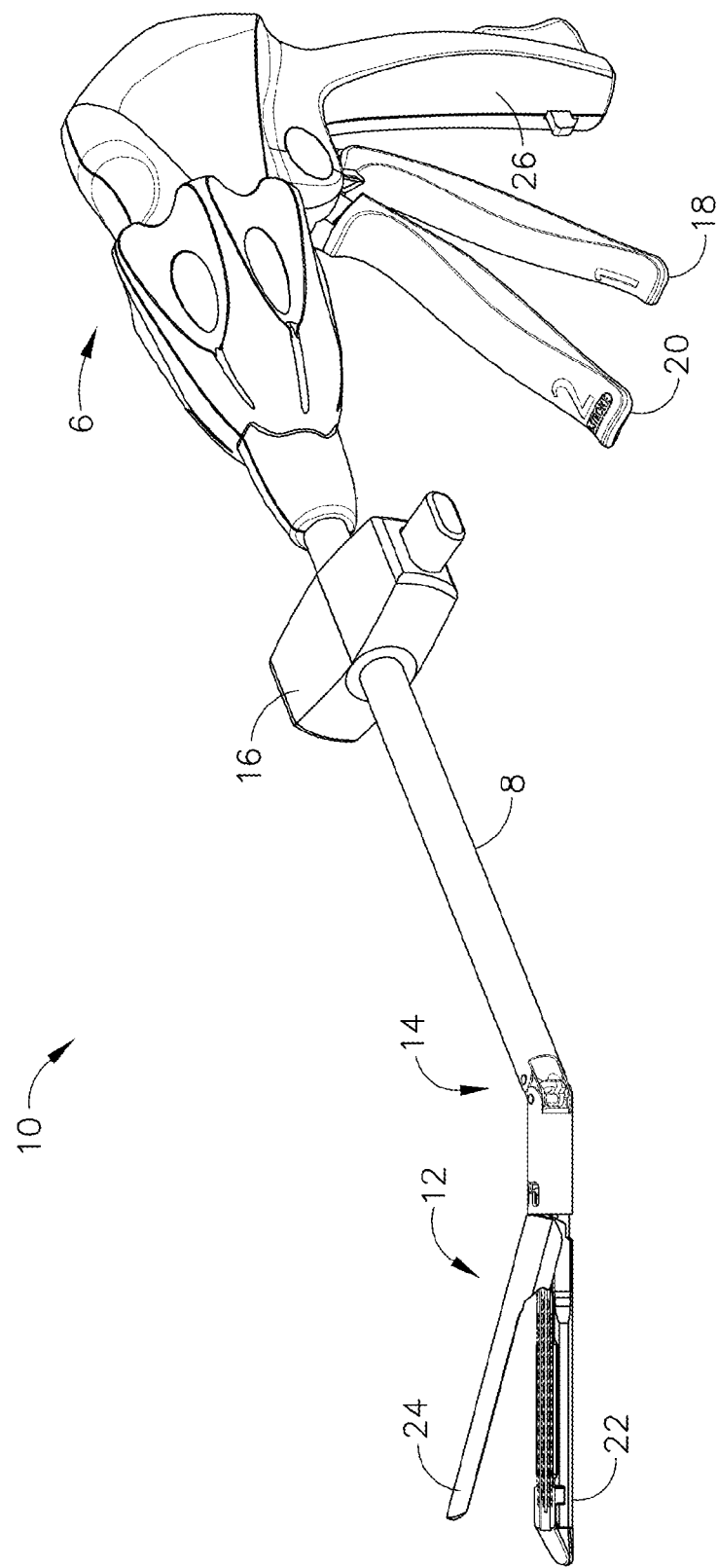

FIGS. 1 and 2 depict a surgical cutting and fastening instrument 10 according to various embodiments. The illustrated embodiment is an endoscopic surgical instrument 10 and in general, the embodiments of the instrument 10 described herein are endoscopic surgical cutting and fastening instruments. It should be noted, however, that according to other embodiments, the instrument 10 may be a non-endoscopic surgical cutting instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. It will be appreciated that various embodiments may include a non-pivoting end effector, and therefore may not have an articulation pivot 14 or articulation control 16. Also, in the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled SURGICAL INSTRUMENT HAVING AN ARTICULATING END EFFECTOR, the entire disclosure of which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 toward which a closure trigger 18 is pivotally drawn by the clinician to cause clamping or closing of the anvil 24 towards the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, release button 30 shown in FIGS. 42-43, slide release button 160 shown in FIG. 14, and/or button 172 shown in FIG. 16.

Figure 3:
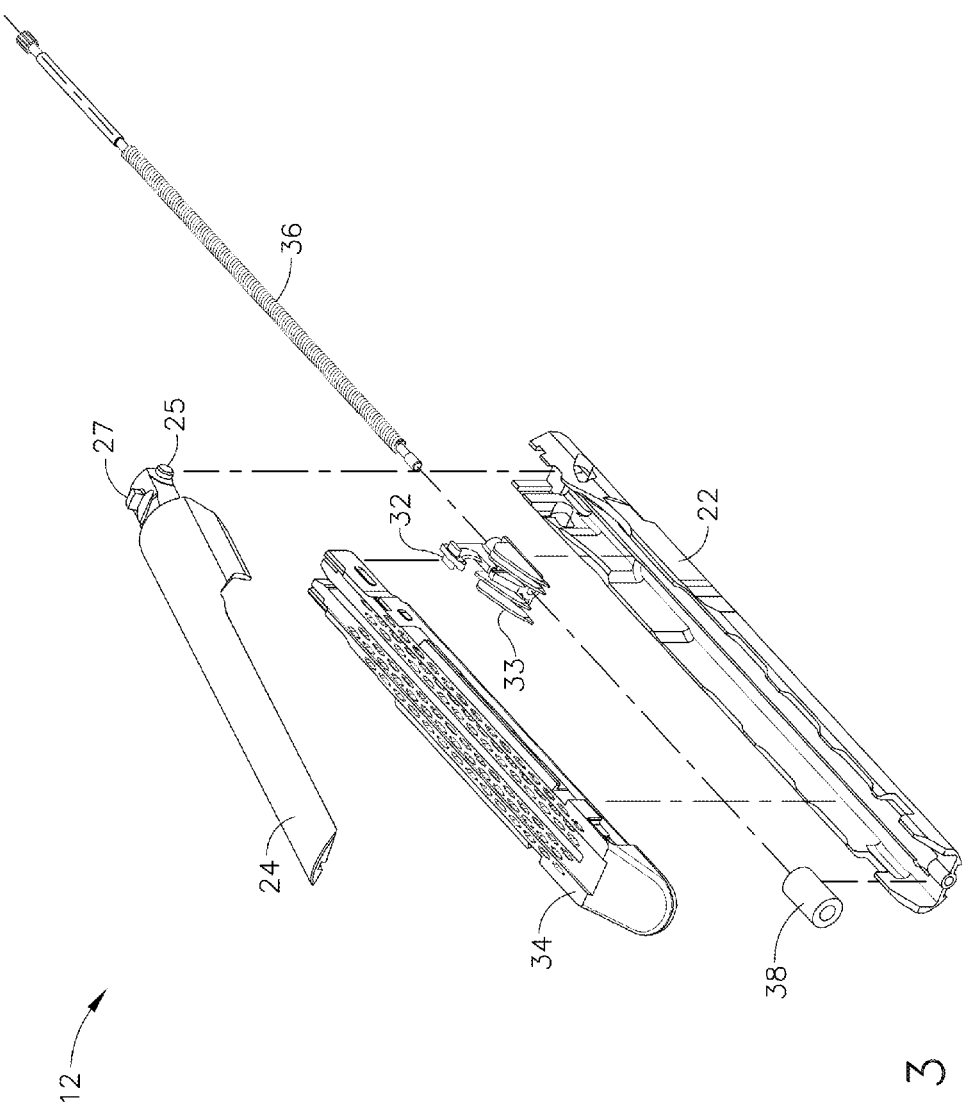
FIGS. 3-5 are exploded views of an end effector and shaft of the instrument of FIG. 1.

FIGS. 3-6 show embodiments of a rotary-driven end effector 12 and shaft 8 according to various embodiments. FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at pivot pins 25 connected to the proximal end of the channel 22. The anvil 24 may also include a tab 27 at its proximal end that is inserted into a component of the mechanical closure system (described further below) to open and close the anvil 24. When the closure trigger 18 is actuated, that is, drawn in by a user of the instrument 10, the anvil 24 may pivot about the pivot pins 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples (not shown) of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled SURGICAL STAPLING INSTRUMENT INCORPORATING AN E-BEAM FIRING MECHANISM, the entire disclosure of which is incorporated herein by reference, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled ELECTROSURGICAL HEMOSTATIC DEVICE, and U.S. Pat. No. 5,688,270, entitled ELECTROSURGICAL HEMOSTATIC DEVICE WITH RECESSED AND/OR OFFSET ELECTRODES, the entire disclosures of which are incorporated herein by reference, disclose an endoscopic cutting instrument that uses RF energy to seal the severed tissue. U.S. patent application Ser. No. 11/267,811, entitled SURGICAL STAPLING INSTRUMENTS STRUCTURED FOR DELIVERY OF MEDICAL AGENTS, and U.S. patent application Ser. No. 11/267,383, entitled SURGICAL STAPLING INSTRUMENTS STRUCTURED FOR PUMP-ASSISTED DELIVERY OF MEDICAL AGENTS, the entire disclosures of which are also incorporated herein by reference, disclose cutting instruments that uses adhesives to fasten the severed tissue. Accordingly, although the description herein refers to cutting/stapling operations and the like below, it should be recognized that this is an exemplary embodiment and is not meant to be limiting. Other tissue fastening techniques may also be used.

Figure 4:
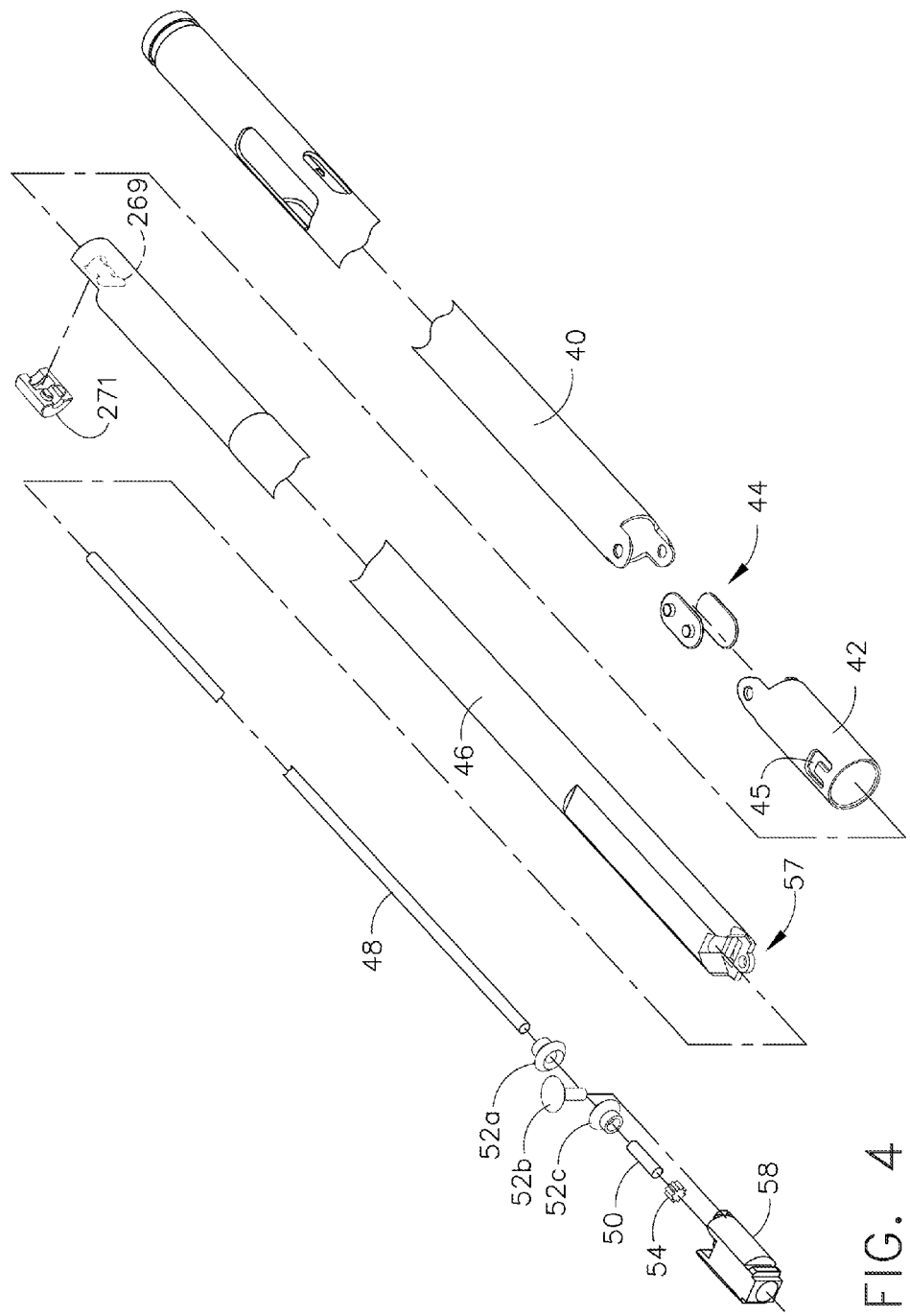
Figure 5:
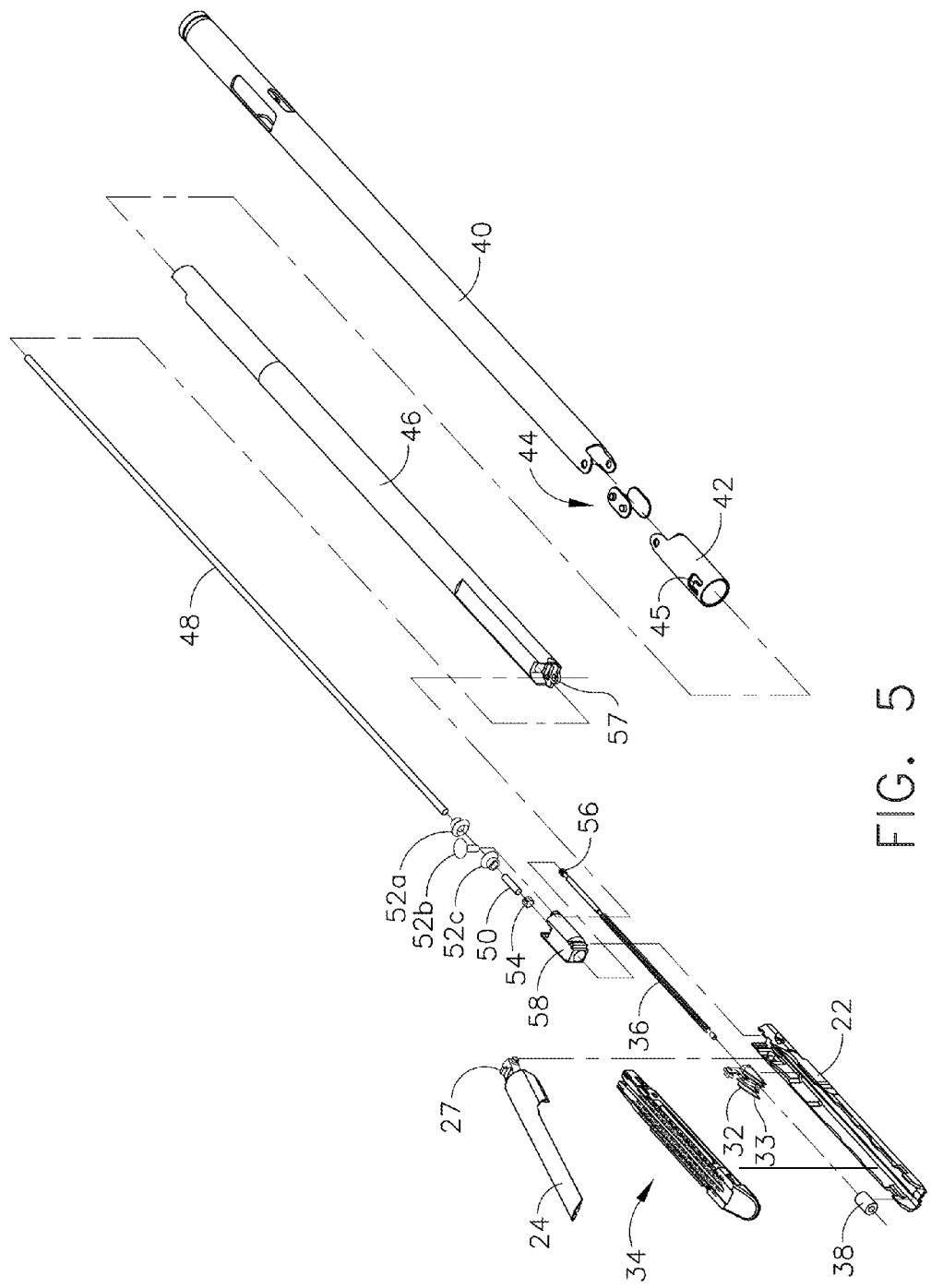
Figure 6:
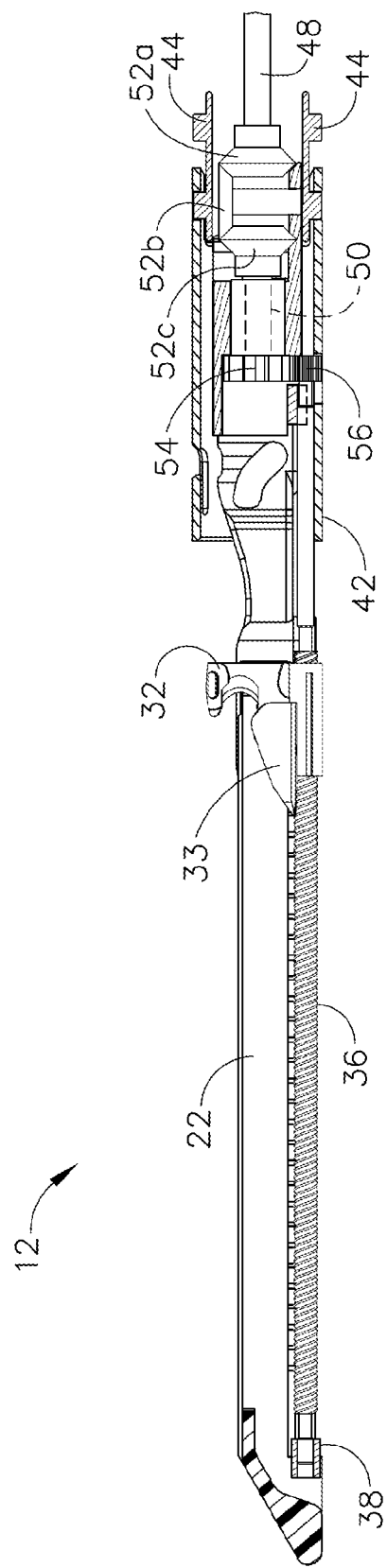
FIG. 6 is a side view of the end effector of FIG. 3.
Figure 7:
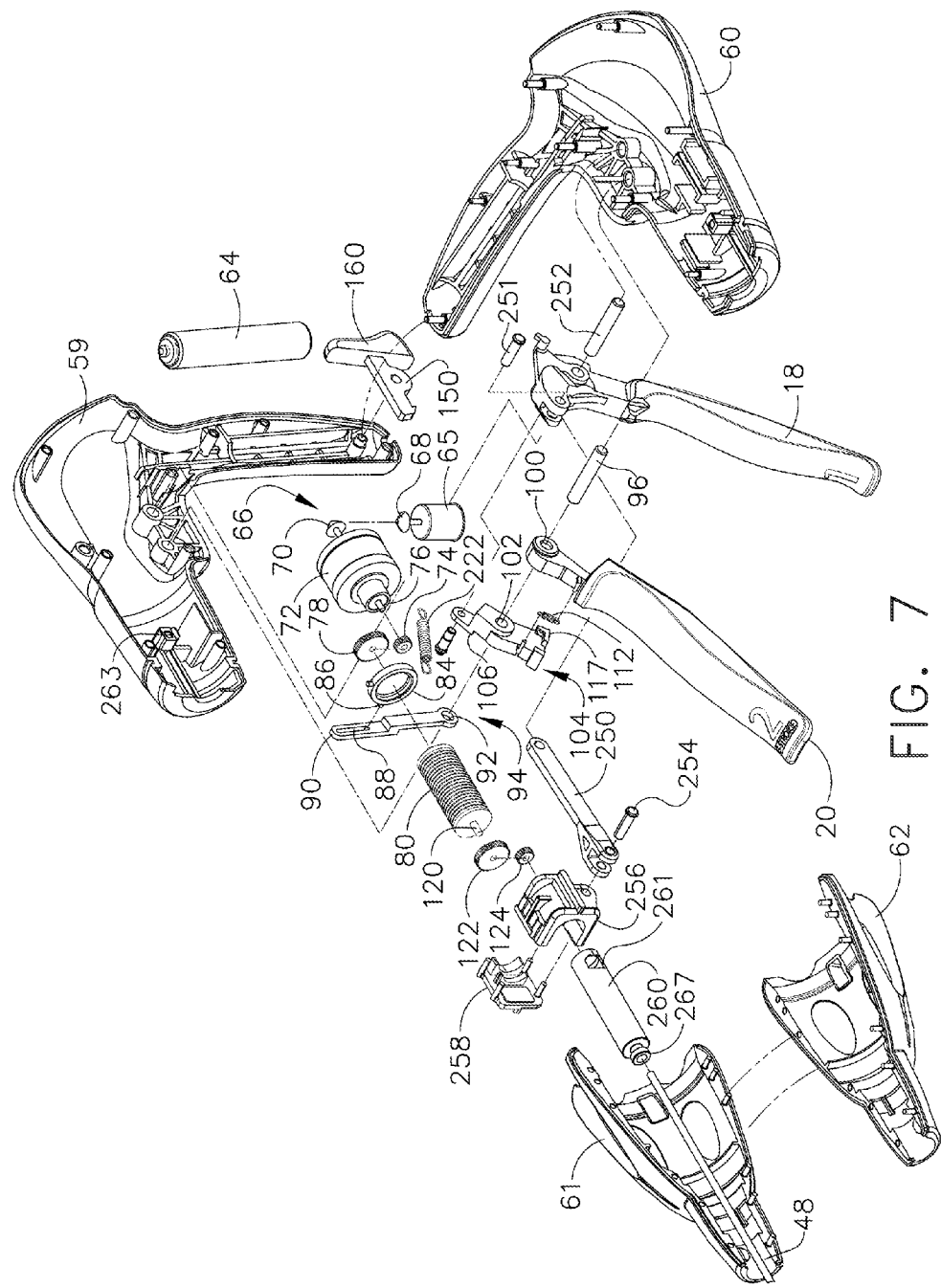
FIG. 7 is an exploded view of the handle of the instrument of FIG. 1.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot link 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52a-c. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector 12. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

In certain circumstances, there is a general lack of acceptance among physicians of motor-driven endocutters where the cutting/stapling operation is actuated by merely pressing a button because of the lack of user feedback for the cutting/stapling operation. In contrast, certain embodiments disclosed herein provide a motor-driven endocutter with user-feedback of the deployment, force and/or position of the cutting instrument 32 in end effector 12.

FIGS. 7-10 illustrate an exemplary embodiment of a motor-driven endocutter, and in particular the handle thereof, that provides user-feedback regarding the deployment and loading force of the cutting instrument 32 in the end effector 12. In addition, the embodiment may use power provided by the user in retracting the firing trigger 20 to power the device (a so-called "power assist" mode). The embodiment may be used with the rotary driven end effector 12 and shaft 8 embodiments described above. As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 (see FIG. 10) in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 110, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor sensor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximal end of the helical gear drum 80 so that the ring 84 trips the switch 142 when the ring 84 reaches the proximal end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65, for example, at a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector 12 is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximal end of the helical gear drum 80.

Figure 8:
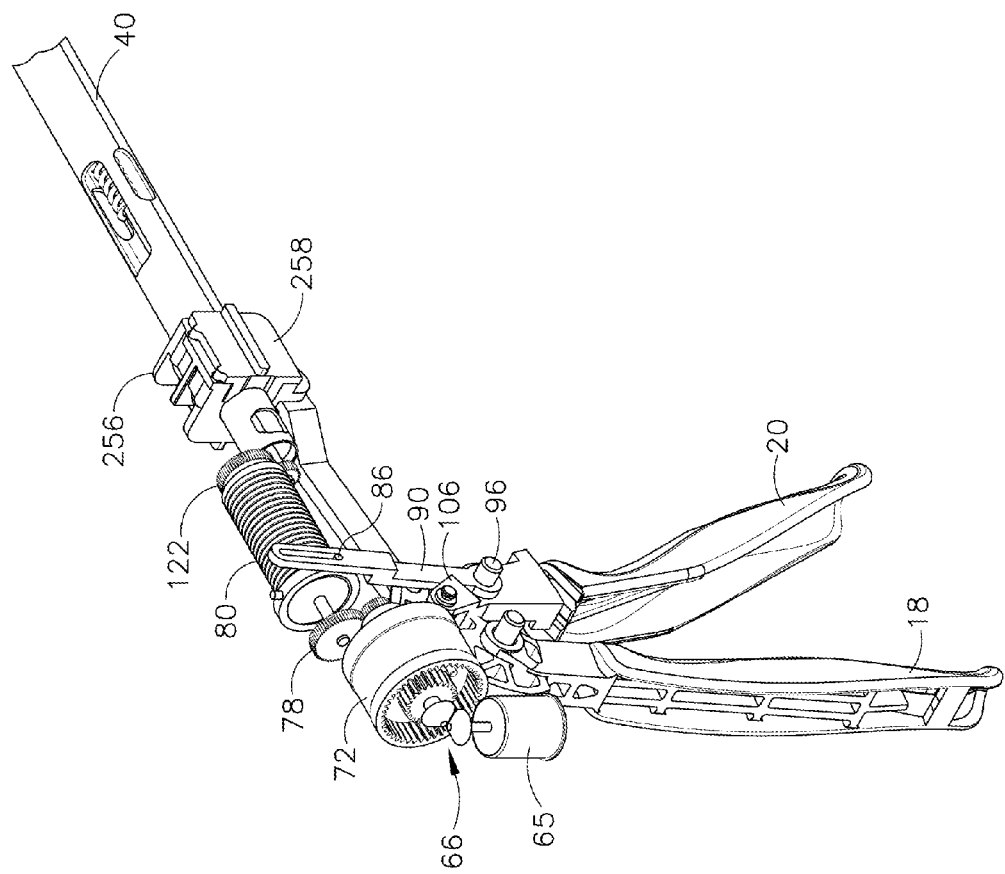
FIGS. 8 and 9 are partial perspective views of the handle of FIG. 1.
Figure 9:
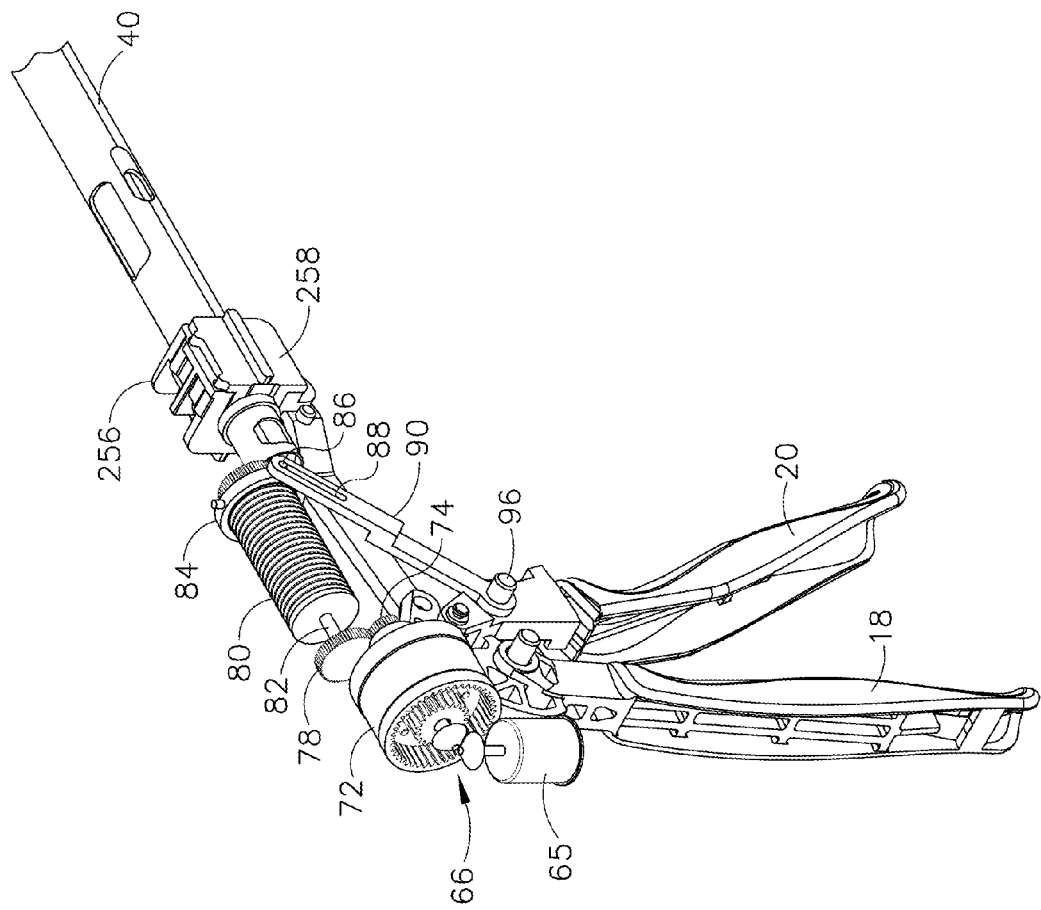

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates counter clockwise as the ring 84 travels from the proximal end of the helical gear drum 80 to the distal end, the middle handle piece 104 will be free to rotate counter clockwise. Thus, as the user draws in the firing trigger 20, the firing trigger 20 will engage the forward motion stop 107 of the middle handle piece 104, causing the middle handle piece 104 to rotate counter clockwise. Due to the backside shoulder 106 engaging the slotted arm 90, however, the middle handle piece 104 will only be able to rotate counter clockwise as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate counter clockwise due to the slotted arm 90.

Figure 10:
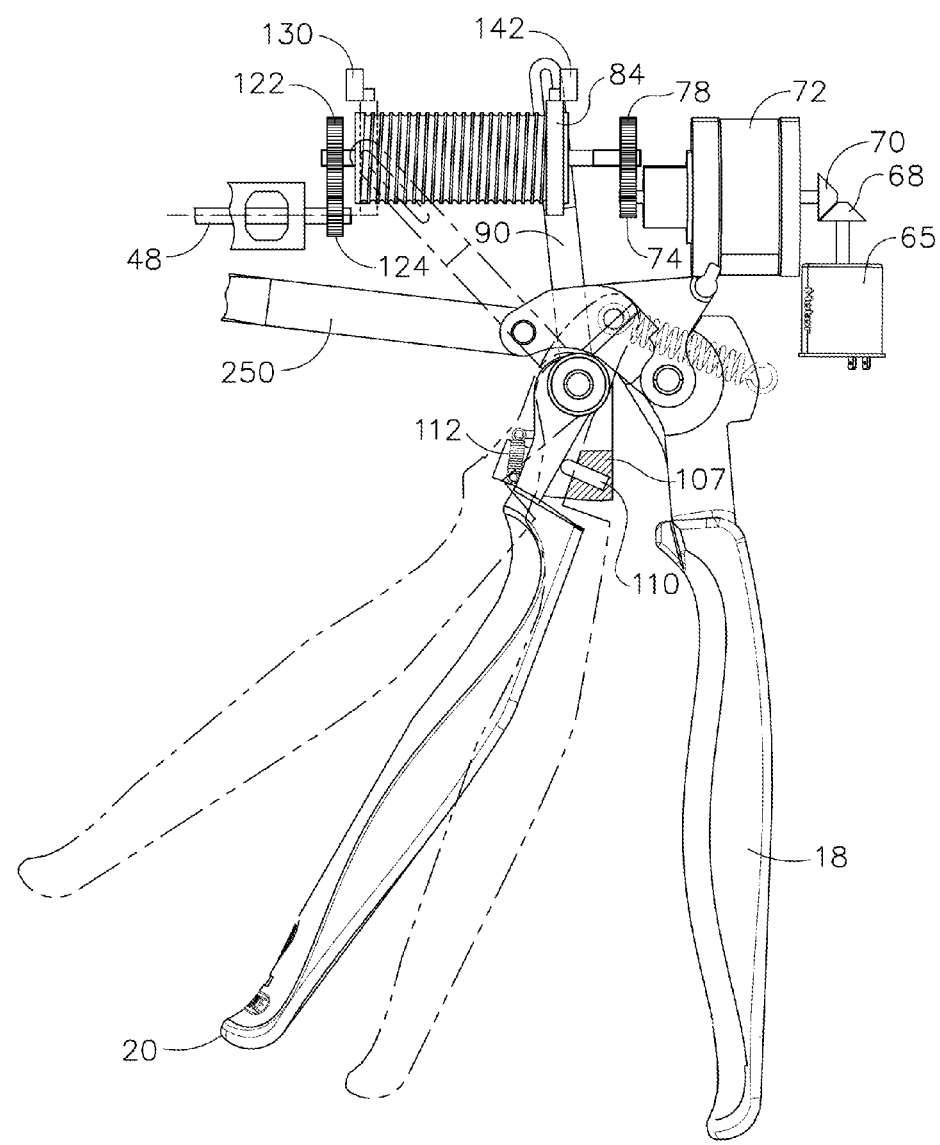
FIG. 10 is a side view of the handle of FIG. 1.
Figure 10A:
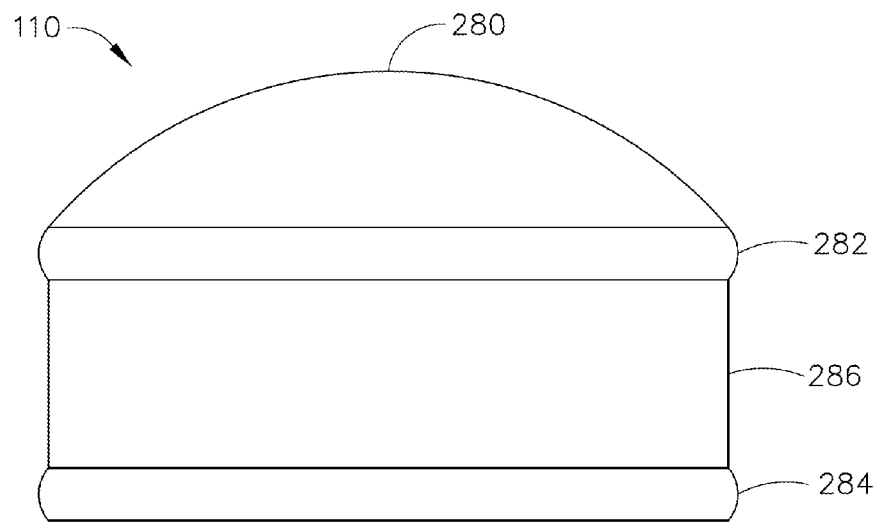
FIGS. 10A and 10B illustrate a proportional sensor that may be used with the handle of FIG. 1.
Figure 10B:
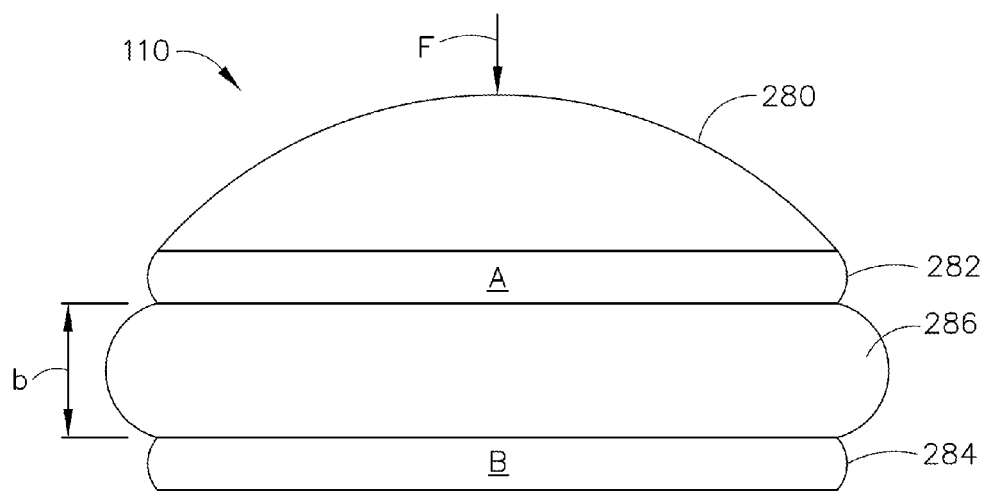

FIGS. 10A and 10B illustrate two states of a variable sensor that may be used as the run motor sensor 110. The sensor 110 may include a face portion 280, a first electrode (A) 282, a second electrode (B) 284, and a compressible dielectric material 286 between the electrodes 282, 284, such as, for example, an electroactive polymer (EAP). The sensor 110 may be positioned such that the face portion 280 contacts the firing trigger 20 when retracted. Accordingly, when the firing trigger 20 is retracted, the dielectric material 286 is compressed, as shown in FIG. 10B, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric 286 is compressed due to retraction of the firing trigger 20 (denoted as force "F" in FIG. 42) is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pivot pin 251 inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate counterclockwise. The distal end of the yoke 250 is connected, via a pin 254, to a first closure bracket 256. The first closure bracket 256 connects to a second closure bracket 258. Collectively, the closure brackets 256, 258 define an opening in which the proximal end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot pins 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot pins 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
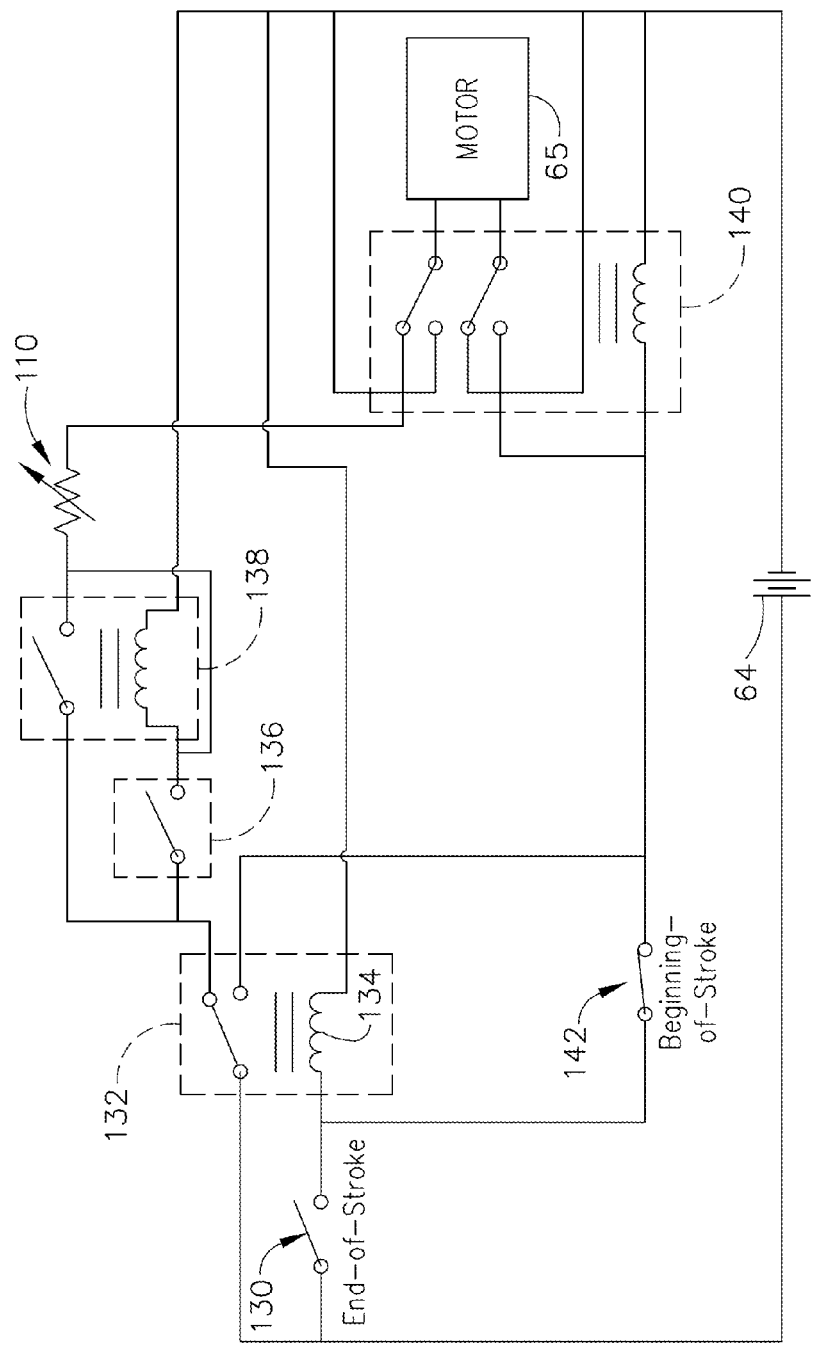
FIG. 11 is a schematic diagram of a circuit used in the instrument of FIG. 1.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 134. This causes the relay 134 to assume its energized state (not shown in FIG. 13), which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction.

Because the stop motor sensor switch 142 is normally-closed, current will flow back to the relay 134 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
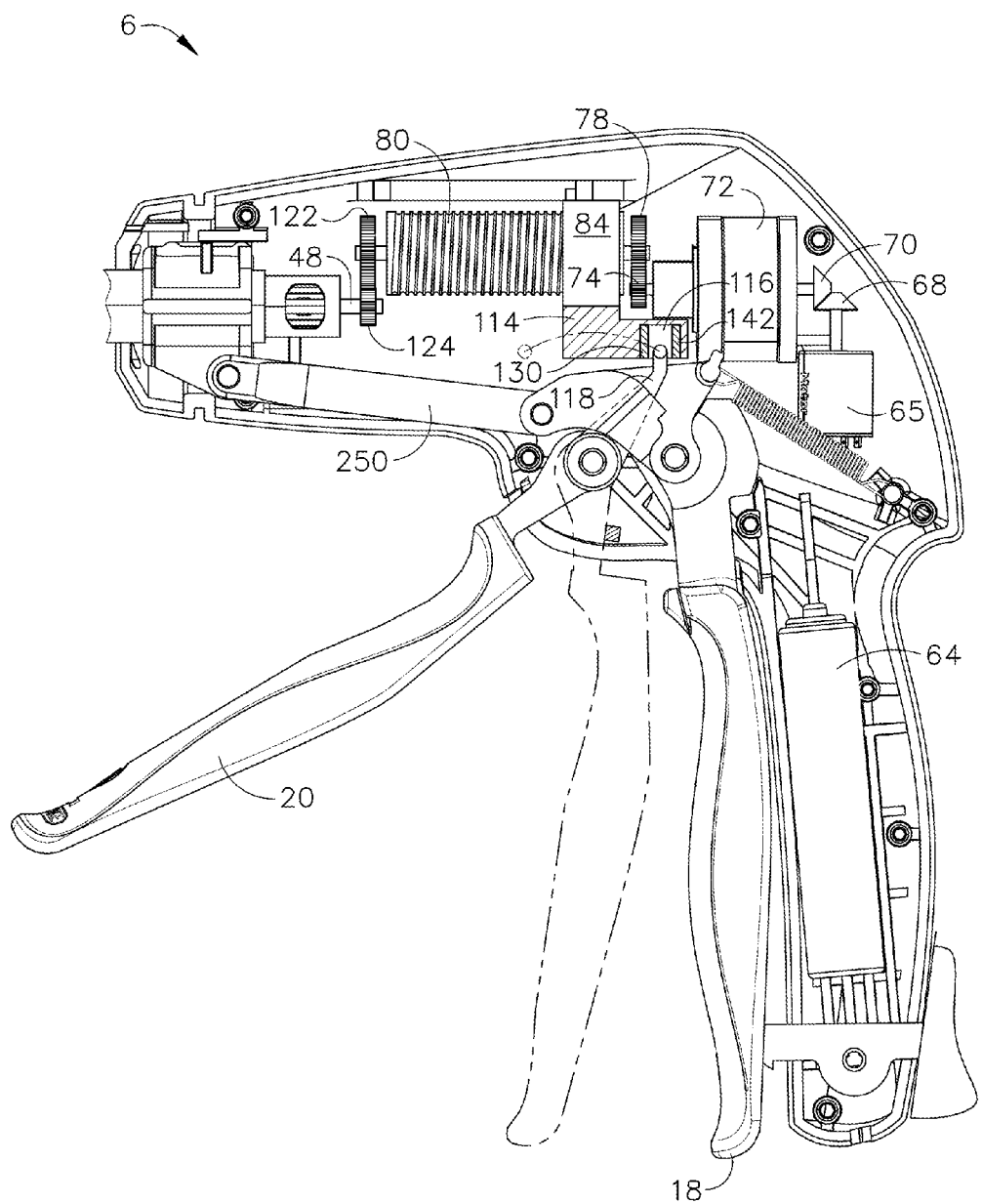
FIGS. 12-13 are side views of a surgical instrument handle according to other embodiments.

FIG. 12 is a side-view of the handle 6 of a power-assist motorized endocutter according to another embodiment. The embodiment of FIG. 12 is similar to that of FIGS. 7-10 except that in the embodiment of FIG. 12, there is no slotted arm connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximal end of the notch 116. As the ring 84 moves down the helical gear drum 80 (and back), the sensor portion 114 moves with it. Further, as shown in FIG. 12, the middle piece 104 may have an arm 118 that extends into the notch 12.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate counter clockwise with the firing trigger 20 due to the forward motion stop 107 that engages the firing trigger 20. The counter clockwise rotation of the middle piece 104 cause the arm 118 to rotate counter clockwise with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximal end of the helical gear drum 80, the arm will contact and thereby trip the stop motor sensor 142. Such actions may reverse and stop the motor 65, respectively as described above.

Figure 13:
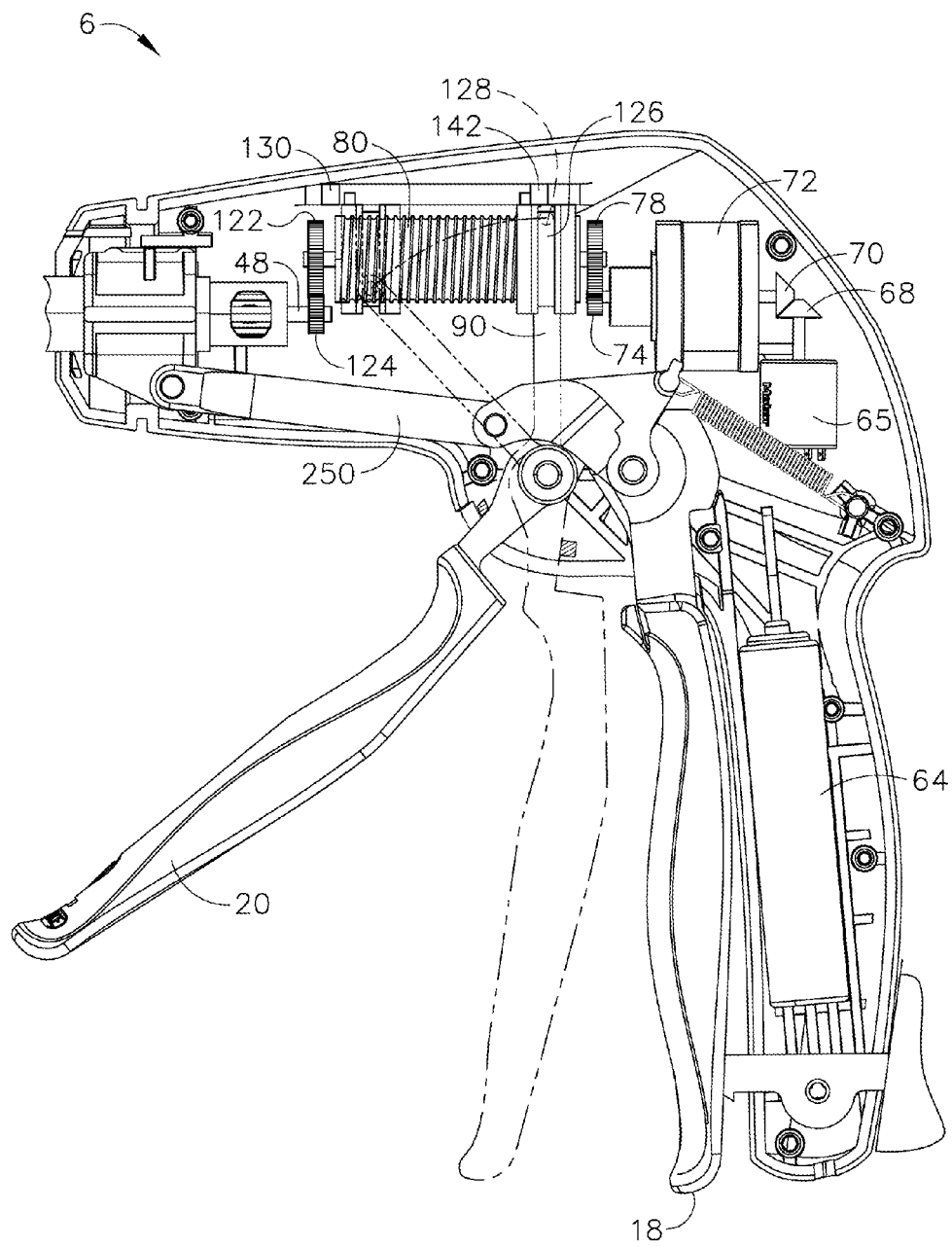

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90. Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates counter clockwise as the ring 84 advances due to the post 128 being disposed in the channel 126, as shown in FIG. 13.

Figure 14:
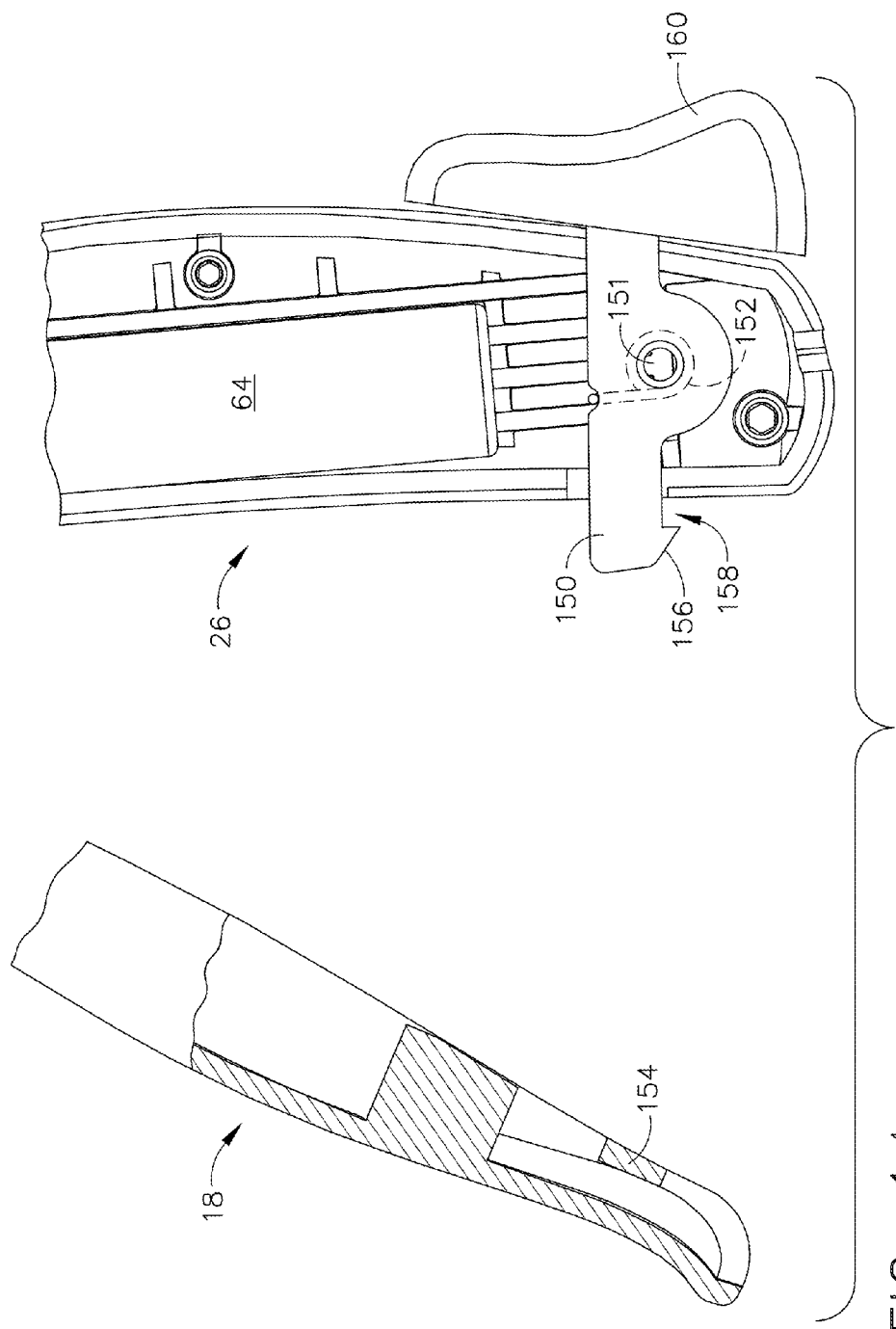
FIGS. 14-22 illustrate different mechanisms for locking a closure trigger of a surgical instrument handle.
Figure 15:
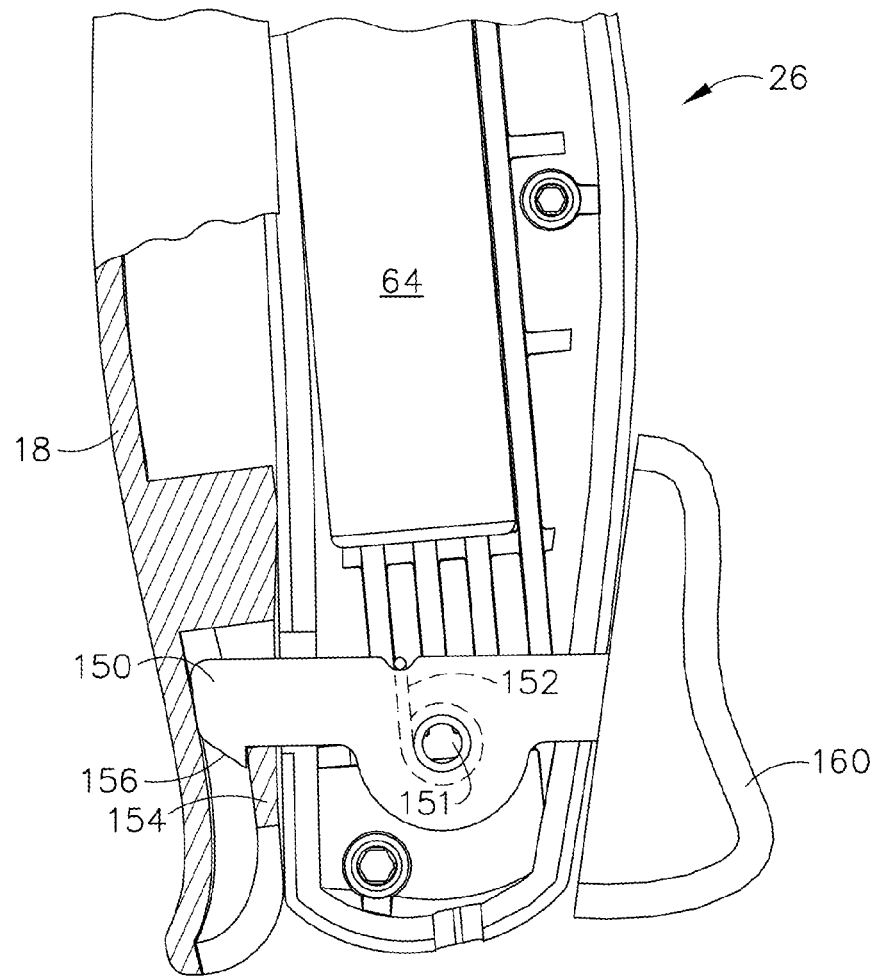

As mentioned above, in using a two-stroke motorized instrument, the operator first pulls back and locks the closure trigger 18. FIGS. 14 and 15 show one embodiment of a way to lock the closure trigger 18 to the pistol grip portion 26 of the handle 6. In the illustrated embodiment, the pistol grip portion 26 includes a hook 150 that is biased to rotate counter clockwise about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or clockwise in FIGS. 14-15) until the closure bar 154 completely passes the sloped portion 156 passes into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 clockwise such that the closure bar 154 is released from the recessed notch 158.

Figure 16:
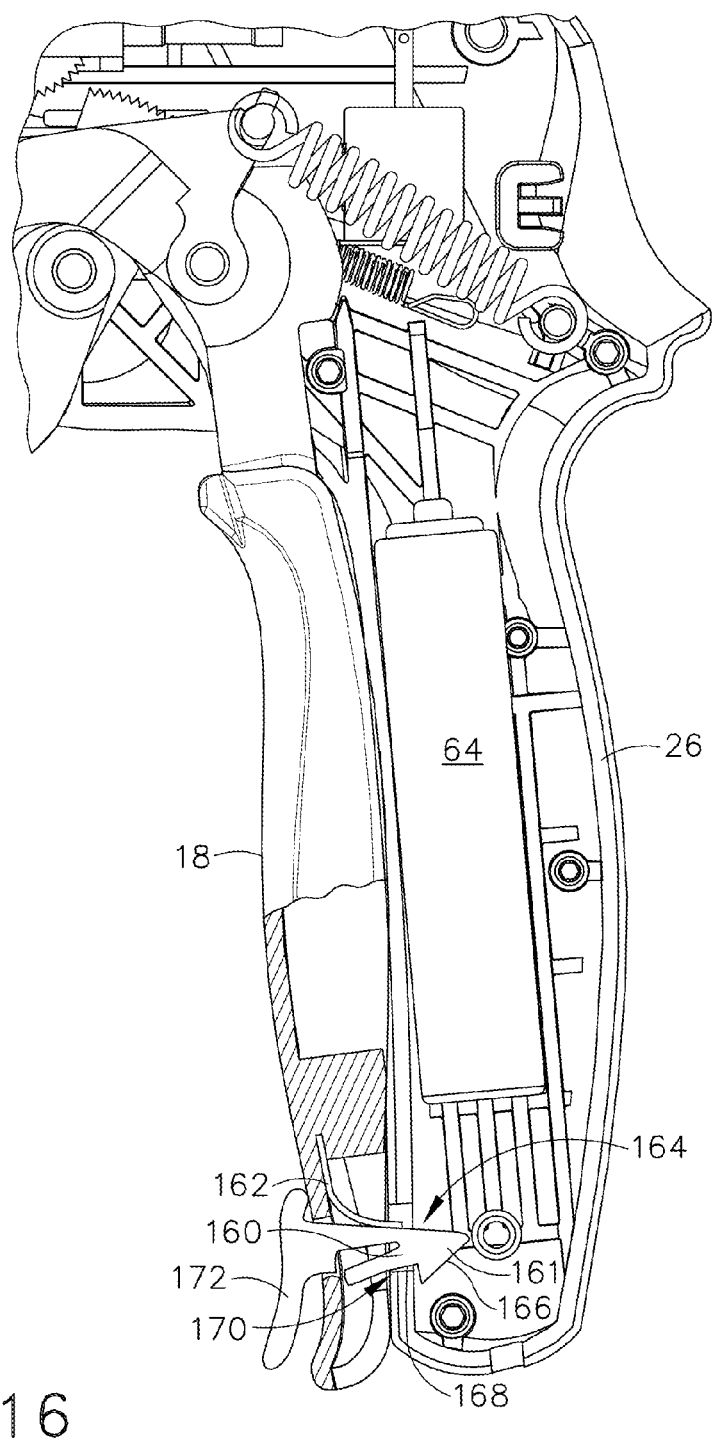

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or clockwise) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate counter clockwise. Eventually the lower chamfered surface 166 fully passes the lower sidewall 168, removing the counter clockwise force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate counter clockwise and allowing the arrow-head portion 161 to slide out of the opening 164.

Figure 17:
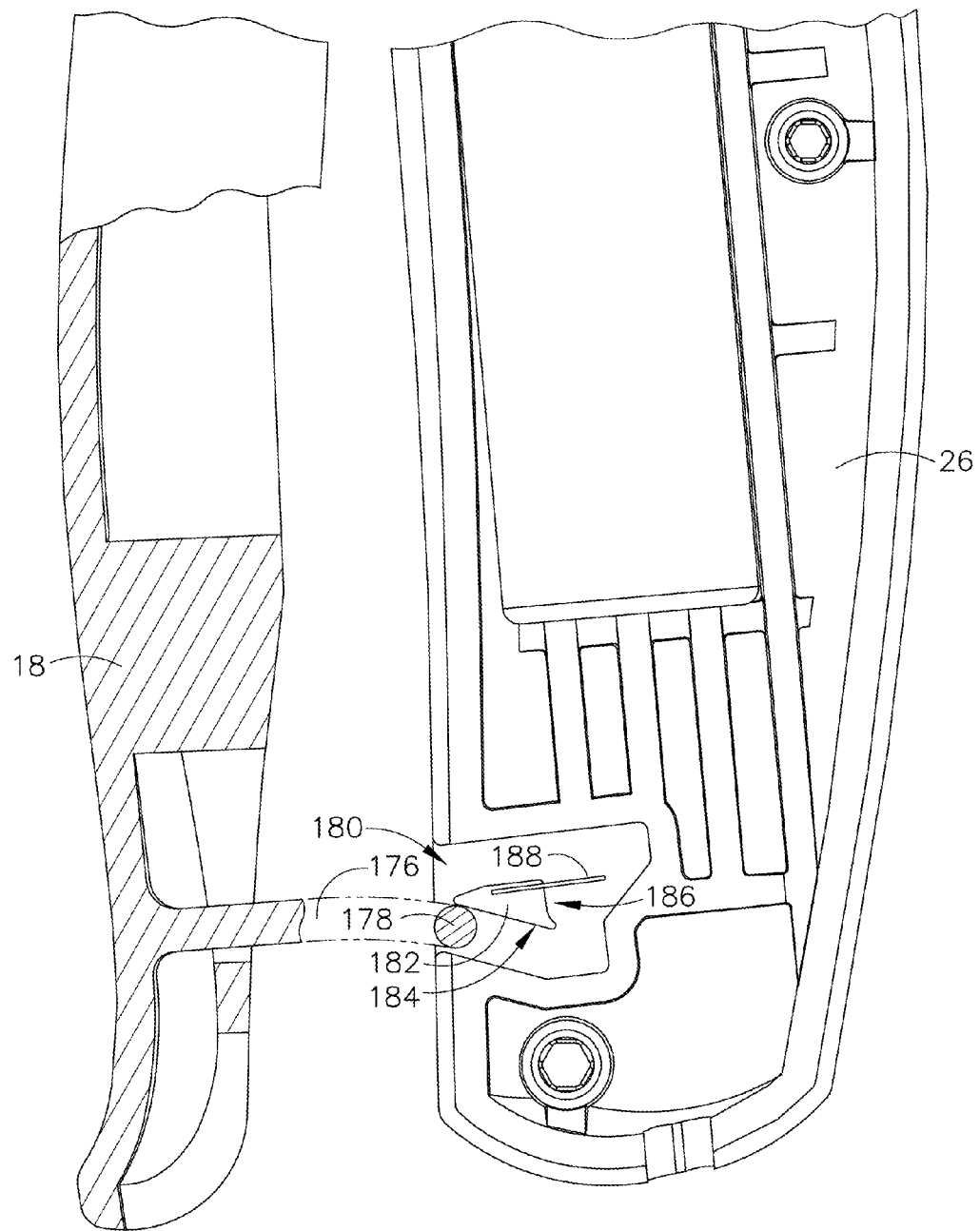
Figure 18:
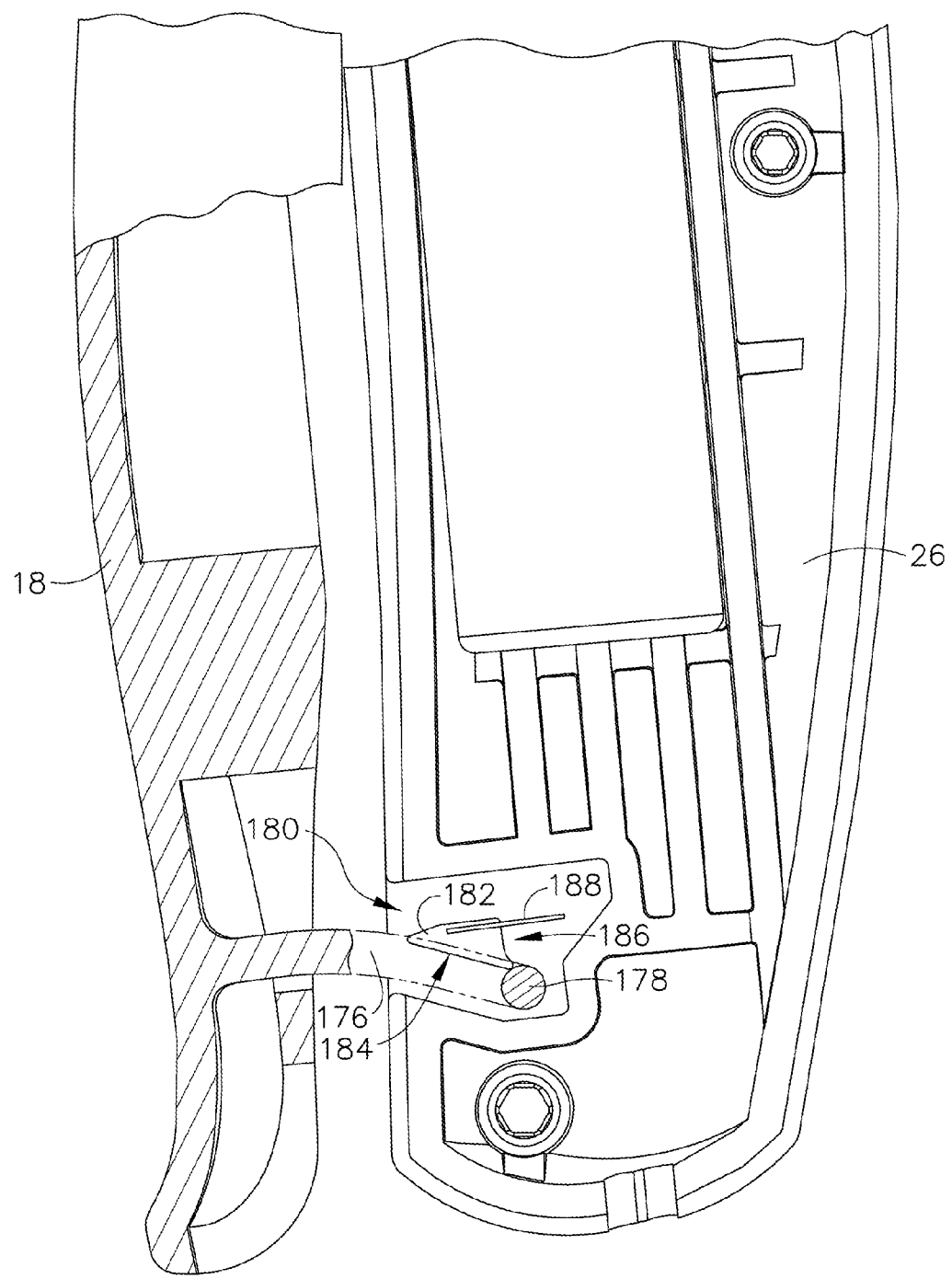
Figure 19:
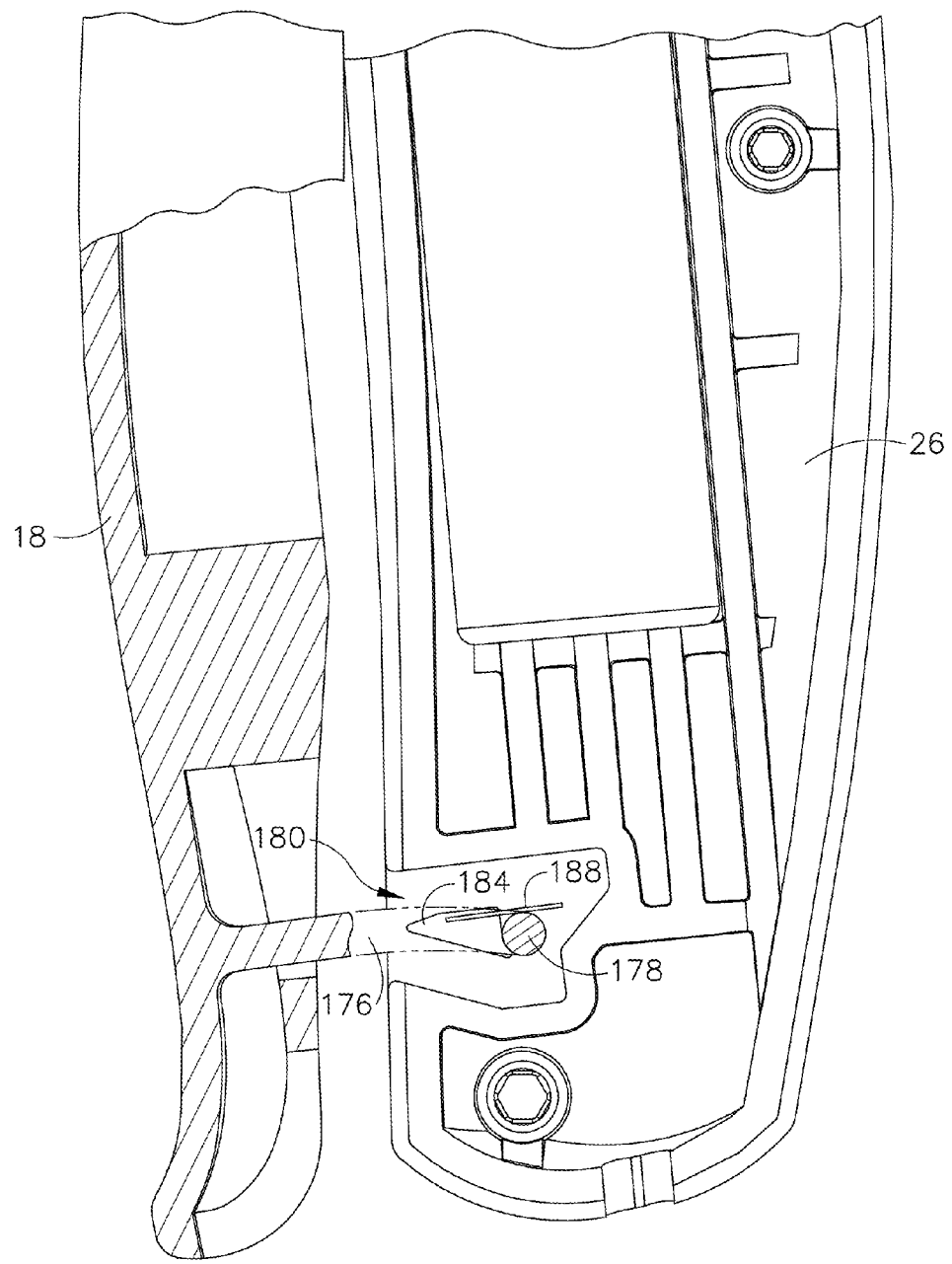

FIGS. 17-22 show a closure trigger locking mechanism according to another embodiment. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (i.e., the arm 176 is rotated clockwise) by the lower surface 184 of the wedge 182, as shown in FIGS. 17 and 18. When the pin 178 fully passes the lower surface 184, the clockwise force on the arm 176 is removed, and the pin 178 is rotated counter clockwise such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
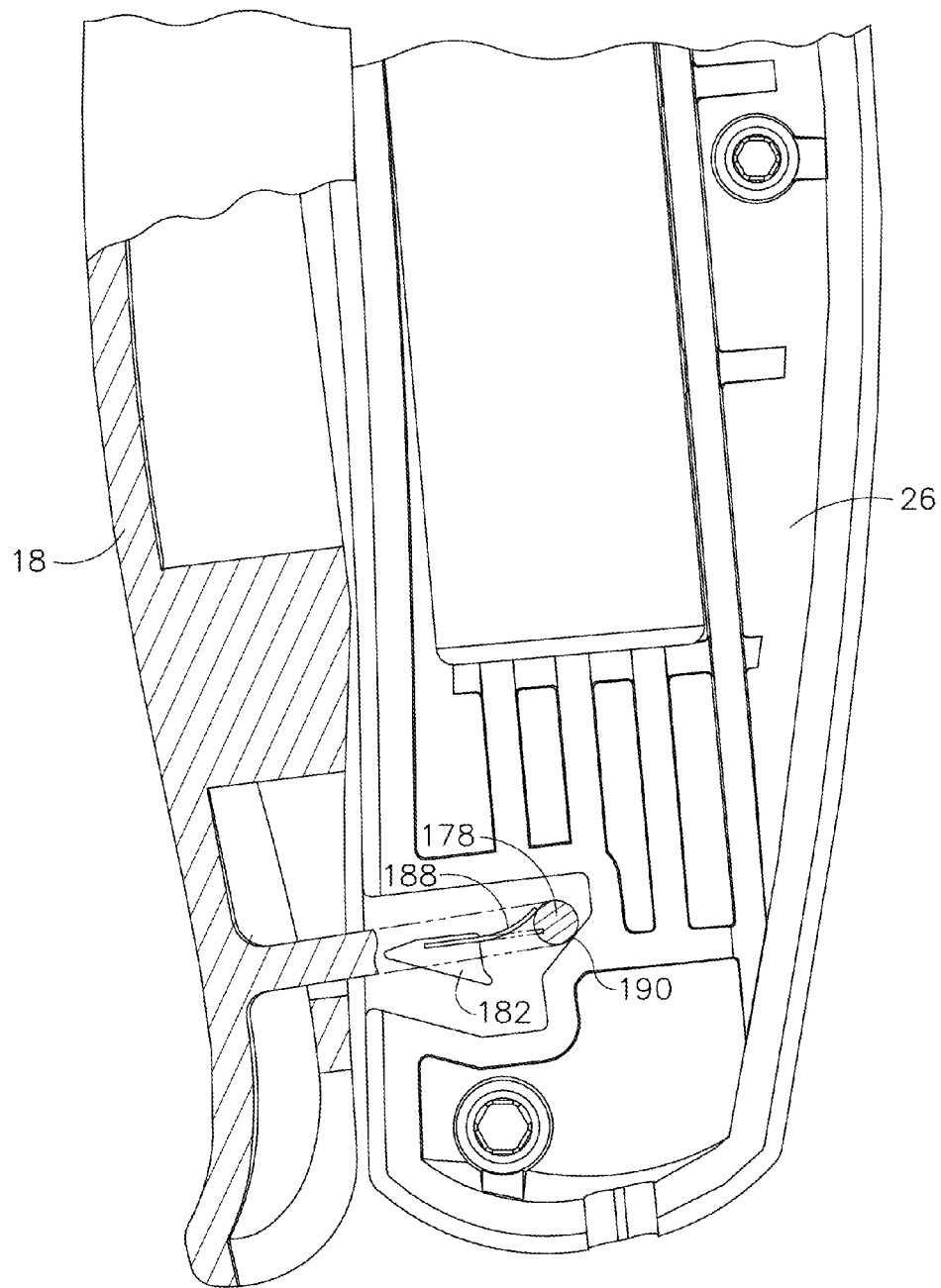
Figure 21:
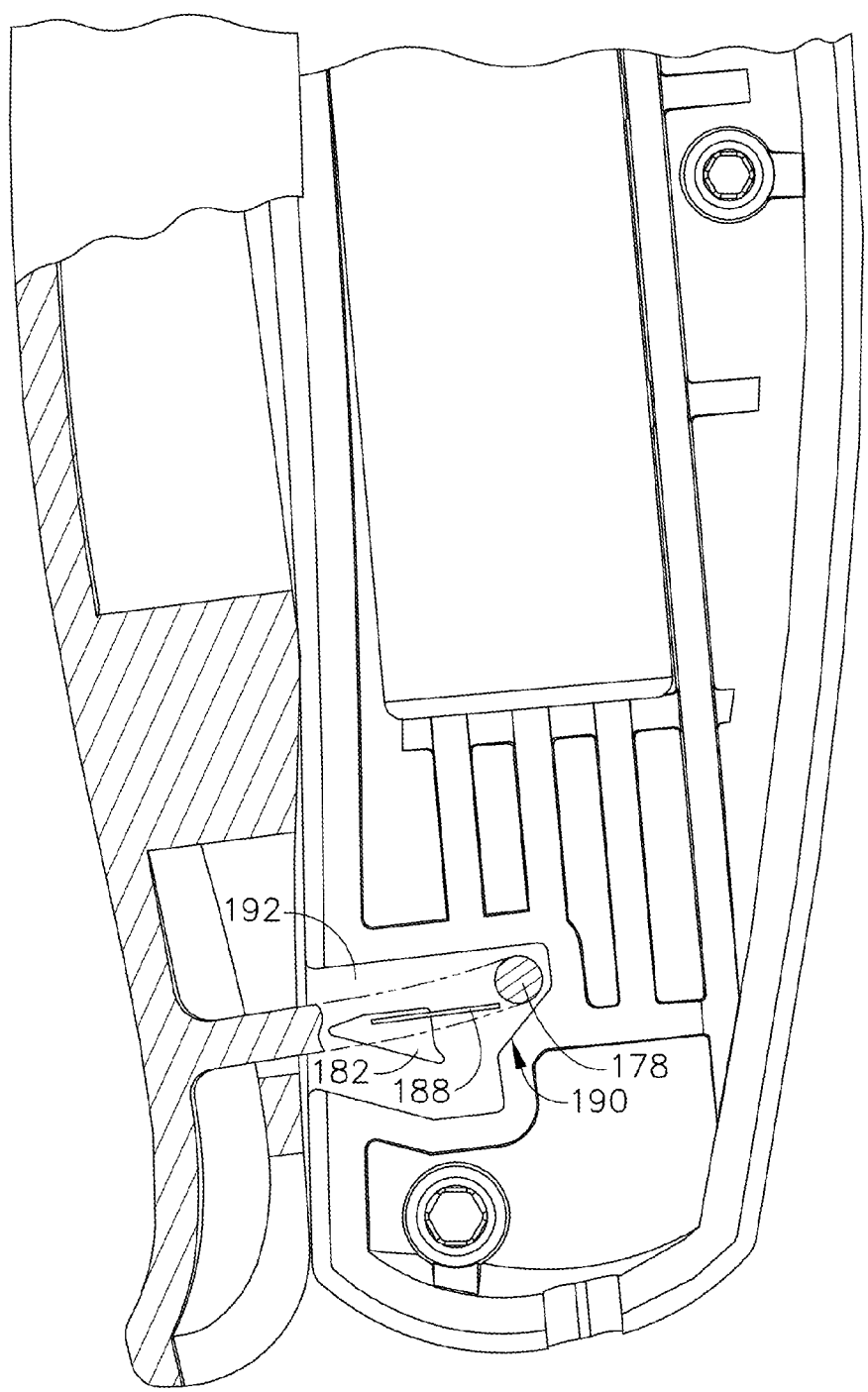
Figure 22:
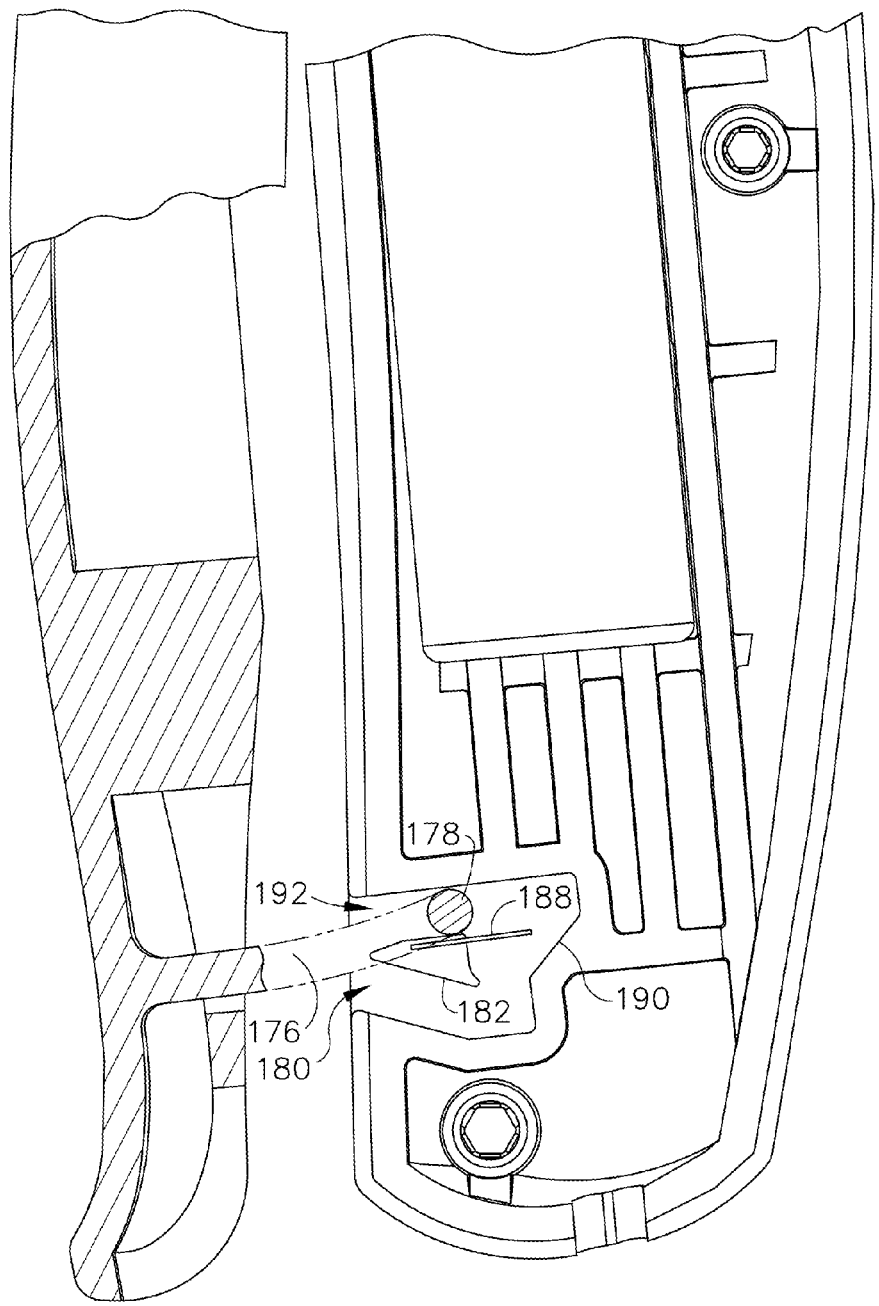

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22.

Figure 23:
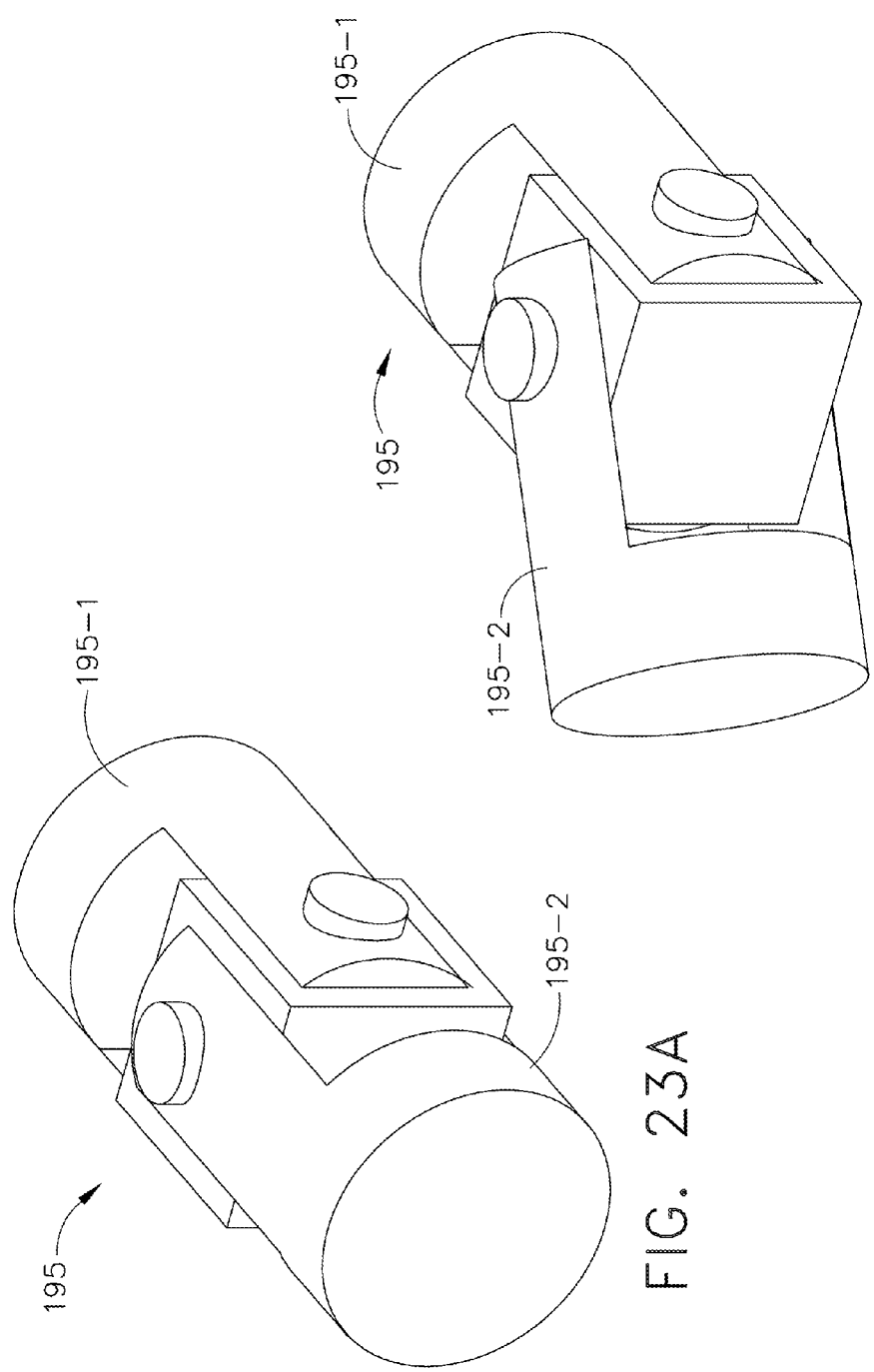
FIGS. 23A-B show a universal joint ("u-joint") that may be employed at the articulation point of a surgical instrument.
Figure 24:
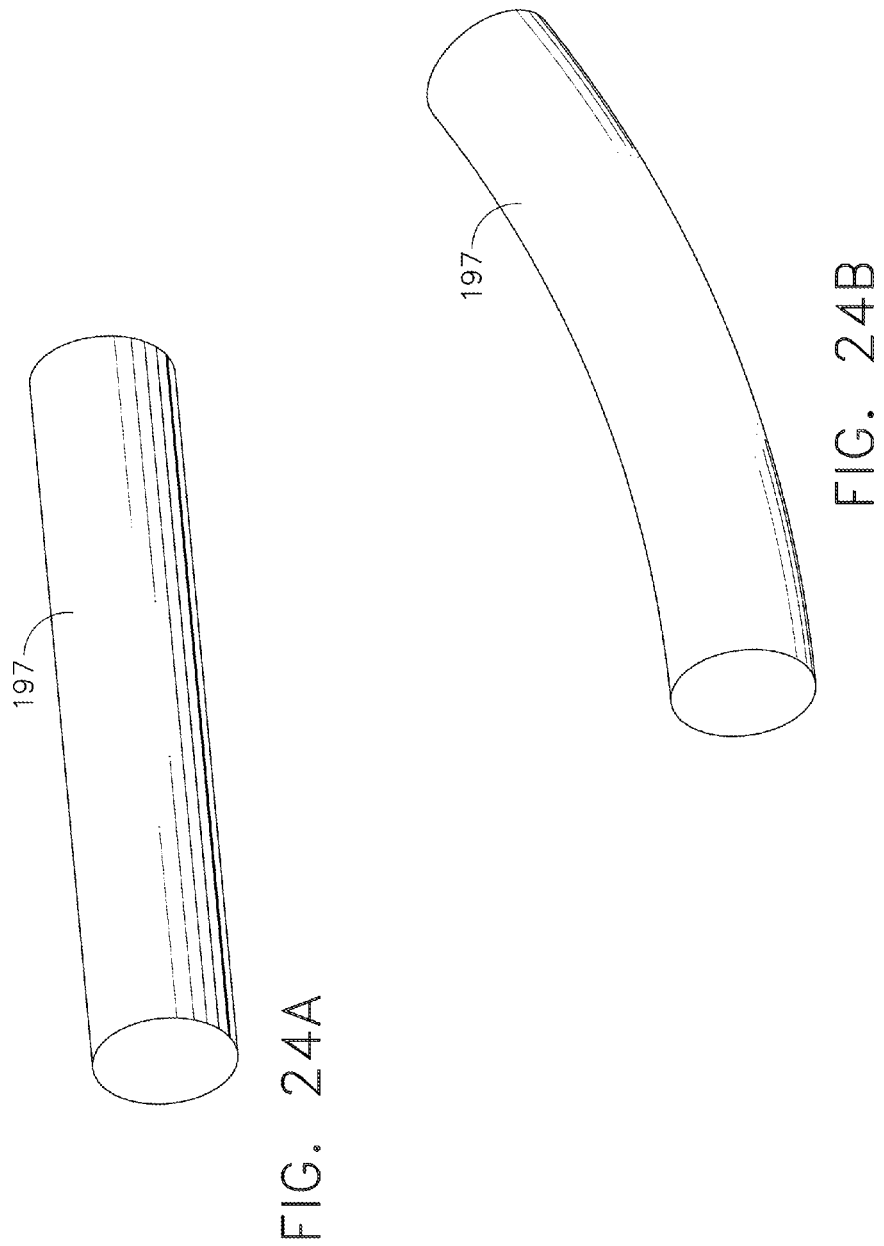
FIGS. 24A-B shows a torsion cable that may be employed at the articulation point of a surgical instrument.
Figure 25:
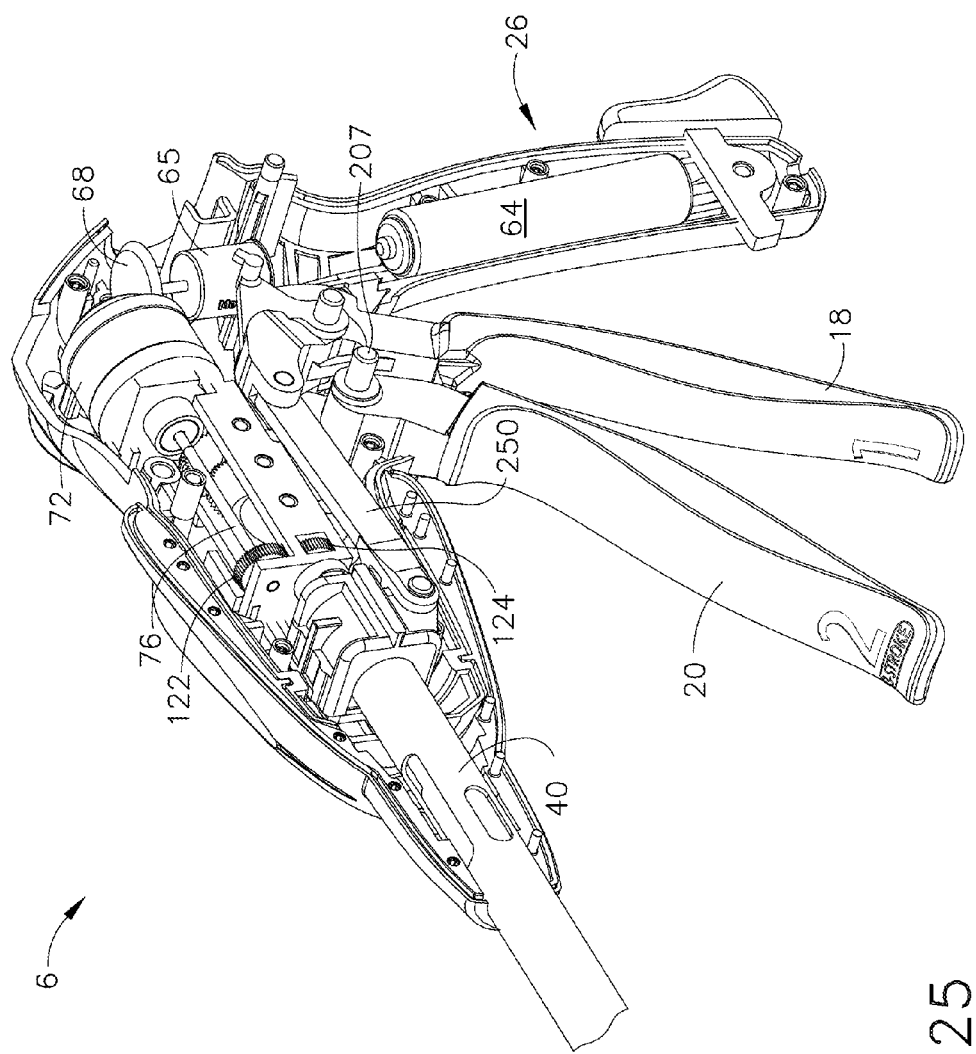
FIGS. 25-31 illustrate a surgical cutting and fastening instrument with power assist.
Figure 26:
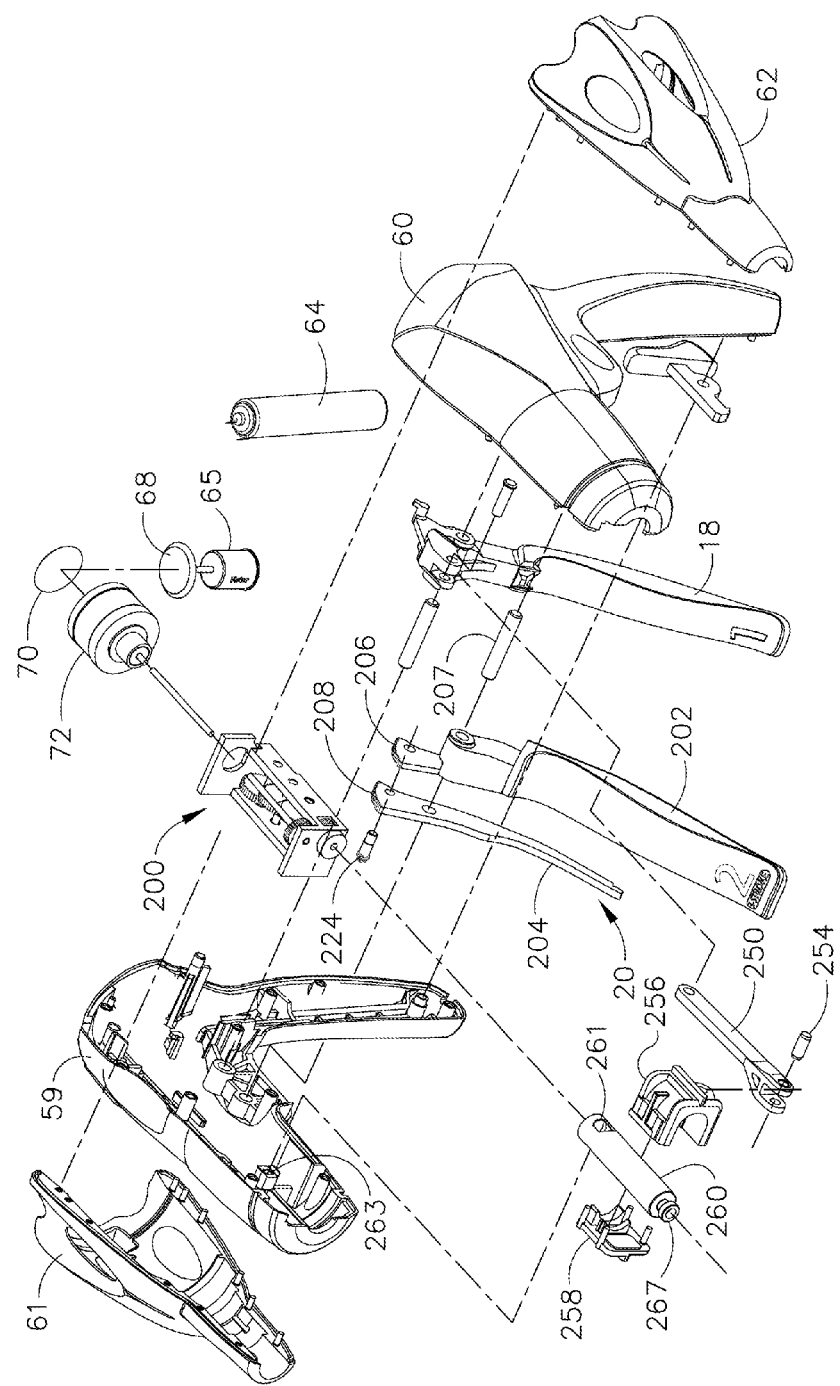
Figure 27:
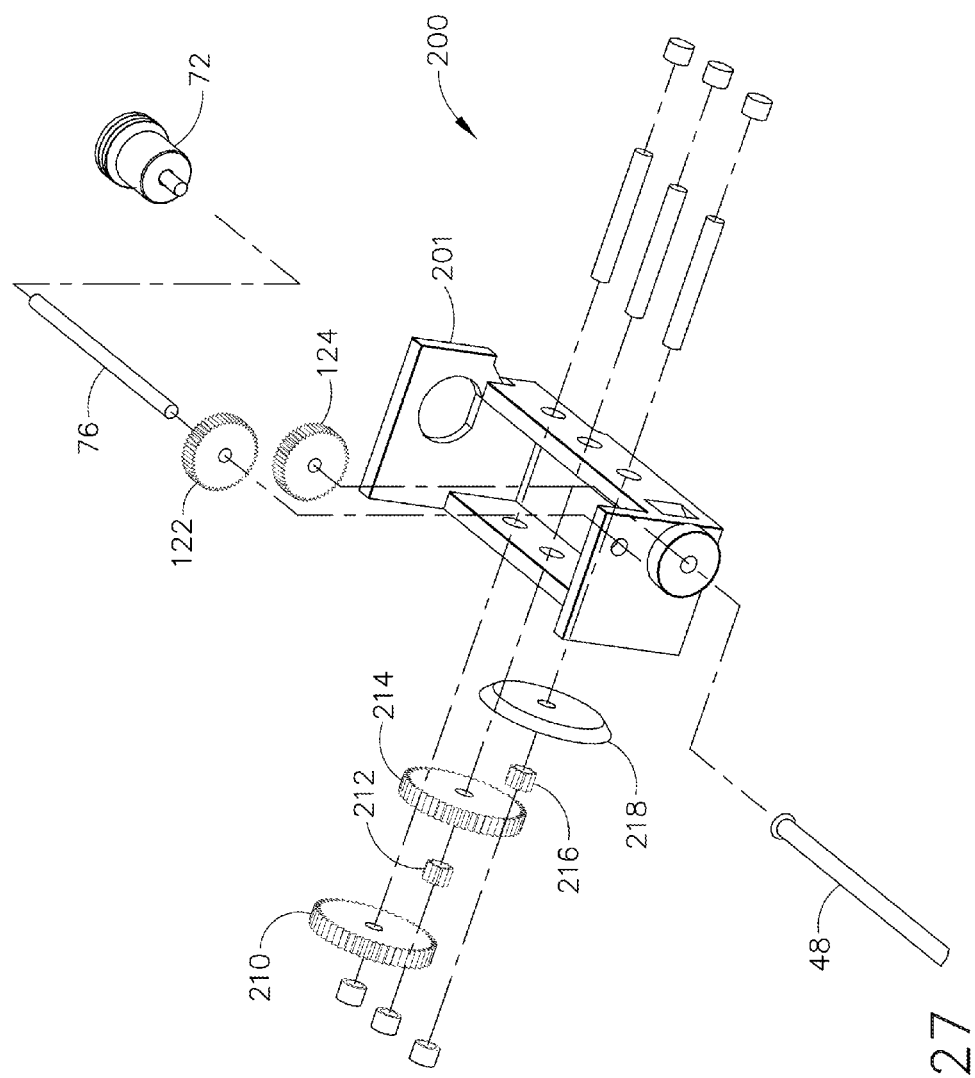
Figure 28:
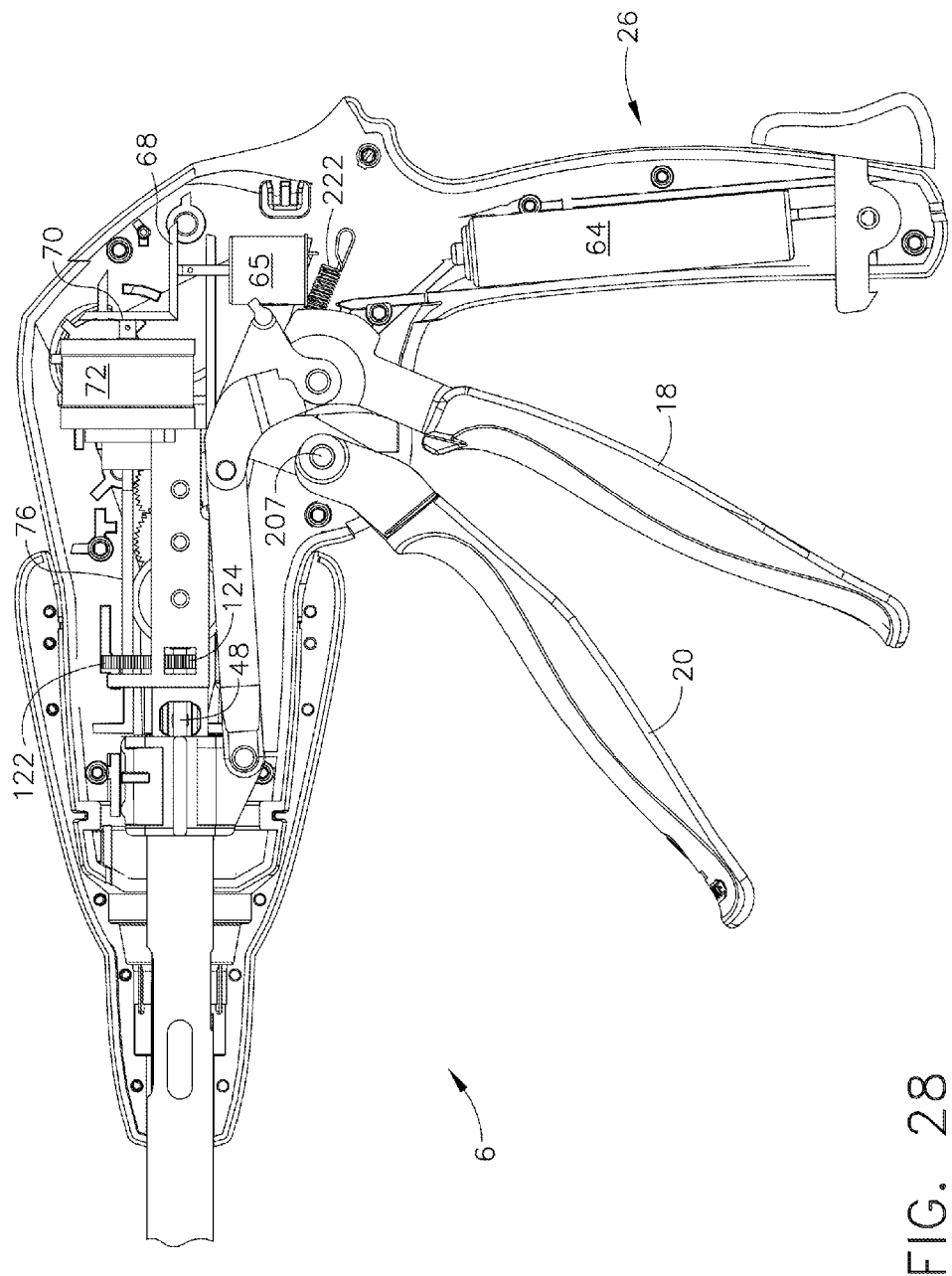
Figure 29:
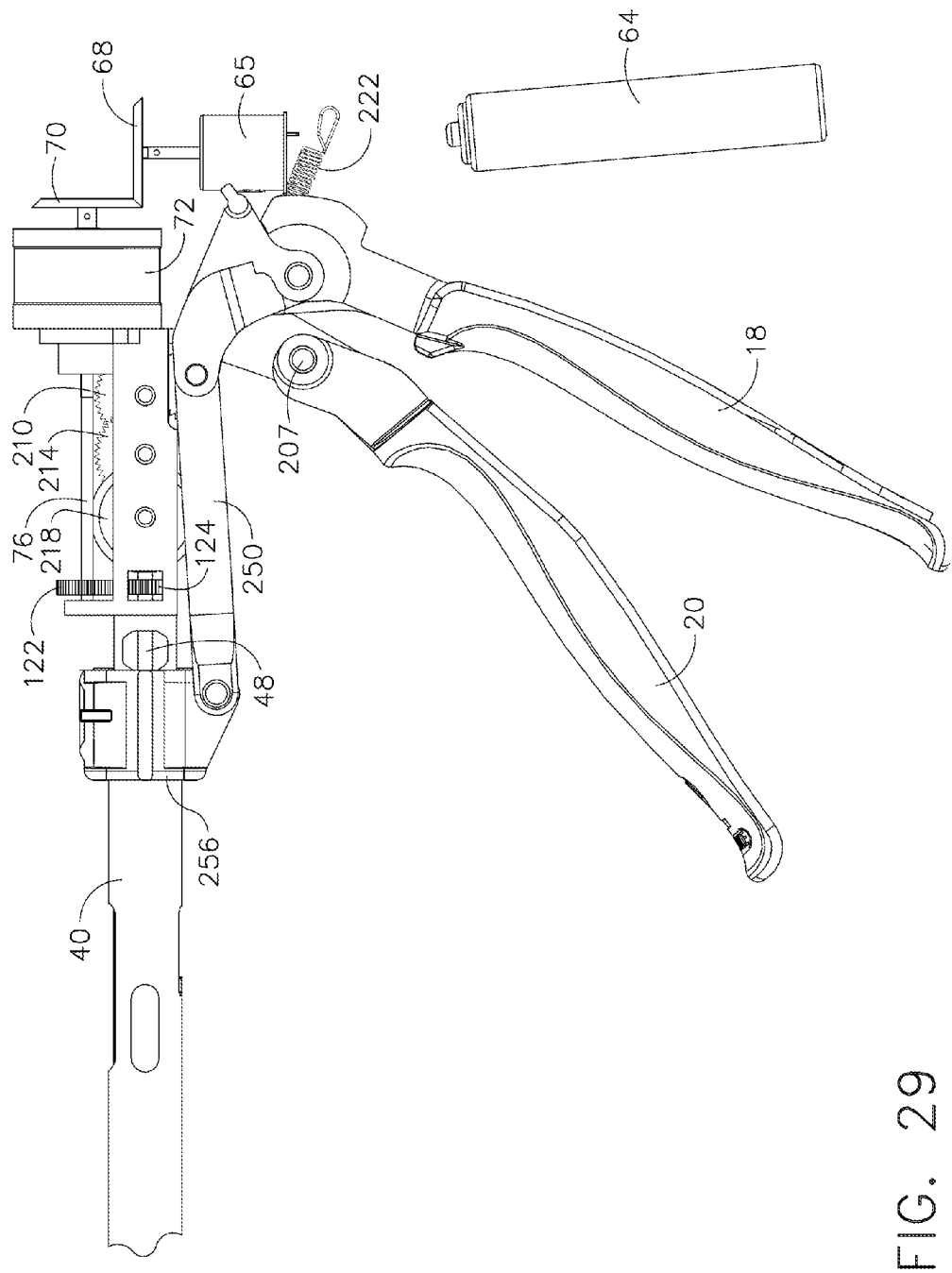
Figure 30:
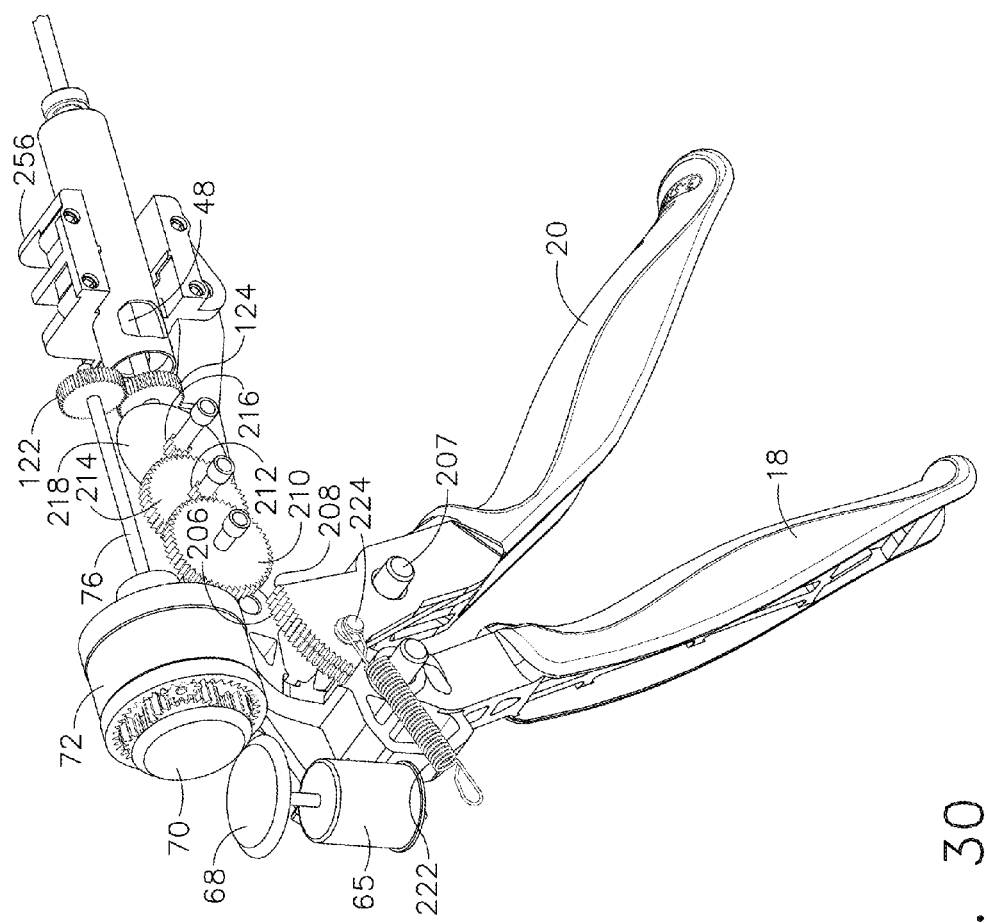
Figure 31:
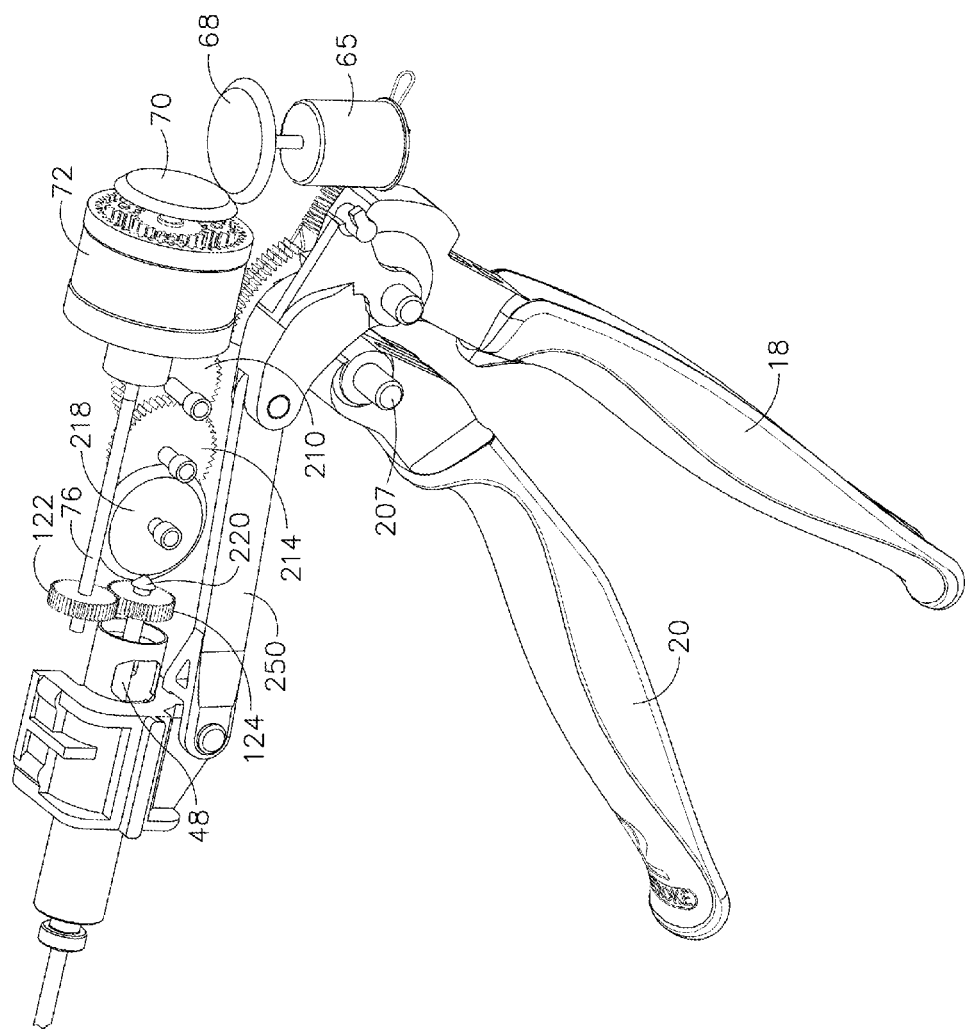

FIGS. 23A-B show a universal joint ("u-joint") 195. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist. The embodiment of FIGS. 25-31 is similar to that of FIGS. 7-10 except that instead of the helical gear drum 80, the embodiment of FIGS. 25-31 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximal end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 25-31 is another power assist motorized instrument 10 that provides feedback to the user regarding the loading force experienced by the instrument.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 207 may be inserted through openings in the firing trigger pieces 202, 204 and may be the point about which the firing trigger 20 rotates. In addition, a spring 222 may bias the firing trigger 20 to rotate in a counter clockwise direction. The spring 222 may have a distal end connected to a pin 224 that is connected to the pieces 202, 204 of the firing trigger 20. The proximal end of the spring 222 may be connected to one of the handle exterior lower side pieces 59, 60.

In the illustrated embodiment, both the main body portion 202 and the stiffening portion 204 includes gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 68, 70 to rotate, which causes the planetary gear 72 to rotate, which causes, via the drive shaft 76, the ring gear 122 to rotate. The ring gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate counter clockwise when the motor 65 provides forward drive for the end effector 12 (and to rotate counter clockwise when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a clockwise rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate counter clockwise, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife 32) and the end of retraction operation (full retraction of the knife 32). A similar circuit to that described above in connection with FIG. 11 may be used to appropriately power the motor 65.

FIGS. 32-36 illustrate a two-stroke, motorized surgical cutting and fastening instrument 10 with power assist according to another embodiment. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the clockwise direction. The upper portion 230 may also include a lower arm 234 that contacts an upper surface of the lower portion 228 of the firing trigger 20 such that when the upper portion 230 is caused to rotate clockwise the lower portion 228 also rotates clockwise, and when the lower portion 228 rotates counter clockwise the upper portion 230 also rotates counter clockwise. Similarly, the lower portion 228 includes a rotational stop 238 that engages a shoulder of the upper portion 230. In that way, when the upper portion 230 is caused to rotate counter clockwise the lower portion 228 also rotates counter clockwise, and when the lower portion 228 rotates clockwise the upper portion 230 also rotates clockwise.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
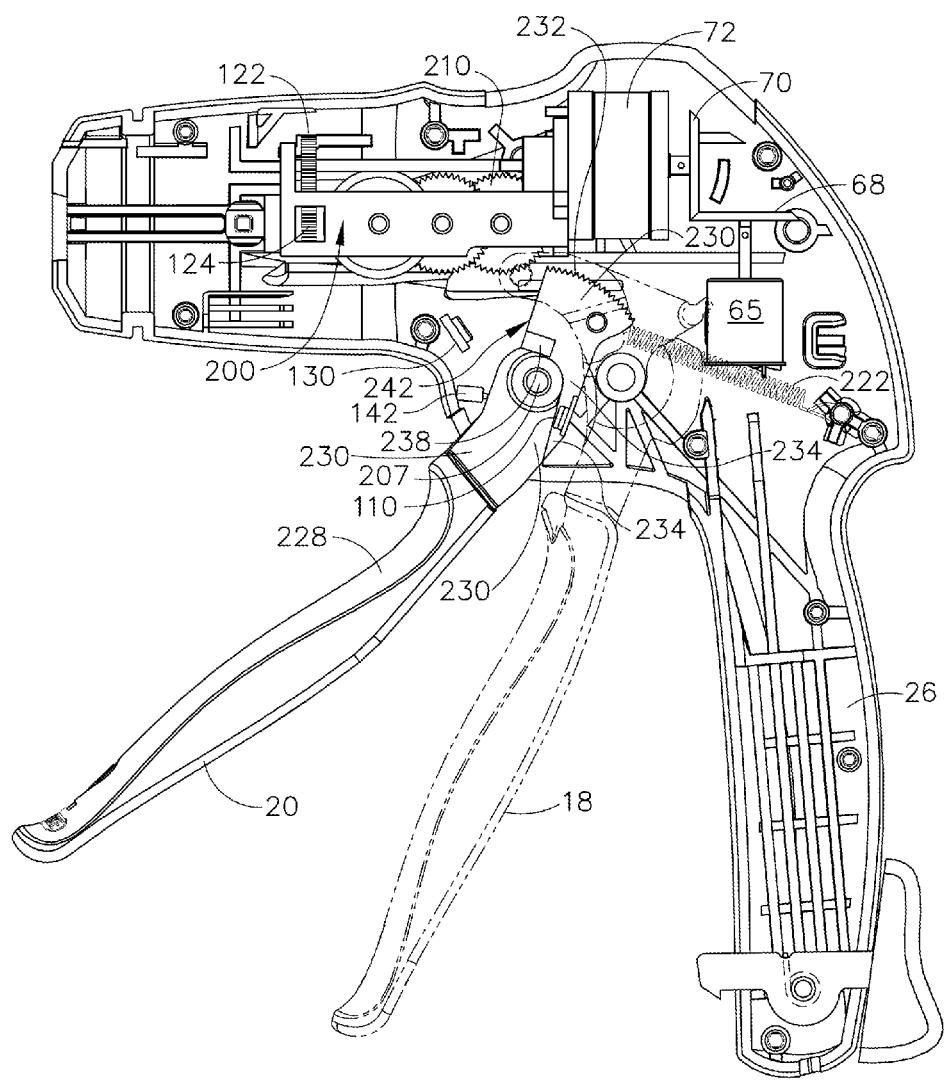
FIGS. 32-36 illustrate a surgical cutting and fastening instrument with power assist according to another embodiment.
Figure 33:
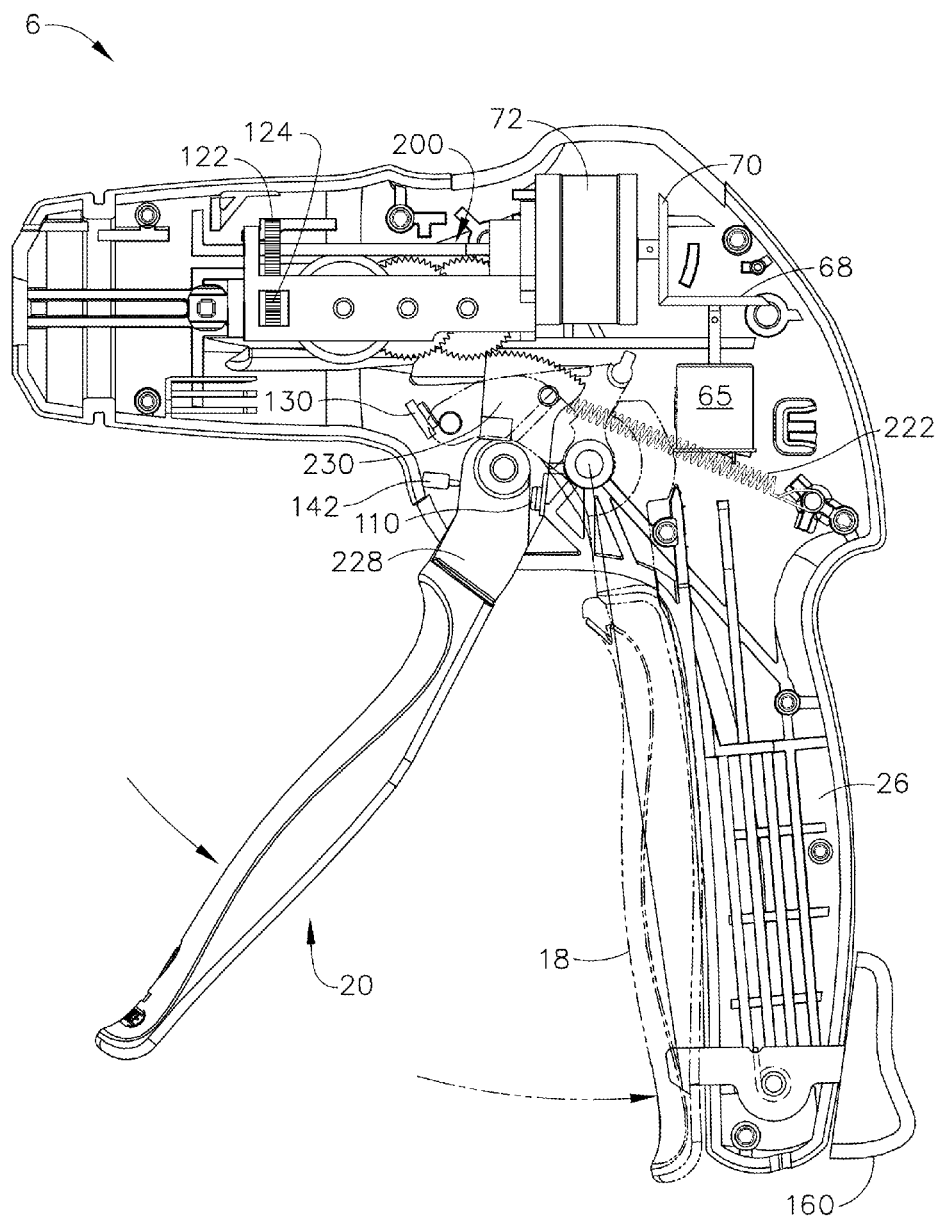
Figure 34:
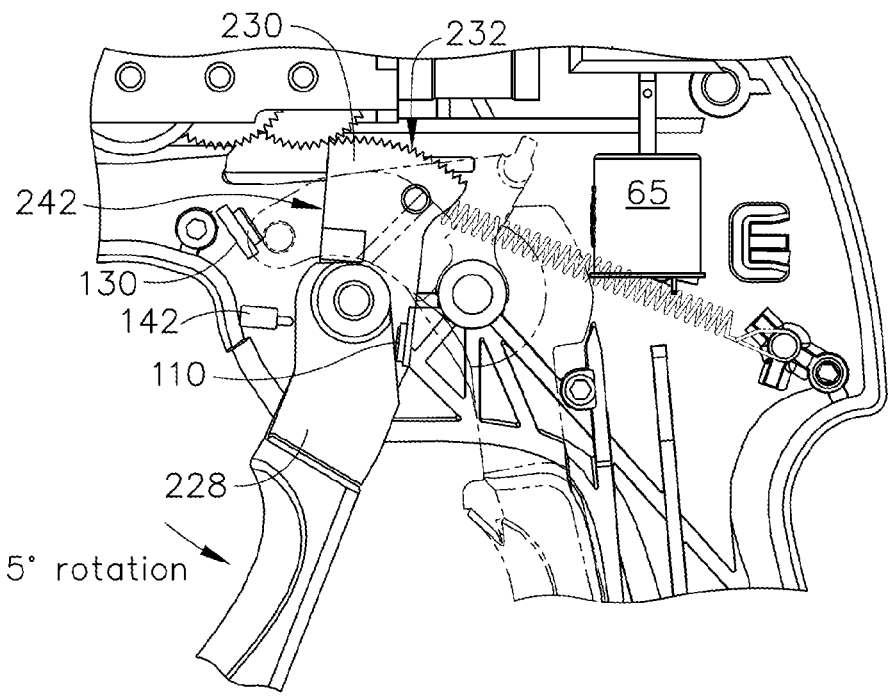
Figure 35:
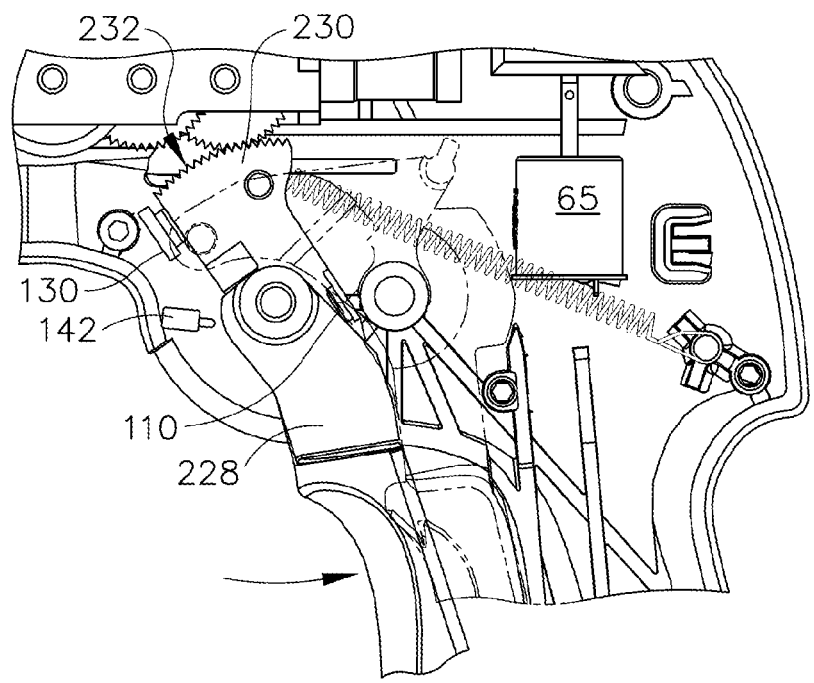
Figure 36:
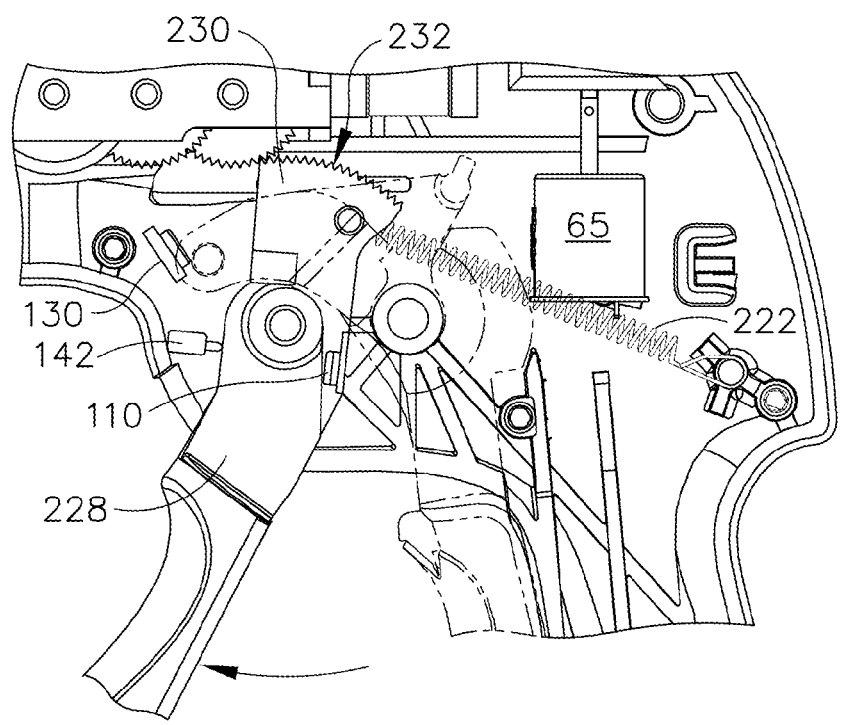

In operation, when an operator retracts the closure trigger 18 into the locked position, the firing trigger 20 is retracted slightly (through mechanisms known in the art, including U.S. Pat. No. 6,978,921, entitled SURGICAL STAPLING INSTRUMENT INCORPORATING AN E-BEAM FIRING MECHANISM, and U.S. Pat. No. 6,905,057, entitled SURGICAL STAPLING INSTRUMENT INCORPORATING A FIRING MECHANISM HAVING A LINKED RACK TRANSMISSION, the entire disclosures of which are incorporated herein by reference) so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (i.e., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 232 is caused to rotate counter clockwise, which causes the lower portion 228 to also rotate counter clockwise.

When the knife 32 is fully deployed (i.e., at the end of the cutting stroke), the front face 242 of the upper portion 230 trips the reverse motor sensor 130, which sends a signal to the motor 65 to reverse rotational directional. This causes the main drive shaft assembly to reverse rotational direction to retract the knife 32. Reverse rotation of the main drive shaft assembly also causes the gears 210-220 in the gear box assembly to reverse direction, which causes the upper portion 230 of the firing trigger 20 to rotate clockwise, which causes the lower portion 228 of the firing trigger 20 to rotate clockwise until the lower portion 228 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a clockwise rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate counter clockwise, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor 65, gear drive train, and end effector 12) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments, the user may be provided with tactile feedback regarding the position of the knife 32 in the end effector, but without having the firing trigger 20 geared into the gear drive train. FIGS. 37-40 illustrate a motorized surgical cutting and fastening instrument with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIG. 32-36, however, the upper portion 230 does not have a gear portion that mates with part of the gear drive train. Instead, the instrument includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
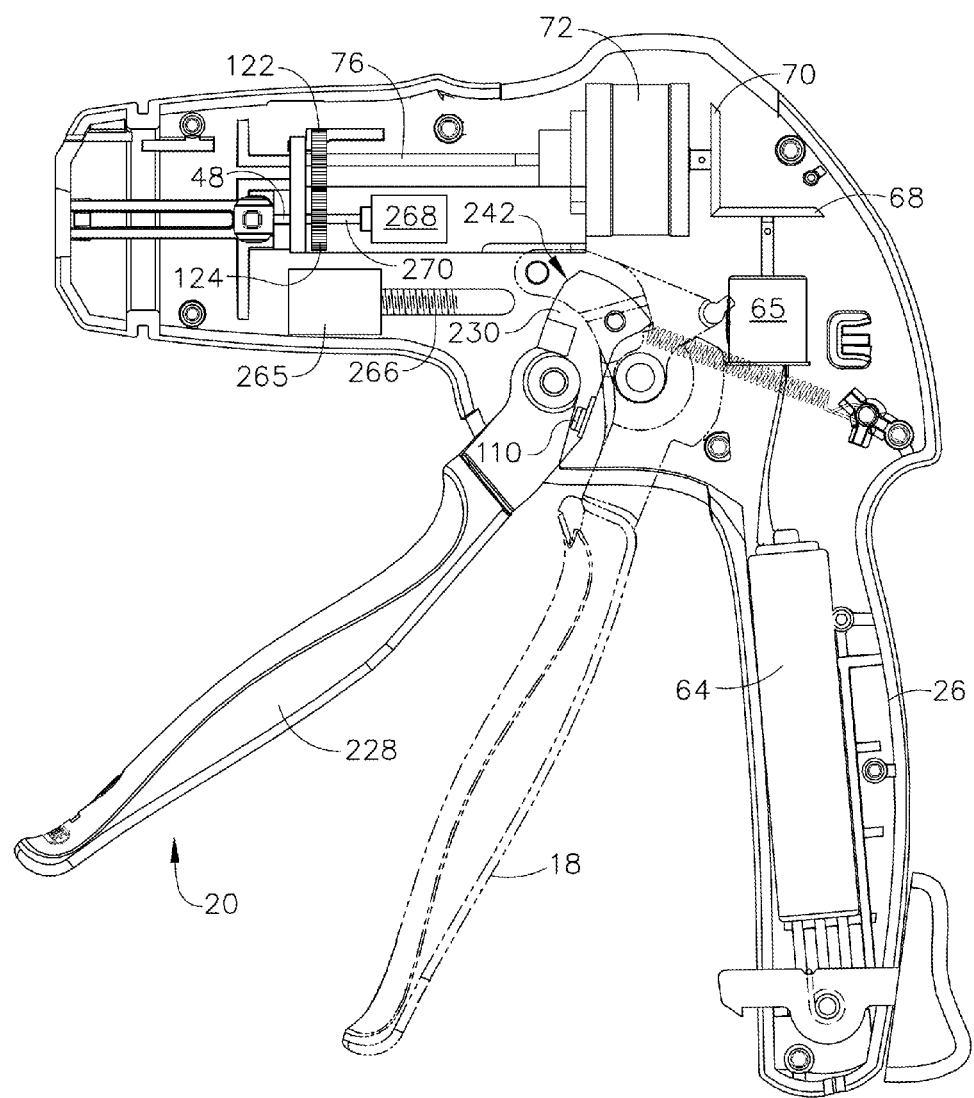
FIGS. 37-40 illustrate a surgical cutting and fastening instrument with tactile feedback to embodiments of the present invention.
Figure 38:
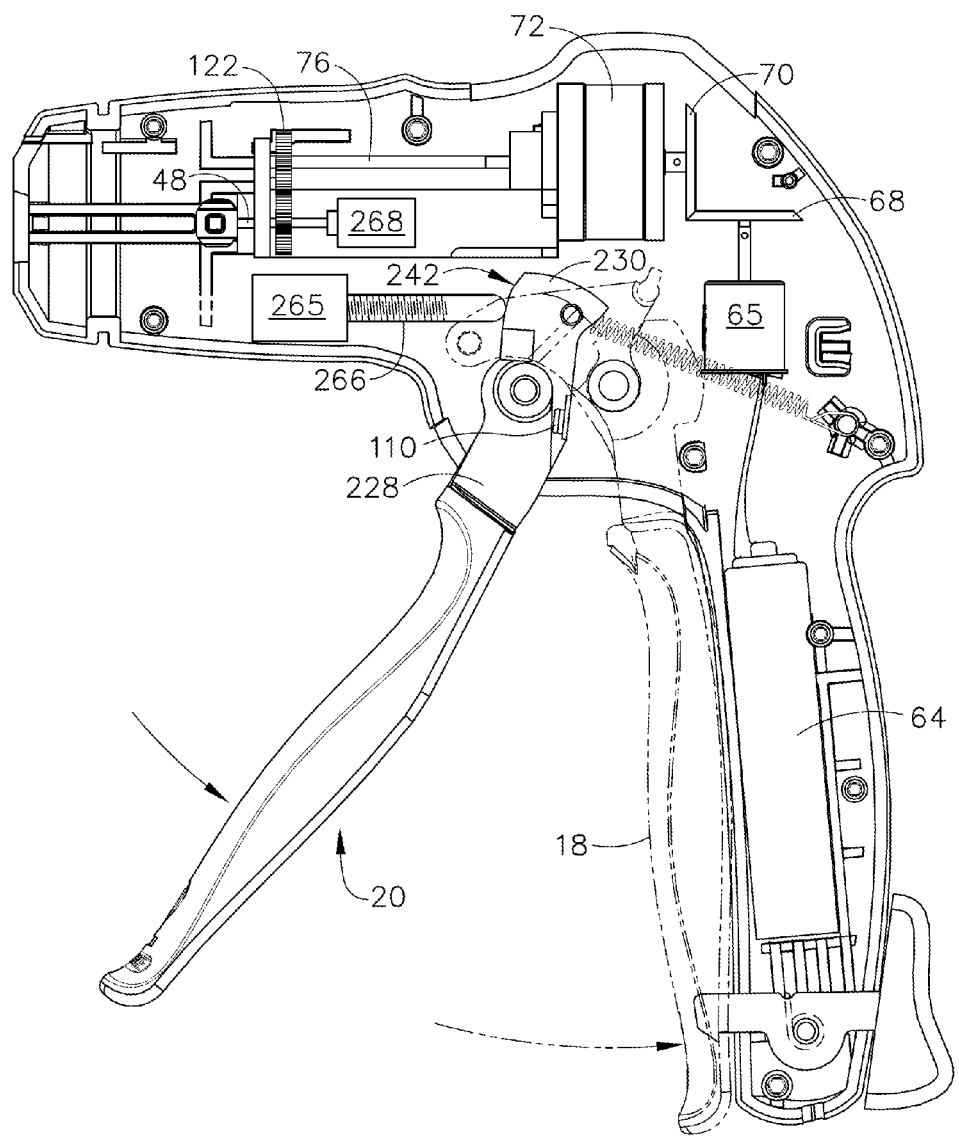
Figure 39:
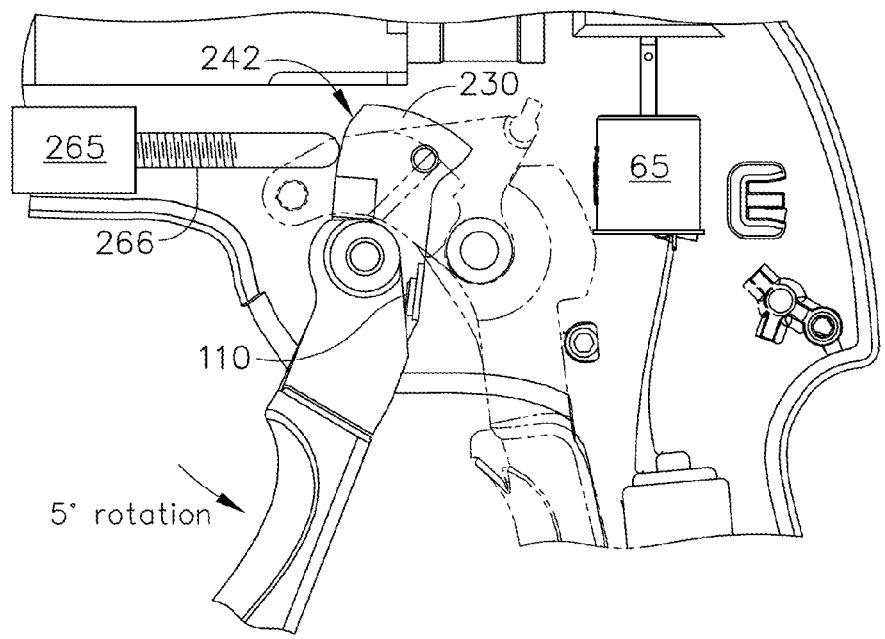
Figure 40:
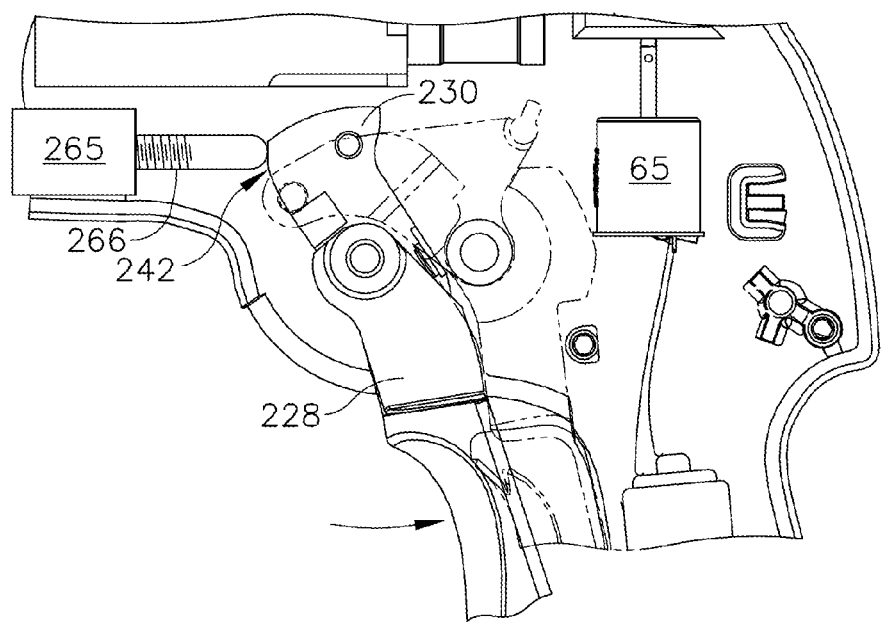

In operation, as shown in FIG. 37, when the closure trigger 18 is not locked into the clamped position, the firing trigger 20 is rotated away from the pistol grip portion 26 of the handle 6 such that the front face 242 of the upper portion 230 of the firing trigger 20 is not in contact with the proximal end of the threaded rod 266. When the operator retracts the closure trigger 18 and locks it in the clamped position, the firing trigger 20 rotates slightly towards the closure trigger 18 so that the operator can grasp the firing trigger 20, as shown in FIG. 38. In this position, the front face 242 of the upper portion 230 contacts the proximal end of the threaded rod 266.

As the user then retracts the firing trigger 20, after an initial rotational amount (e.g. 5 degrees of rotation) the run motor sensor 110 may be activated such that, as explained above, the sensor 110 sends a signal to the motor 65 to cause it to rotate at a forward speed proportional to the amount of retraction force applied by the operator to the firing trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to cause the second motor 265 to rotate, which causes the threaded rod 266 to retract into the motor 265. This allows the upper portion 230 of the firing trigger 20 to rotate counter clockwise, which allows the lower portion 228 of the firing trigger to also rotate counter clockwise. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (i.e., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate clockwise, which causes the lower portion 228 to rotate clockwise. In that way, the operator may experience a clockwise force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

Figure 41:
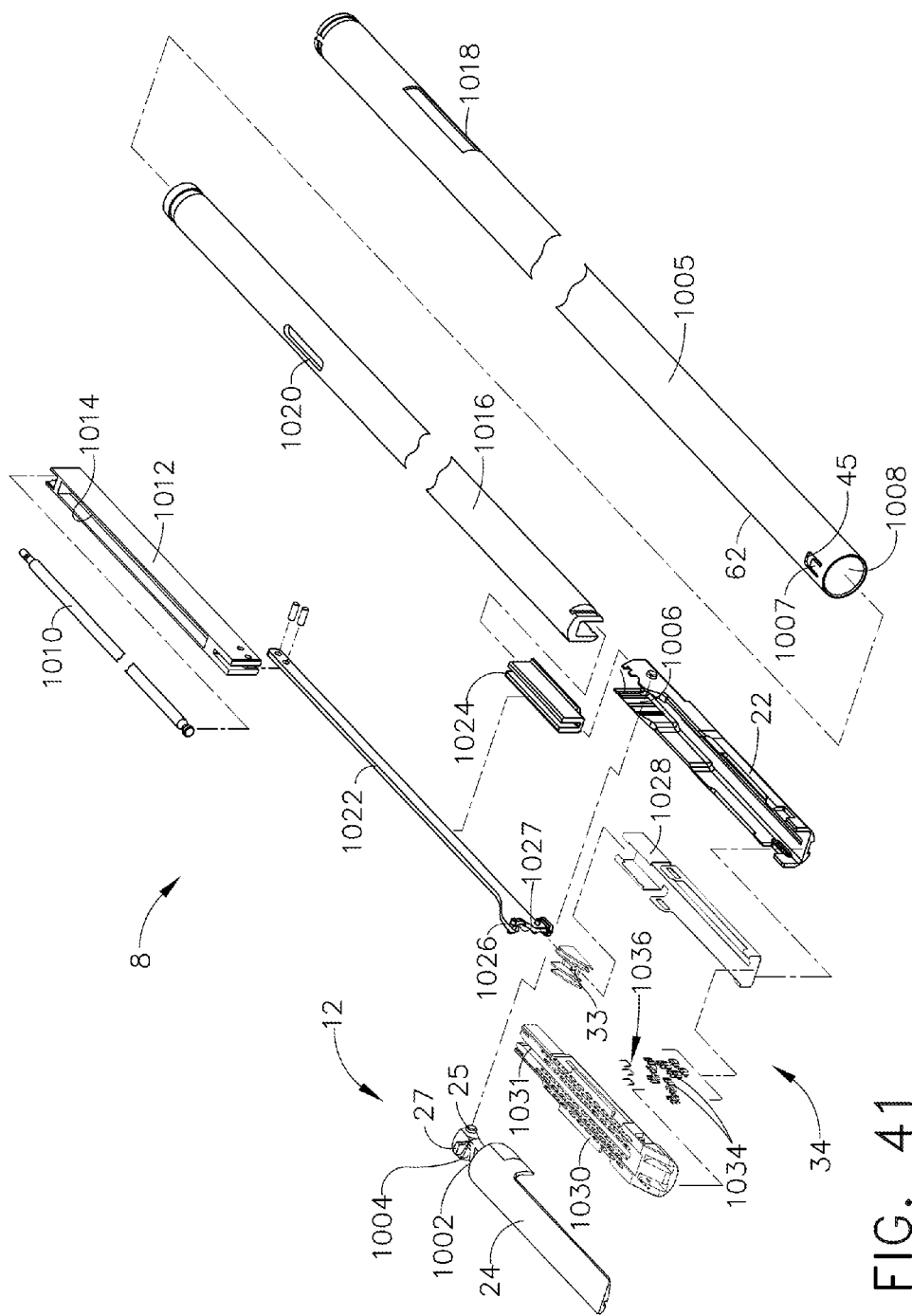
FIG. 41 illustrates an exploded view of an end effector and shaft of a surgical instrument.
Figure 42:
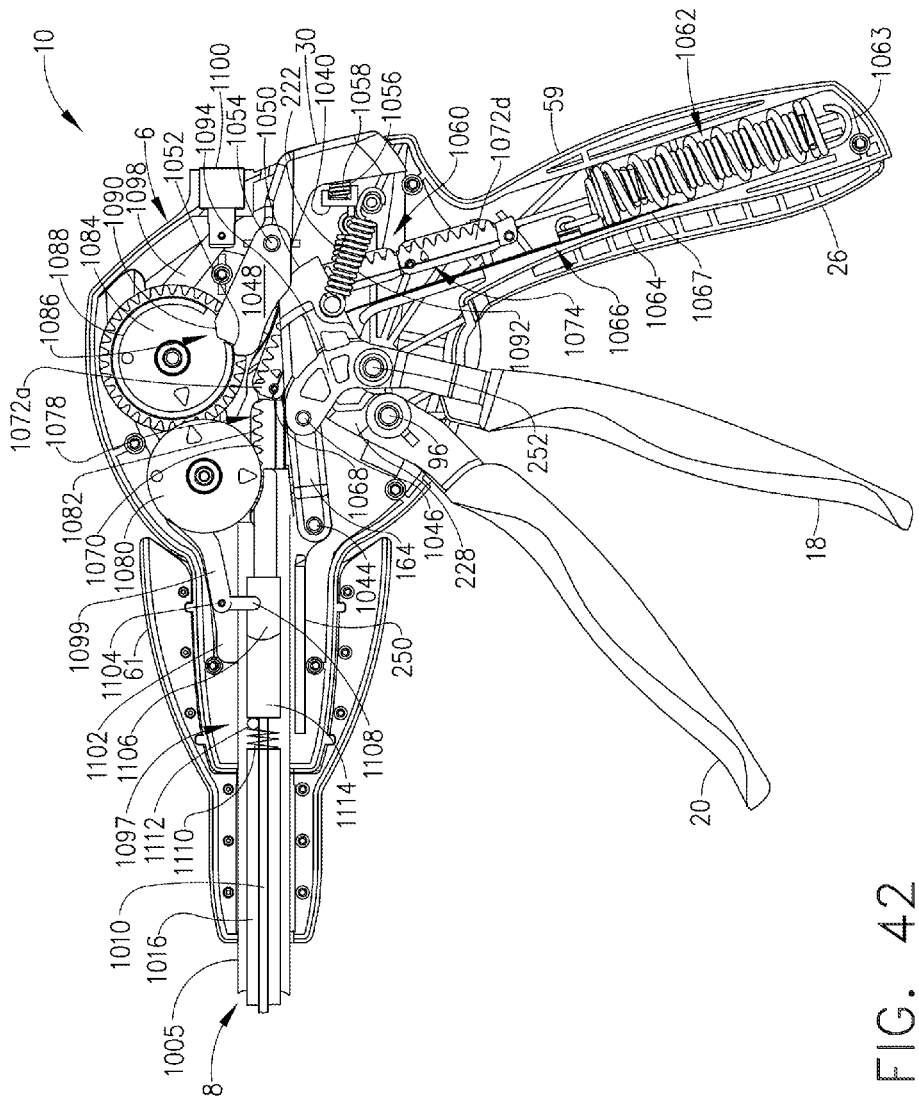
FIG. 42 illustrates a side view of the handle of a mechanically actuated surgical instrument.
Figure 43:
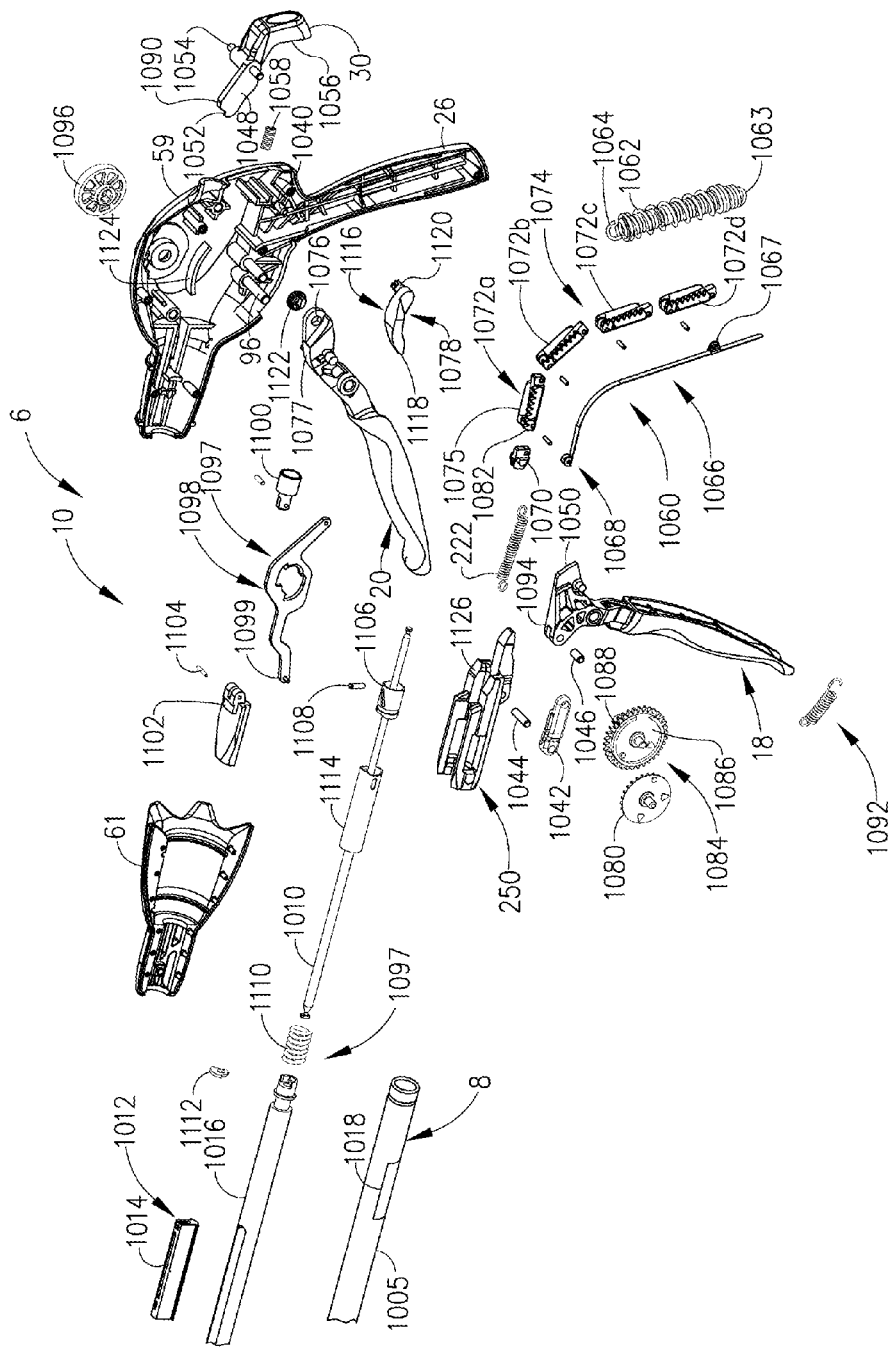
FIG. 43 illustrates an exploded view of the handle of the mechanically actuated instrument of FIG. 42.

FIGS. 41-43 illustrate an exemplary embodiment of a mechanically actuated endocutter, and in particular the handle 6, shaft 8 and end effector 12 thereof. Further details of a mechanically actuated endocutter may be found in U.S. Pat. No. 7,083,075, entitled MULTI-STROKE FIRING MECHANISM WITH AUTOMATIC END OF STROKE RETRACTION, the entire disclosure of which is incorporated herein by reference. With reference to FIG. 41, the end effector 12 responds to the closure motion from the handle 6 (not depicted in FIG. 41) first by including an anvil face 1002 connecting to an anvil proximal end 1004 that includes laterally projecting anvil pivot pins 25 that are proximal to a vertically projecting anvil tab 27. The anvil pivot pins 25 translate within kidney shaped openings 1006 in the staple channel 22 to open and close anvil 24 relative to channel 22. The tab 27 engages a bent tab 1007 extending inwardly in tab opening 45 on a distal end 1008 of the closure tube 1005, the latter distally terminating in a distal edge 1008 that pushes against the anvil face 1002. Thus, when the closure tube 1005 moves proximally from its open position, the bent tab 1007 of the closure tube 1005 draws the anvil tab 27 proximally, and the anvil pivot pins 25 follow the kidney shaped openings 1006 of the staple channel 22 causing the anvil 24 to simultaneously translate proximally and rotate upward to the open position. When the closure tube 1005 moves distally, the bent tab 1007 in the tab opening 45 releases from the anvil tab 27 and the distal edge 1008 pushes on the anvil face 1002, closing the anvil 24.

With continued reference to FIG. 41, the shaft 8 and end effector 12 also include components that respond to a firing motion of a firing rod 1010. In particular, the firing rod 1010 rotatably engages a firing trough member 1012 having a longitudinal recess 1014. Firing trough member 1012 moves longitudinally within frame 1016 in direct response to longitudinal motion of firing rod 1010. A longitudinal slot 1018 in the closure tube 1005 operably couples with the right and left exterior side handle pieces 61, 62 of the handle 6 (not shown in FIG. 41). The length of the longitudinal slot 1018 in the closure tube 1005 is sufficiently long to allow relative longitudinal motion with the handle pieces 61, 62 to accomplish firing and closure motions respectively with the coupling of the handle pieces 61, 62 passing on through a longitudinal slot 1020 in the frame 1016 to slidingly engage the longitudinal recess 1014 in the frame trough member 1012.

The distal end of the frame trough member 1012 is attached to a proximal end of a firing bar 1022 that moves within the frame 1016, specifically within a guide 1024 therein, to distally project the knife 32 into the end effector 12. The end effector 12 includes a staple cartridge 34 that is actuated by the knife 32. The staple cartridge 34 has a tray 1028 that holds a staple cartridge body 1030, a wedge sled driver 33, staple drivers 1034 and staples 1036. It will be appreciated that the wedge sled driver 33 longitudinally moves within a firing recess (not shown) located between the cartridge tray 1028 and the cartridge body 1030. The wedge sled driver 33 presents camming surfaces that contact and lift the staple drivers 1034 upward, driving the staples 1036. The staple cartridge body 1030 further includes a proximally open, vertical slot 1031 for passage of the knife 32. Specifically, a cutting surface 1027 is provided along a distal end of knife 32 to cut tissue after it is stapled.

It should be appreciated that the shaft 8 is shown in FIG. 4 as a non-articulating shaft. Nonetheless, applications may include instruments capable of articulation, for example, as such shown above with reference to FIGS. 1-4 and described in the following U.S. patents and patent applications, the disclosure of each being hereby incorporated by reference in their entirety: (1) U.S. Pat. No. 7,111,769, entitled SURGICAL INSTRUMENT INCORPORATING AN ARTICULATION MECHANISM HAVING ROTATION ABOUT THE LONGITUDINAL AXIS; (2) U.S. Pat. No. 6,786,382, entitled SURGICAL STAPLING INSTRUMENT INCORPORATING AN ARTICULATION JOINT FOR A FIRING BAR TRACK; (3) U.S. Pat. No. 6,981,628, entitled A SURGICAL INSTRUMENT WITH A LATERAL-MOVING ARTICULATION CONTROL; (4) U.S. Pat. No. 7,055,731, entitled SURGICAL STAPLING INSTRUMENT INCORPORATING A TAPERED FIRING BAR FOR INCREASED FLEXIBILITY AROUND THE ARTICULATION JOINT; and (5) U.S. Pat. No. 6,964,363, entitled SURGICAL STAPLING INSTRUMENT HAVING ARTICULATION JOINT SUPPORT PLATES FOR SUPPORTING A FIRING BAR.

FIGS. 42-43 show an embodiment of the handle 6 that is configured for use in a mechanically actuated endocutter along with the embodiment of the shaft 8 and end effector 12 as shown above in FIG. 41. It will be appreciated that any suitable handle design may be used to mechanically close and fire the end effector 12. In FIGS. 42-43, the handle 6 of the surgical stapling and severing instrument 10 includes a linked transmission firing mechanism 1060 that provides features such as increased strength, reduced handle size, minimized binding, etc.

Closure of the end effector 12 (not shown in FIGS. 42-43) is caused by depressing the closure trigger 18 toward the pistol grip 26 of handle 6. The closure trigger 18 pivots about a closure pivot pin 252 that is coupled to right and left exterior lower side pieces 59, 60 the handle 6, causing an upper portion 1094 of the closure trigger 18 to move forward. The closure tube 1005 receives this closure movement via the closure yoke 250 that is pinned to a closure link 1042 and to the upper portion 1094 of the closure trigger 18 respectively by a closure yoke pin 1044 and a closure link pin 1046.

In the fully open position of FIG. 42, the upper portion 1094 of the closure trigger 18 contacts and holds a locking arm 1048 of the pivoting closure release button 30 in the position shown. When the closure trigger 18 reaches its fully depressed position, the closure trigger 18 releases the locking arm 1048 and an abutting surface 1050 rotates into engagement with a distal rightward notch 1052 of the pivoting locking arm 1048, holding the closure trigger 18 in this clamped or closed position. A proximal end of the locking arm 1048 pivots about a lateral pivotal connection 1054 with the pieces 59, 60 to expose the closure release button 30. An intermediate, distal side 1056 of the closure release button 30 is urged proximally by a compression spring 1058, which is compressed between a housing structure 1040 and closure release button 30. The result is that the closure release button 30 urges the locking arm 1048 counterclockwise (when viewed from the left) into locking contact with the abutting surface 1050 of closure trigger 18, which prevents unclamping of closure trigger 18 when the linked transmission firing system 1040 is in an un-retracted condition.

With the closure trigger 18 retracted and fully depressed, the firing trigger 20 is unlocked and may be depressed toward the pistol grip 26, multiple times in this embodiment, to effect firing of the end effector 12. As depicted, the linked transmission firing mechanism 1060 is initially retracted, urged to remain in this position by a combination tension/compression spring 1062 that is constrained within the pistol grip 26 of the handle 6, with its nonmoving end 1063 connected to the pieces 59, 60 and a moving end 1064 connected to a downwardly flexed and proximal, retracted end 1067 of a steel band 1066.

A distally-disposed end 1068 of the steel band 1066 is attached to a link coupling 1070 for structural loading, which in turn is attached to a front link 1072a of a plurality of links 1072a-1072d that form a linked rack 1074. Linked rack 1074 is flexible yet has distal links that form a straight rigid rack assembly that may transfer a significant firing force through the firing rod 1010 in the shaft 6, yet readily retract into the pistol grip 26 to minimize the longitudinal length of the handle 6. It should be appreciated that the combination tension/compression spring 1062 increases the amount of firing travel available while essentially reducing the minimum length by half over a single spring.

The firing trigger 20 pivots about a firing trigger pin 96 that is connected to the handle pieces 59, 60. An upper portion 228 of the firing trigger 20 moves distally about the firing trigger pin 96 as the firing trigger 20 is depressed towards pistol grip 26, stretching a proximally placed firing trigger tension spring 222 proximally connected between the upper portion 228 of the firing trigger 20 and the pieces 59, 60. The upper portion 228 of the firing trigger 20 engages the linked rack 1074 during each firing trigger depression by a traction biasing mechanism 1078 that also disengages when the firing trigger 20 is released. Firing trigger tension spring 222 urges the firing trigger 20 distally when released and disengages the traction biasing mechanism 1078.

As the linked transmission firing mechanism 1040 actuates, an idler gear 1080 is rotated clockwise (as viewed from the left side) by engagement with a toothed upper surface 1082 of the linked rack 1074. This rotation is coupled to an indicator gear 1084, which thus rotates counterclockwise in response to the idler gear 1080. Both the idler gear 1080 and indicator gear 1084 are rotatably connected to the pieces 59, 60 of the handle 6. The gear relationship between the linked rack 1074, idler gear 1080 and indicator gear 1084 may be advantageously selected so that the toothed upper surface 1082 has tooth dimensions that are suitably strong and that the indicator gear 1084 makes no more than one revolution during the full firing travel of the linked transmission firing mechanism 1060.

As described in greater detail below, the indicator gear 1084 performs at least four functions. First, when the linked rack 1074 is fully retracted and both triggers 18, 20 are open as shown in FIG. 42, an opening 1086 in a circular ridge 1088 on the left side of the indicator gear 1084 is presented to an upper surface 1090 of the locking arm 1048. Locking arm 1048 is biased into the opening 1086 by contact with the closure trigger 18, which in turn is urged to the open position by a closure tension spring 1092. Closure trigger tension spring 1092 is connected proximally to the upper portion 1094 of the closure trigger 18 and the handle pieces 59, 60, and thus has energy stored during closing of the closure trigger 18 that urges the closure trigger 18 distally to its unclosed position.

A second function of the indicator gear 1084 is that it is connected to the indicating retraction knob 1096 externally disposed on the handle 6. Thus, the indicator gear 1084 communicates the relative position of the firing mechanism 1060 to the indicating retraction knob 1096 so that the surgeon has a visual indication of how many strokes of the firing trigger 20 are required to complete firing.

A third function of the indicator gear 1084 is to longitudinally and angularly move an anti-backup release lever 1098 of an anti-backup mechanism (one-way clutch mechanism) 1097 as the surgical stapling and severing instrument 10 is operated. During the firing strokes, proximal movement of anti-backup release lever 1098 by indicator gear 1084 activates the anti-backup mechanism 1097 that allows distal movement of firing bar 1010 and prevents proximal motion of firing bar 1010. This movement also extends the anti-backup release button 1100 from the proximal end of the handle pieces 59, 60 for the operator to actuate should the need arise for the linked transmission firing mechanism 1060 to be retracted during the firing strokes. After completion of the firing strokes, the indicator gear 1084 reverses direction of rotation as the firing mechanism 1060 retracts. The reversed rotation deactivates the anti-backup mechanism 1097, withdraws the anti-backup release button 1100 into the handle 6, and rotates the anti-backup release lever 1098 laterally to the right to allow continued reverse rotation of the indicator gear 1084.

A fourth function of the indicator gear 1084 is to receive a manual rotation from the indicating retraction knob 1096 (clockwise in the depiction of FIG. 42) to retract the firing mechanism 1060 with anti-backup mechanism 1097 unlocked, thereby overcoming any binding in the firing mechanism 1060 that is not readily overcome by the combination tension/compression spring 1062. This manual retraction assistance may be employed after a partial firing of the firing mechanism 1060 that would otherwise be prevented by the anti-backup mechanism 1097 that withdraws the anti-backup release button 1100 so that the latter may not laterally move the anti-backup release lever 1098.

Continuing with FIGS. 42-43, anti-backup mechanism 1097 consists of the operator accessible anti-backup release lever 1098 operably coupled at the proximal end to the anti-backup release button 1100 and at the distal end to an anti-backup yoke 1102. In particular, a distal end 1099 of the anti-backup release lever 1098 is engaged to the anti-backup yoke 1102 by an anti-backup yoke pin 1104. The anti-backup yoke 1102 moves longitudinally to impart a rotation to an anti-backup cam slot tube 1106 that is longitudinally constrained by the handle pieces 59, 90 and that encompasses the firing rod 1010 distally to the connection of the firing rod 1010 to the link coupling 1070 of the linked rack 1074. The anti-backup yoke 1102 communicates the longitudinal movement from the anti-backup release lever 1098 via a cam slot tube pin 1108 to the anti-backup cam slot tube 1106. That is, longitudinal movement of cam slot tube pin 1108 in an angled slot in the anti-backup cam slot tube 1106 rotates the anti-backup cam slot tube 1106.

Trapped between a proximal end of the frame 1016 and the anti-backup cam slot tube 1106 respectively are an anti-backup compression spring 1110, an anti-backup plate 1112, and an anti-backup cam tube 1114. As depicted, proximal movement of the firing rod 1010 causes the anti-backup plate 1112 to pivot top to the rear, presenting an increased frictional contact to the firing rod 1010 that resists further proximal movement of the firing rod 1010.

This anti-backup plate 1112 pivots in a manner similar to that of a screen door lock that holds open a screen door when the anti-backup cam slot tube 1106 is closely spaced to the anti-backup cam tube 1114. Specifically, the anti-backup compression spring 1110 is able to act upon a top surface of the plate 1112 to tip the anti-backup plate 1112 to its locked position. Rotation of the anti-backup cam slot tube 1106 causes a distal camming movement of the anti-backup cam tube 1114 thereby forcing the top of the anti-backup plate 1112 distally, overcoming the force from the anti-backup compression spring 1110, thus positioning the anti-backup plate 1112 in an untipped (perpendicular), unlocked position that allows proximal retraction of the firing rod 1010.

With particular reference to FIG. 43, the traction biasing mechanism 1078 is depicted as being composed of a pawl 1116 that has a distally projecting narrow tip 1118 and a rightwardly projecting lateral pin 1120 at its proximal end that is rotatably inserted through a hole 1076 in the upper portion 230 of the firing trigger 20. On the right side of the firing trigger 20 the lateral pin 1120 receives a biasing member, depicted as biasing wheel 1122. As the firing trigger 20 translates fore and aft, the biasing wheel 1122 traverses an arc proximate to the right half piece 59 of the handle 6, overrunning at its distal portion of travel a biasing ramp 1124 integrally formed in the right half piece 59. The biasing wheel 1122 may advantageously be formed from a resilient, frictional material that induces a counterclockwise rotation (when viewed from the left) into the lateral pin 1120 of the pawl 1116, thus traction biasing the distally projecting narrow tip 1118 downward into a ramped central track 1075 of the nearest link 1072*a-d* to engage the linked rack 1074.

As the firing trigger 20 is released, the biasing wheel 1122 thus tractionally biases the pawl 1116 in the opposite direction, raising the narrow tip 1118 from the ramped central track 1075 of the linked rack 1074. To ensure disengagement of the tip 1118 under high load conditions and at nearly full distal travel of the pawl 1116, the right side of the pawl 1116 ramps up onto a proximally and upwardly facing beveled surface 1126 on the rightside of the closure yoke 250 to disengage the narrow tip 1118 from the ramped central track 1075. If the firing trigger 20 is released at any point other than full travel, the biasing wheel 1122 is used to lift the narrow tip 1118 from the ramped central track 1075. Whereas a biasing wheel 1122 is depicted, it should be appreciated that the shape of the biasing member or wheel 1122 is illustrative and may be varied to accommodate a variety of shapes that use friction or traction to engage or disengage the firing of the end effector 12.

Figure 44:
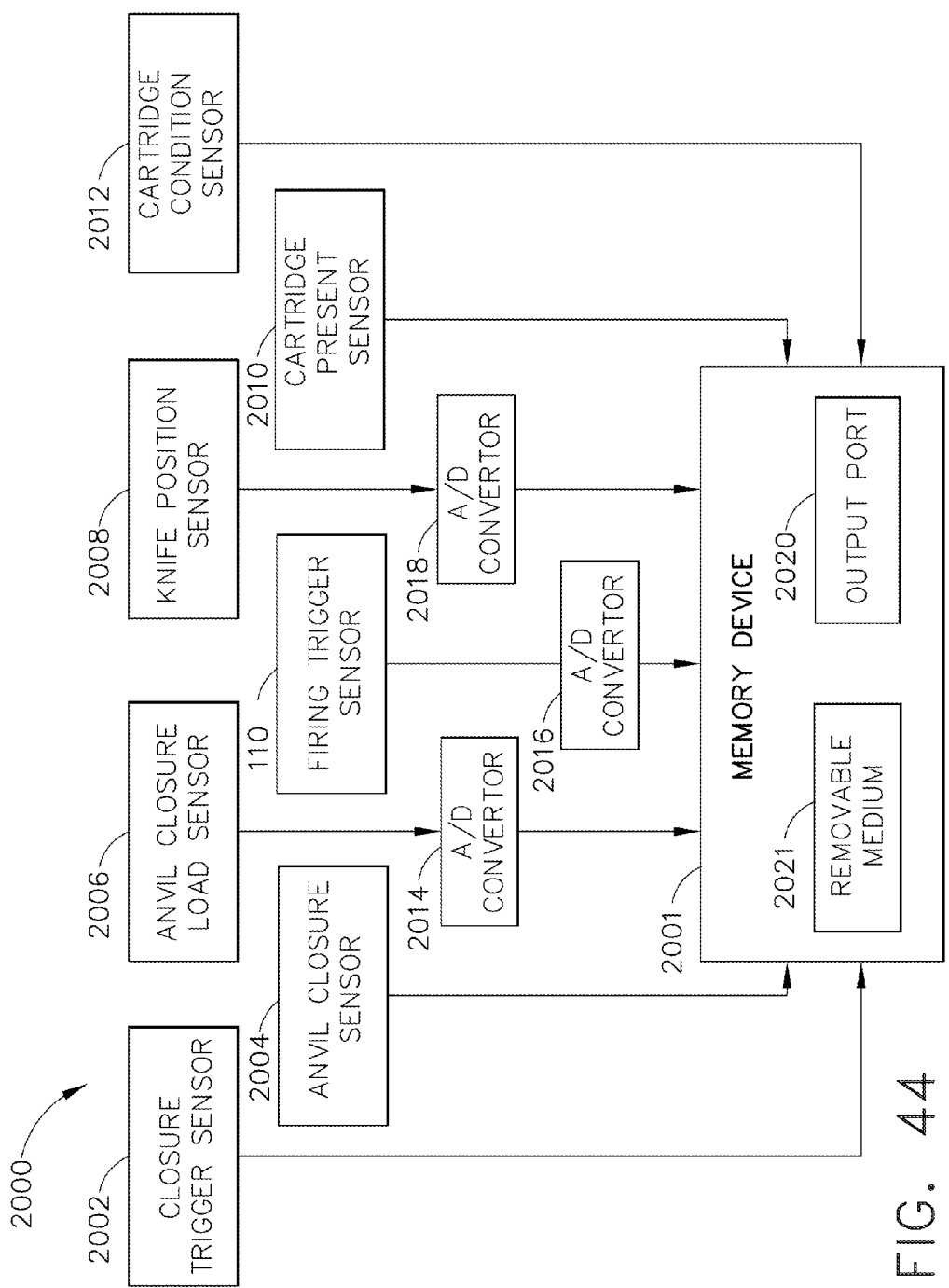
FIG. 44 illustrates a block diagram of a recording system for recording various conditions of a surgical instrument.

Various embodiments of the surgical instrument 10 have the capability to record instrument conditions at one or more times during use. FIG. 44 shows a block diagram of a system 2000 for recording conditions of the instrument 10. It will be appreciated that the system 2000 may be implemented in embodiments of the instrument 10 having motorized or motor-assisted firing, for example, as described above with reference to FIGS. 1-40, as well as embodiments of the instrument 10 having mechanically actuated firing, for example, as described above with reference to FIGS. 41-43.

The system 2000 may include various sensors 2002, 2004, 2006, 2008, 2010, 2012 for sensing instrument conditions. The sensors may be positioned, for example, on or within the instrument 10. In various embodiments, the sensors may be dedicated sensors that provide output only for the system 2000, or may be dual-use sensors that perform other functions within the instrument 10. For example, sensors 110, 130, 142 described above may be configured to also provide output to the system 2000.

Directly or indirectly, each sensor provides a signal to the memory device 2001, which records the signals as described in more detail below. The memory device 2001 may be any kind of device capable of storing or recording sensor signals. For example, the memory device 2001 may include a microprocessor, an Electrically Erasable Programmable Read Only Memory (EEPROM), or any other suitable storage device. The memory device 2001 may record the signals provided by the sensors in any suitable way. For example, in one embodiment, the memory device 2001 may record the signal from a particular sensor when that signal changes states. In another embodiment, the memory device 2001 may record a state of the system 2000, e.g., the signals from all of the sensors included in the system 2000, when the signal from any sensor changes states. This may provide a snap-shot of the state of the instrument 10. In various embodiments, the memory device 2001, and/or sensors may be implemented to include 1-WIRE bus products available from DALLAS SEMICONDUCTOR such as, for example, a 1-WIRE EEPROM.

In various embodiments, the memory device 2001 is externally accessible, allowing an outside device, such as a computer, to access the instrument conditions recorded by the memory device 2001. For example, the memory device 2001 may include a data port 2020. The data port 2020 may provide the stored instrument conditions according to any wired or wireless communication protocol in, for example, serial or parallel format. The memory device 2001 may also include a removable medium 2021 in addition to or instead of the output port 2020. The removable medium 2021 may be any kind of suitable data storage device that can be removed from the instrument 10. For example, the removable medium 2021 may include any suitable kind of flash memory, such as a Personal Computer Memory Card International Association (PCMCIA) card, a COMPACTFLASH card, a MULTIMEDIA card, a FLASHMEDIA card, etc. The removable medium 2021 may also include any suitable kind of disk-based storage including, for example, a portable hard drive, a compact disk (CD), a digital video disk (DVD), etc.

Figure 45:
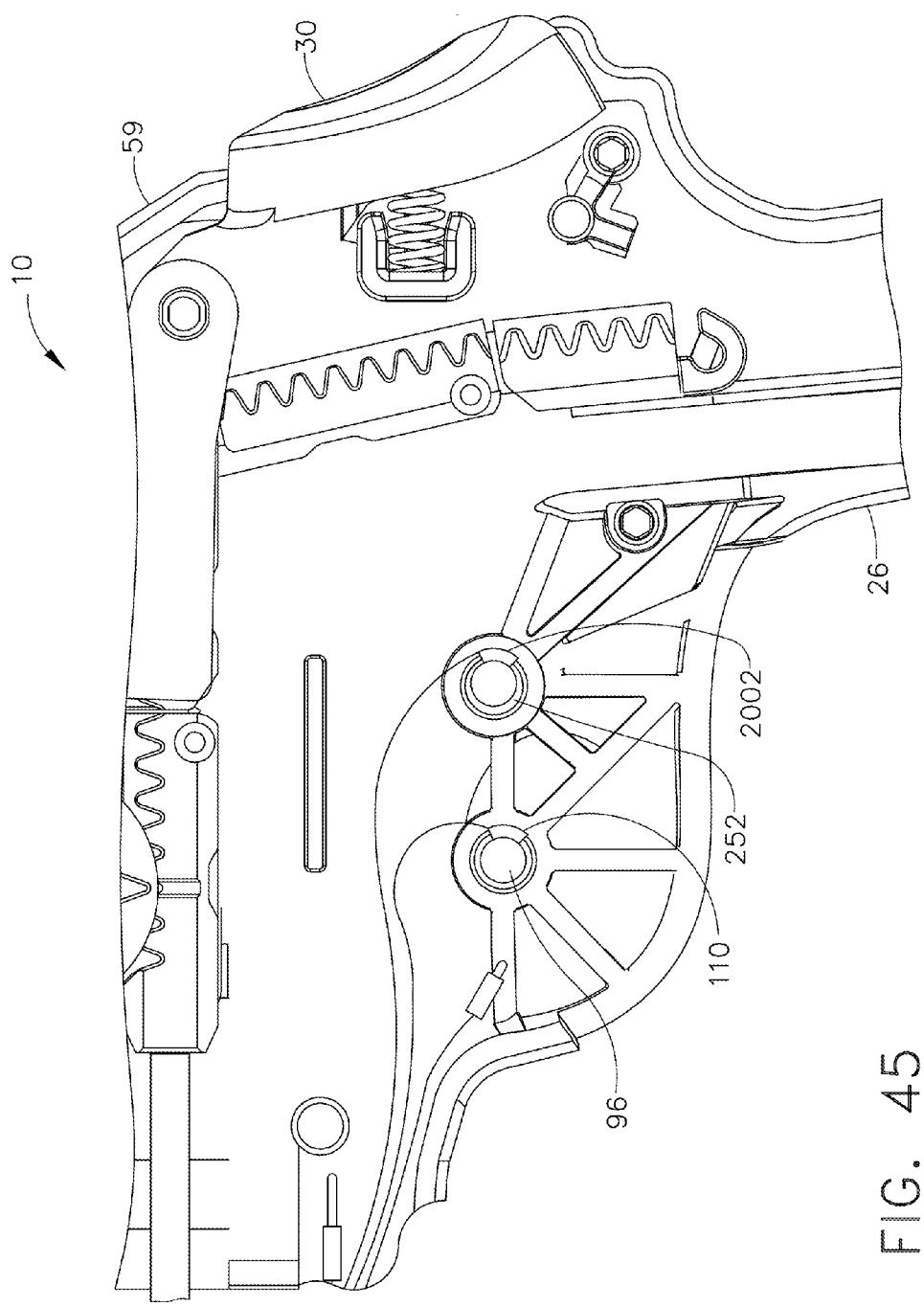
FIGS. 45-46 illustrate cut away side views of a handle of the instrument of FIG. 42.
Figure 46:
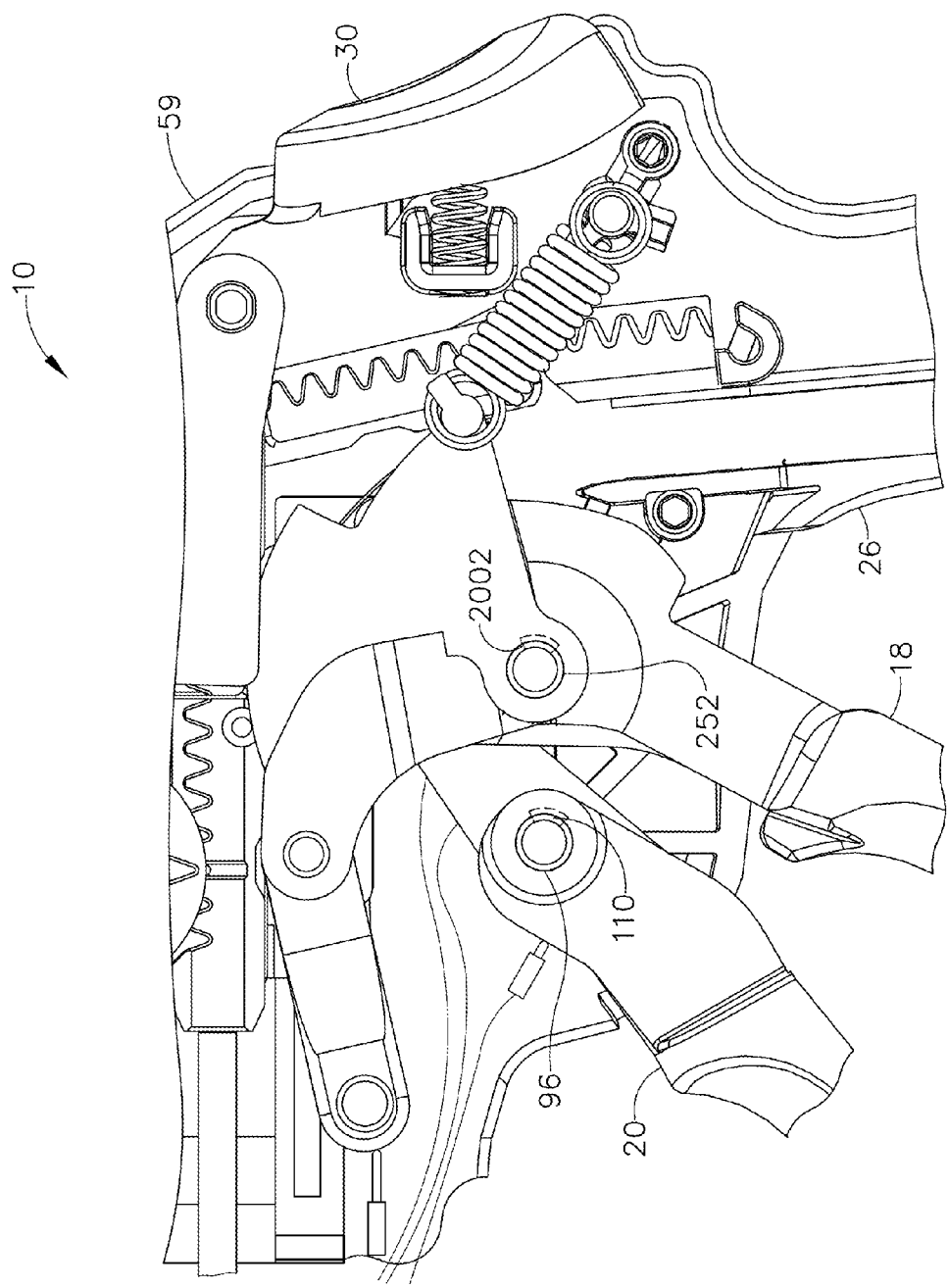

The closure trigger sensor 2002 senses a condition of the closure trigger 18. FIGS. 45 and 46 show an exemplary embodiment of the closure trigger sensor 2002. In FIGS. 45 and 46, the closure trigger sensor 2002 is positioned between the closure trigger 18 and closure pivot pin 252. It will be appreciated that pulling the closure trigger 18 toward the pistol grip 26 causes the closure trigger 18 to exert a force on the closure pivot pin 252. The sensor 2002 may be sensitive to this force, and generate a signal in response thereto, for example, as described above with respect to sensor 110 and FIGS. 10A and 10B. In various embodiments, the closure trigger sensor 2002 may be a digital sensor that indicates only whether the closure trigger 18 is actuated or not actuated. In other various embodiments, the closure trigger sensor 2002 may be an analog sensor that indicates the force exerted on the closure trigger 18 and/or the position of the closure trigger 18. If the closure trigger sensor 2002 is an analog sensor, an analog-to-digital converter may be logically positioned between the sensor 2002 and the memory device 2001. Also, it will be appreciated that the closure trigger sensor 2002 may take any suitable form and be placed at any suitable location that allows sensing of the condition of the closure trigger.

Figure 47:
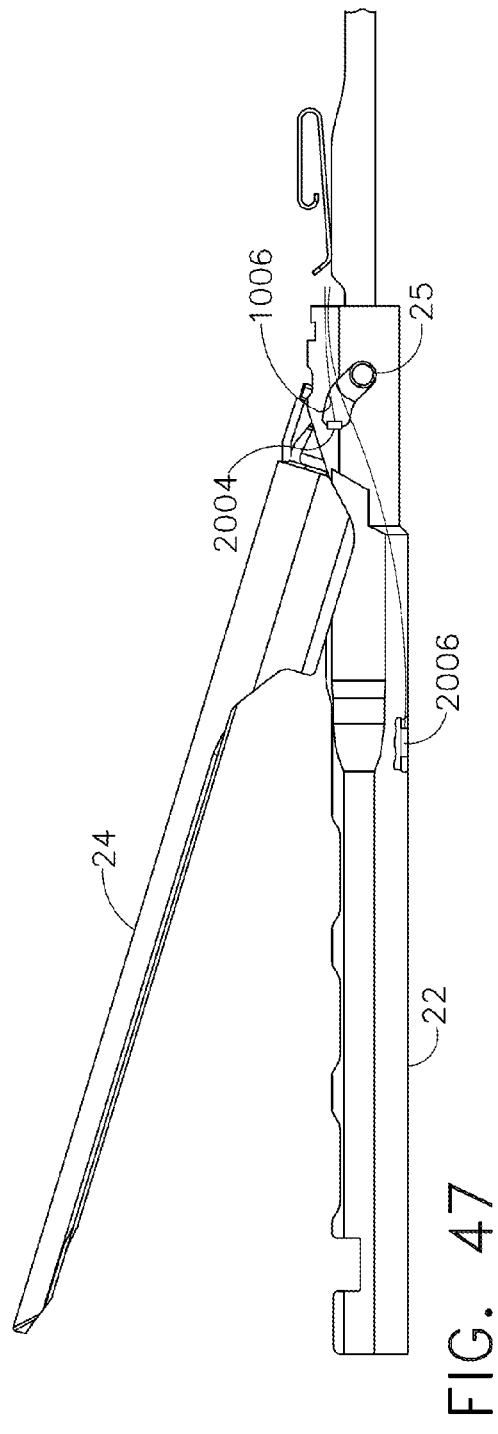
FIG. 47 illustrates the end effector of the instrument of FIG. 42 showing various sensors.

The anvil closure sensor 2004 may sense whether the anvil 24 is closed. FIG. 47 shows an exemplary anvil closure sensor 2004. The sensor 2004 is positioned next to, or within the kidney shaped openings 1006 of the staple channel 22 as shown. As the anvil 24 is closed, anvil pivot pins 25 slides through the kidney shaped openings 1006 and into contact with the sensor 2004, causing the sensor 2004 to generate a signal indicating that the anvil 24 is closed. The sensor 2004 may be any suitable kind of digital or analog sensor including a proximity sensor, etc. It will be appreciated that when the anvil closure sensor 2004 is an analog sensor, an analog-to-digital converter may be included logically between the sensor 2004 and the memory device 2001.

Anvil closure load sensor 2006 is shown placed on an inside bottom surface of the staple channel 22. In use, the sensor 2006 may be in contact with a bottom side of the staple cartridge 34 (not shown in FIG. 46). As the anvil 24 is closed, it exerts a force on the staple cartridge 34 which is transferred to the sensor 2006. In response, the sensor 2006 generates a signal. The signal may be an analog signal proportional to the force exerted on the sensor 2006 by the staple cartridge 34 and due to the closing of the anvil 24. Referring the FIG. 44, the analog signal may be provided to an analog-to-digital converter 2014, which converts the analog signal to a digital signal before providing it to the memory device 2001. It will be appreciated that embodiments where the sensor 2006 is a digital or binary sensor may not include analog-to-digital converter 2014.

The firing trigger sensor 110 senses the position and/or state of the firing trigger 20. In motorized or motor-assisted embodiments of the instrument, the firing trigger sensor may double as the run motor sensor 110 described above. In addition, the firing trigger sensor 110 may take any of the forms described above, and may be analog or digital. FIGS. 45 and 46 show an additional embodiment of the firing trigger sensor 110. In FIGS. 45 and 46, the firing trigger sensor is mounted between firing trigger 20 and firing trigger pivot pin 96. When firing trigger 20 is pulled, it will exert a force on firing trigger pivot pin 96 that is sensed by the sensor 110. Referring to FIG. 44, In embodiments where the output of the firing trigger sensor 110 is analog, analog-to-digital converter 2016 is included logically between the firing trigger sensor 110 and the memory device 2001.

Figure 48:
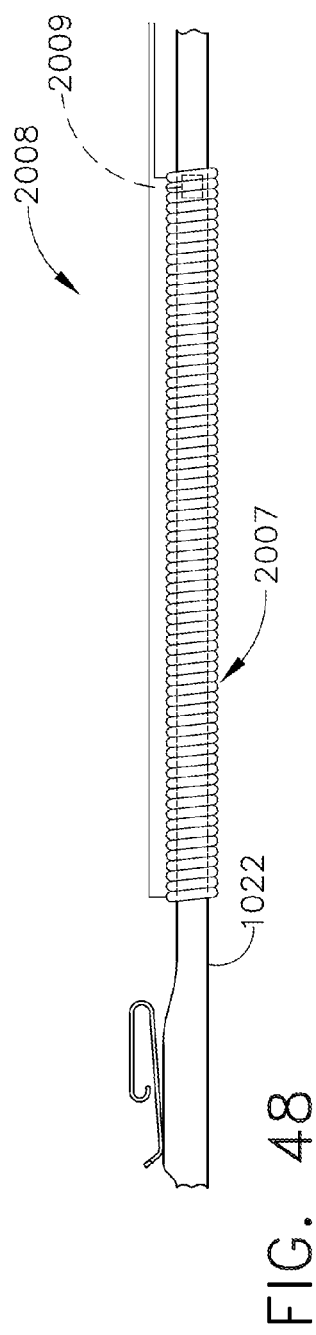
FIG. 48 illustrates a firing bar of the instrument of FIG. 42 including a sensor.

The knife position sensor 2008 senses the position of the knife 32 or cutting surface 1027 within the staple channel 22. FIGS. 49 and 48 show embodiments of a knife position sensor 2008 that are suitable for use with the mechanically actuated shaft 8 and end effector 12 shown in FIG. 41. The sensor 2008 includes a magnet 2009 coupled to the firing bar 1022 of the instrument 10. A coil 2011 is positioned around the firing bar 1022, and may be installed; for example, along the longitudinal recess 1014 of the firing trough member 1012 (see FIG. 41). As the knife 32 and cutting surface 1027 are reciprocated through the staple channel 22, the firing bar 1022 and magnet 2009 may move back and forth through the coil 2007. This motion relative to the coil induces a voltage in the coil proportional to the position of the firing rod within the coil and the cutting edge 1027 within the staple channel 22. This voltage may be provided to the memory device 2001, for example, via analog-to-digital converter 2018.

In various embodiments, the knife position sensor 2008 may instead be implemented as a series of digital sensors (not shown) placed at various positions on or within the shaft 8. The digital sensors may sense a feature of the firing bar 1022 such as, for example, magnet 2009, as the feature reciprocates through the shaft 8. The position of the firing bar 1022 within the shaft 8, and by extension, the position of the knife 32 within the staple channel 22, may be approximated as the position of the last digital sensor tripped.

It will be appreciated that the knife position may also be sensed in embodiments of the instrument 10 having a rotary driven end effector 12 and shaft 8, for example, as described above, with reference to FIGS. 3-6. An encoder, such as encoder 268, may be configured to generate a signal proportional to the rotation of the helical screw shaft 36, or any other drive shaft or gear. Because the rotation of the shaft 36 and other drive shafts and gears is proportional to the movement of the knife 32 through the channel 22, the signal generated by the encoder 268 is also proportional to the movement of the knife 32. Thus, the output of the encoder 268 may be provided to the memory device 2001.

The cartridge present sensor 2010 may sense the presence of the staple cartridge 34 within the staple channel 22. In motorized or motor-assisted instruments, the cartridge present sensor 2010 may double as the cartridge lock-out sensor 136 described above with reference to FIG. 11. FIGS. 50 and 51 show an embodiment of the cartridge present sensor 2010. In the embodiment shown, the cartridge present sensor 2010 includes two contacts, 2011 and 2013. When no cartridge 34 is present, the contacts 2011, 2013 form an open circuit. When a cartridge 34 is present, the cartridge tray 1028 of the staple cartridge 34 contacts the contacts 2011, 2013, a closed circuit is formed. When the circuit is open, the sensor 2010 may output a logic zero. When the circuit is closed, the sensor 2010 may output a logic one. The output of the sensor 2010 is provided to memory device 2001, as shown in FIG. 44.

The cartridge condition sensor 2012 may indicate whether a cartridge 34 installed within the staple channel 22 has been fired or spent. As the knife 32 is translated through the end effector 12, it pushes the sled 33, which fires the staple cartridge. Then the knife 32 is translated back to its original position, leaving the sled 33 at the distal end of the cartridge. Without the sled 33 to guide it, the knife 32 may fall into lock-out pocket 2022. Sensor 2012 may sense whether the knife 32 is present in the lock-out pocket 2022, which indirectly indicates whether the cartridge 34 has been spent. It will be appreciated that in various embodiments, sensor 2012 may directly sense the presence of the sled at the proximal end of the cartridge 34, thus eliminating the need for the knife 32 to fall into the lock-out pocket 2022.

Figure 52A:
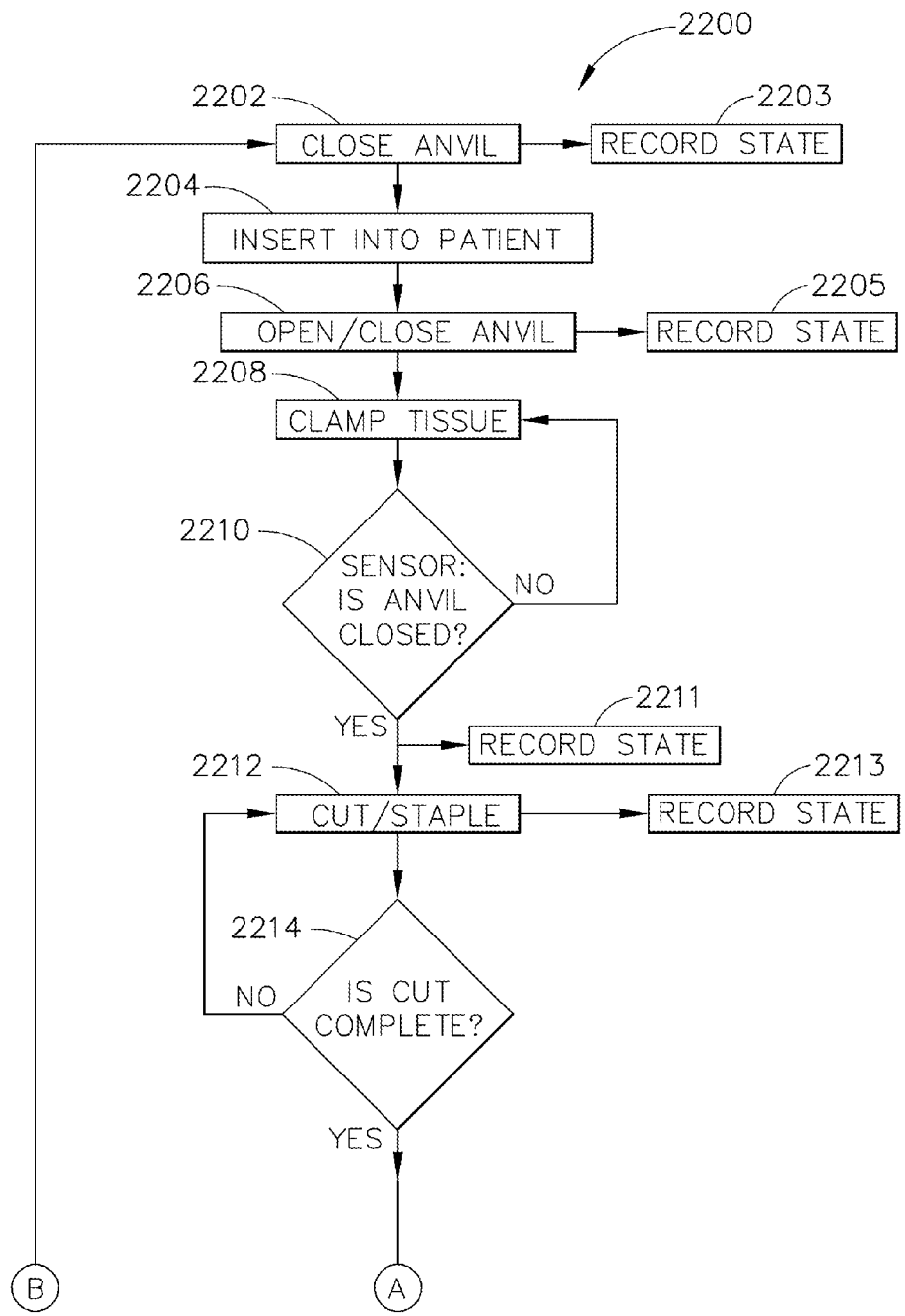
FIGS. 52A and 52B illustrate a flow chart showing a method for operating a surgical instrument according to various embodiments.
Figure 52B:
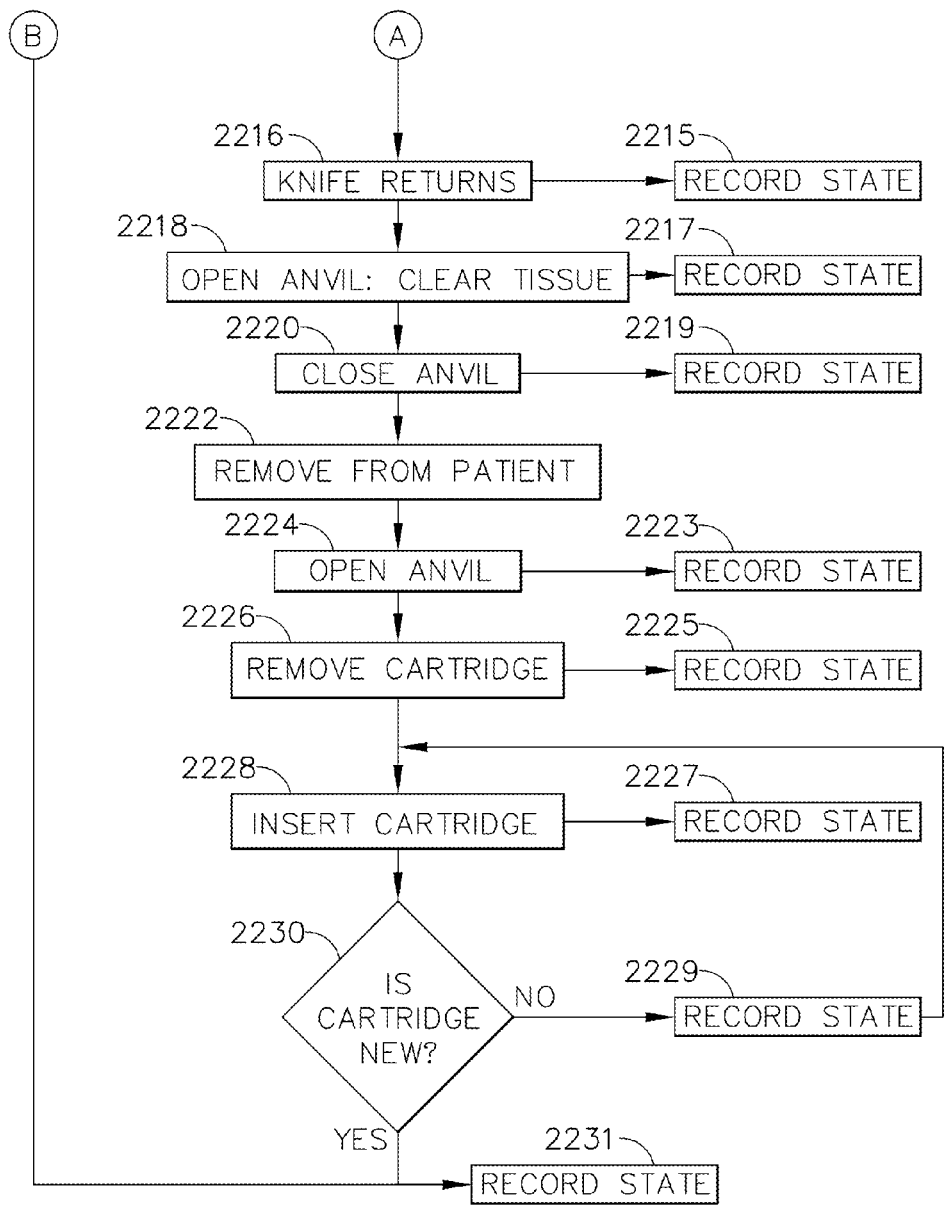

FIGS. 52A and 52B depict a process flow 2200 for operating embodiments of the surgical instrument 10 configured as an endocutter and having the capability to record instrument conditions according to various embodiments. At box 2202, the anvil 24 of the instrument 10 may be closed. This causes the closure trigger sensor 2002 and or the anvil closure sensor 2006 to change state. In response, the memory device 2001 may record the state of all of the sensors in the system 2000 at box 2203. At box 2204, the instrument 10 may be inserted into a patient. When the instrument is inserted, the anvil 24 may be opened and closed at box 2206, for example, to manipulate tissue at the surgical site. Each opening and closing of the anvil 24 causes the closure trigger sensor 2002 and/or the anvil closure sensor 2004 to change state. In response, the memory device 2001 records the state of the system 2000 at box 2205.

At box 2208, tissue is clamped for cutting and stapling. If the anvil 24 is not closed at decision block 2210, continued clamping is required. If the anvil 24 is closed, then the sensors 2002, 2004 and/or 2006 may change state, prompting the memory device 2001 to record the state of the system at box 2211. This recording may include a closure pressure received from sensor 2006. At box 2212, cutting and stapling may occur. Firing trigger sensor 110 may change state as the firing trigger 20 is pulled toward the pistol grip 26. Also, as the knife 32 moves through the staple channel 22, knife position sensor 2008 will change state. In response, the memory device 2001 may record the state of the system 2000 at box 2211.

When the cutting and stapling operations are complete at decision box 2214, the knife 32 may return to a pre-firing position at box 2216. Because the cartridge 34 has now been fired, the knife 32 may fall into lock-out pocket 2022, changing the state of cartridge condition sensor 2012 and triggering the memory device 2001 to record the state of the system 2000 at box 2215. The anvil 24 may then be opened to clear the tissue at box 2218. This may cause one or more of the closure trigger sensor 2002, anvil closure sensor 2004 and anvil closure load sensor 2006 to change state, resulting in a recordation of the state of the system 2000 at box 2217. After the tissue is cleared, the anvil 24 may be again closed at box 2220. This causes another state change for at least sensors 2002 and 2004, which in turn causes the memory device 2001 to record the state of the system at box 2219. Then the instrument 10 may be removed from the patient at box 2222.

If the instrument 10 is to be used again during the same procedure, the anvil may be opened at box 2224, triggering another recordation of the system state at box 2223. The spent cartridge 34 may be removed from the end effector 12 at box 2226. This causes cartridge present sensor 2010 to change state and cause a recordation of the system state at box 2225. Another cartridge 34 may be inserted at box 2228. This causes a state change in the cartridge present sensor 2010 and a recordation of the system state at box 2227. If the other cartridge 34 is a new cartridge, indicated at decision block 2230, its insertion may also cause a state change to cartridge condition sensor 2012. In that case, the system state may be recorded at box 2229 or 2231.

FIG. 53 shows an exemplary memory map 2300 from the memory device 2001 according to various embodiments. The memory map 2300 includes a series of columns 2302, 2304, 2306, 2308, 2310, 2312, 2314, 2316 and rows (not labeled). Column 2302 shows an event number for each of the rows. The other columns represent the output of one sensor of the system 2000. All of the sensor readings recorded at a given time may be recorded in the same row under the same event number. Hence, each row represents an instance where one or more of the signals from the sensors of the system 2000 are recorded.

Column 2304 lists the closure load recorded at each event. This may reflect the output of anvil closure load sensor 2006. Column 2306 lists the firing stroke position. This may be derived from the knife position sensor 2008. For example, the total travel of the knife 32 may be divided into partitions. The number listed in column 2306 may represent the partition where the knife 32 is currently present. The firing load is listed in column 2308. This may be derived from the firing trigger sensor 110. The knife position is listed at column 2310. The knife position may be derived from the knife position sensor 2008 similar to the firing stroke. Whether the anvil 24 is open or closed may be listed at column 2312. This value may be derived from the output of the anvil closure sensor 2004 and/or the anvil closure load sensor 2006. Whether the sled 33 is present, or whether the cartridge 34 is spent, may be indicated at column 2314. This value may be derived from the cartridge condition sensor 2012. Finally, whether the cartridge 34 is present may be indicated a column 2316. This value may be derived from cartridge present sensor 2010. It will be appreciated that various other values may be stored at memory device 2001 including, for example, the end and beginning of firing strokes, for example, as measured by sensors 130, 142.

Figure 54:
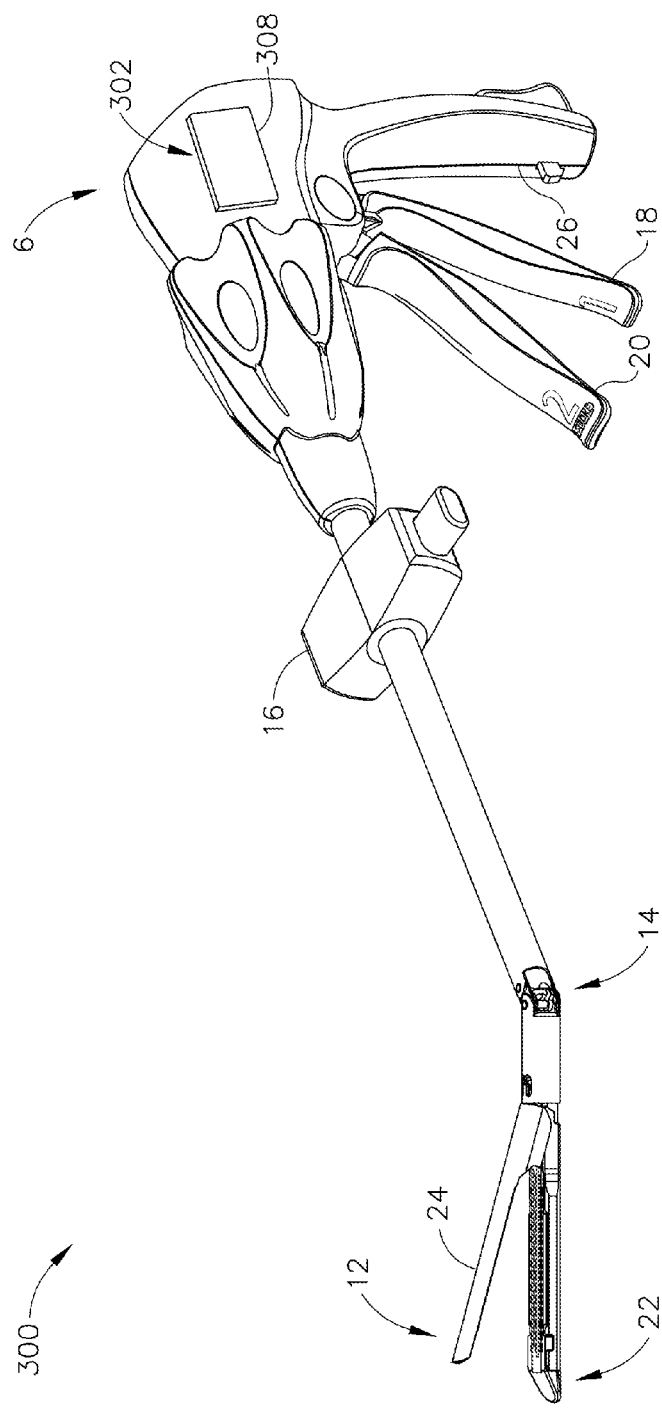
FIG. 54 illustrates a surgical instrument according to various embodiments.

FIG. 54 illustrates various embodiments of a surgical instrument 300. The surgical instrument 300 may be similar to the surgical instrument 10 described hereinabove, but also includes a status module 302 releasably connected thereto. Although the status module 302 is shown in FIG. 54 as being connected to the exterior lower side piece 60 of the handle 6, it is understood that the status module 302 may be connected to the surgical instrument 300 at any suitable location. According to various embodiments, the handle 6 of the surgical instrument 300 defines a recess structured and arranged to receive the status module 302.

The surgical instrument 300 comprises a plurality of sensors 304 (shown schematically in FIG. 55), wherein the plurality of sensors 304 includes, for example, an articulation angle sensor, an anvil position sensor, a cartridge sensor, a closure trigger sensor, a closure force sensor, a firing force sensor, a knife position sensor, a lockout condition sensor, or any combination thereof. Each sensor 304 may be in electrical communication with a different contact 306 (shown schematically in FIG. 55) positioned proximate the exterior of the surgical instrument 300.

The sensors 304 may be embodied in any suitable manner. For example, the articulation angle sensor may be embodied as, for example, a potentiometer that comprises a portion of the articulation control 16 and outputs a signal that indicates the relative articulation angle of the end effector 12. The anvil position sensor may be embodied as, for example, the anvil closure sensor 2004 described above; the cartridge sensor may be embodied as, for example, the cartridge present sensor 2010 described above; the closure trigger sensor may be embodied as, for example, the closure trigger sensor 2002 described above; the closure force sensor may be embodied as, for example, the anvil closure load sensor 2006 described above; the firing force sensor may be embodied as, for example, the firing trigger sensor 110 described above; the knife position sensor may be embodied as, for example, the knife position sensor 2008 described above; and the lockout condition sensor may be embodied as, for example, the cartridge lockout sensor 136 or the cartridge present sensor 2010 described above. Various embodiments of surgical instruments are disclosed in U.S. patent application Ser. No. 11/343,803, entitled SURGICAL INSTRUMENT HAVING RECORDING CAPABILITIES, the entire disclosure of which is incorporated by reference herein.

According to various embodiments, the status module 302 comprises a housing 308 structured and arranged to releasably connect to the surgical instrument 300. The status module 308 comprises a plurality of contacts 310 (shown schematically in FIG. 55), wherein each individual contact 310 is structured and arranged to be in electrical communication with a different sensor 304 of the surgical instrument 300 when the housing 308 is connected to the surgical instrument 300. For example, when the status module 302 is connected to the surgical instrument 300, each contact 310 of the status module 302 may be aligned with a respective corresponding contact 306 of the surgical instrument 300, thereby placing each contact 310 of the status module 302 in electrical communication with a different sensor 304.

Figure 55:
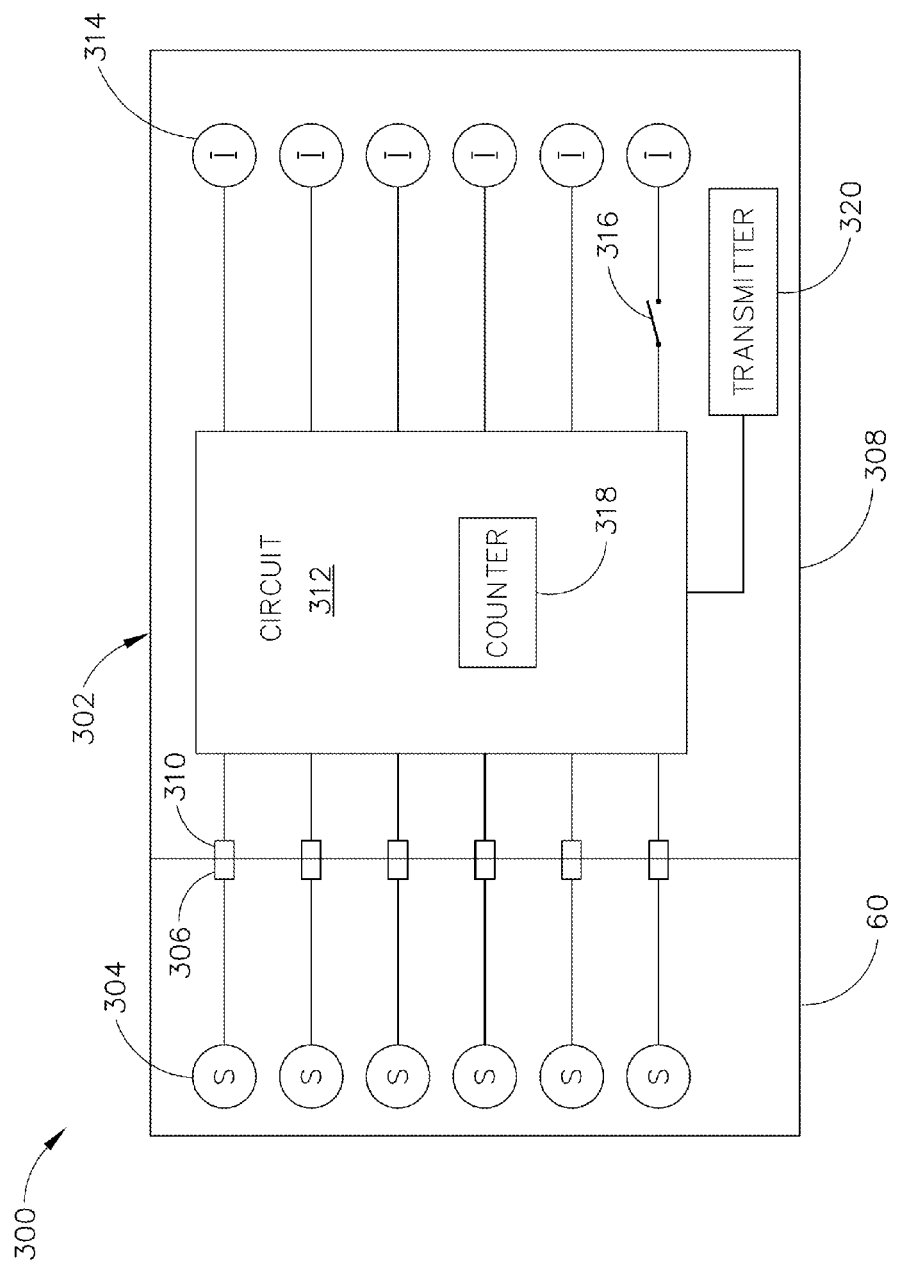
FIG. 55 is a schematic diagram of the surgical instrument of FIG. 54.

The status module 302 further comprises a circuit 312 (shown schematically in FIG. 55) in communication with at least one of the contacts 310, and a plurality of indicators 314 (shown schematically in FIG. 55). At least one of the indicators 314 is in electrical communication with the circuit 312. The circuit 312 comprises a drive circuit, and is structured and arranged to drive at least one of the indicators 314. According to various embodiments, the circuit 312 may further comprise, as shown schematically in FIG. 55, a switch 316, a counter 318, a transmitter 320, or any combination thereof.

The switch 316 is in electrical communication with at least one of the indicators 314, and may be utilized to disable the respective indicator 314 that is in electrical communication therewith. According to various embodiments, the switch 316 may comprise a portion of the status module 302 other than the circuit 312, or a portion of the surgical instrument 300 other than the status module 302. For such embodiments, the switch 316 may be in electrical communication with the circuit 312.

The counter 318 may be utilized to determine the number of firings, the number of firings remaining, the post-clamping wait time, etc. According to various embodiments, the counter 318 may comprise a portion of the status module 302 other than the circuit 312. According to other embodiments, the counter 318 may comprise a portion of the surgical instrument 300 other than the status module 302. For such embodiments, the counter 318 may be in electrical communication with the circuit 312.

The transmitter 320 may be utilized to wirelessly transmit information sensed by the plurality of sensors 304 to a wireless receiver (not shown) associated with a monitor (not shown) that may be viewed by a user of the surgical instrument 300 while the user is performing a procedure. The information may be wirelessly transmitted continuously or periodically. The displayed information may include, for example, firing progress information, compression load information, knife load information, number of firings, procedure time, compression wait time, battery level, etc. According to other various embodiments, the transmitter 320 may comprise a portion of the status module 302 other than the circuit 312, or a portion of the surgical instrument 300 other than the status module 302. For such embodiments, the transmitter 320 may be in electrical communication with the circuit 312.

Figure 56:
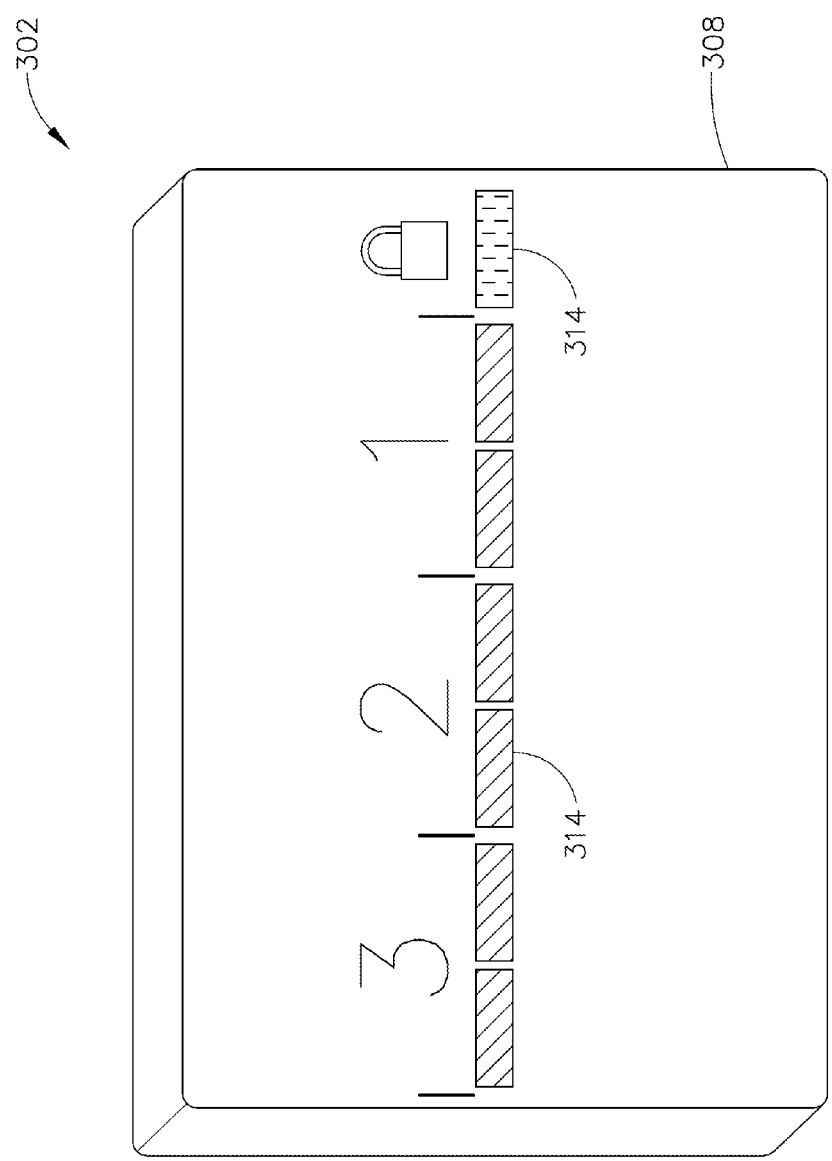
FIGS. 56-58 illustrate various embodiments of a portion of the surgical instrument of FIG. 54.
Figure 57:
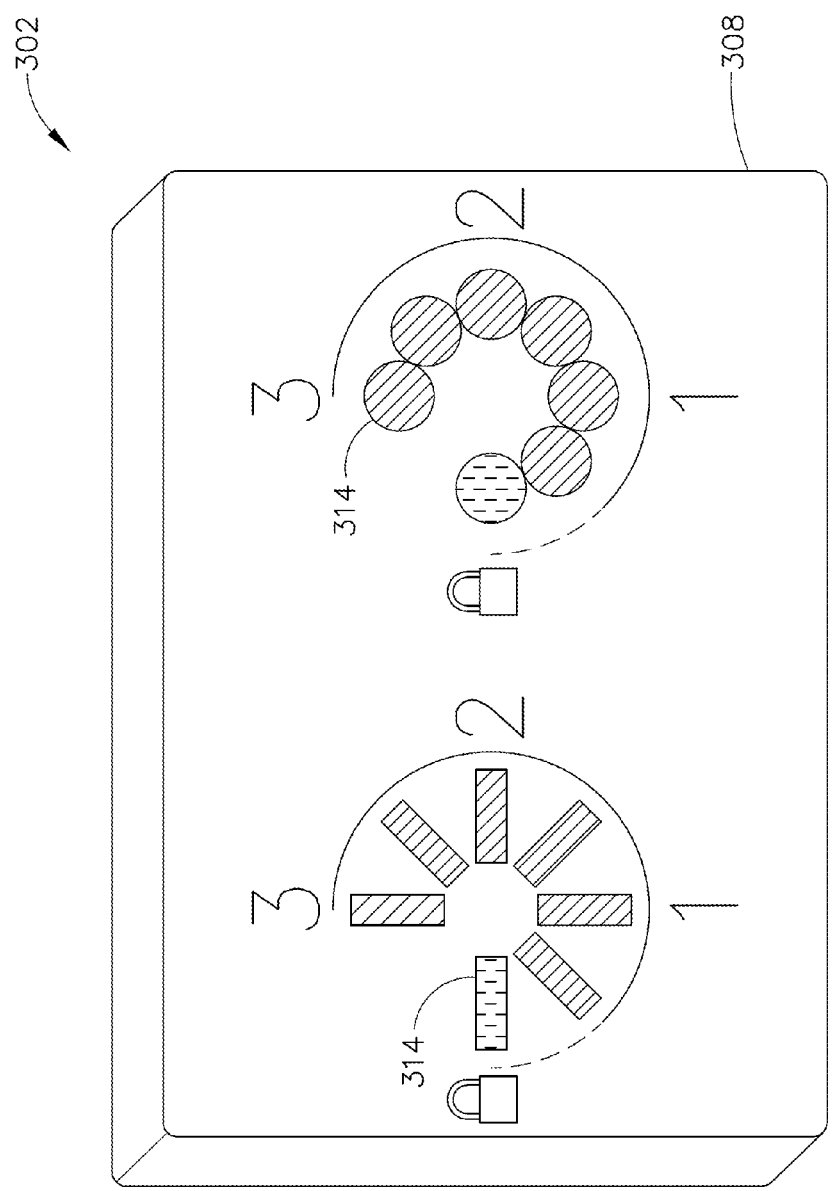
Figure 58:
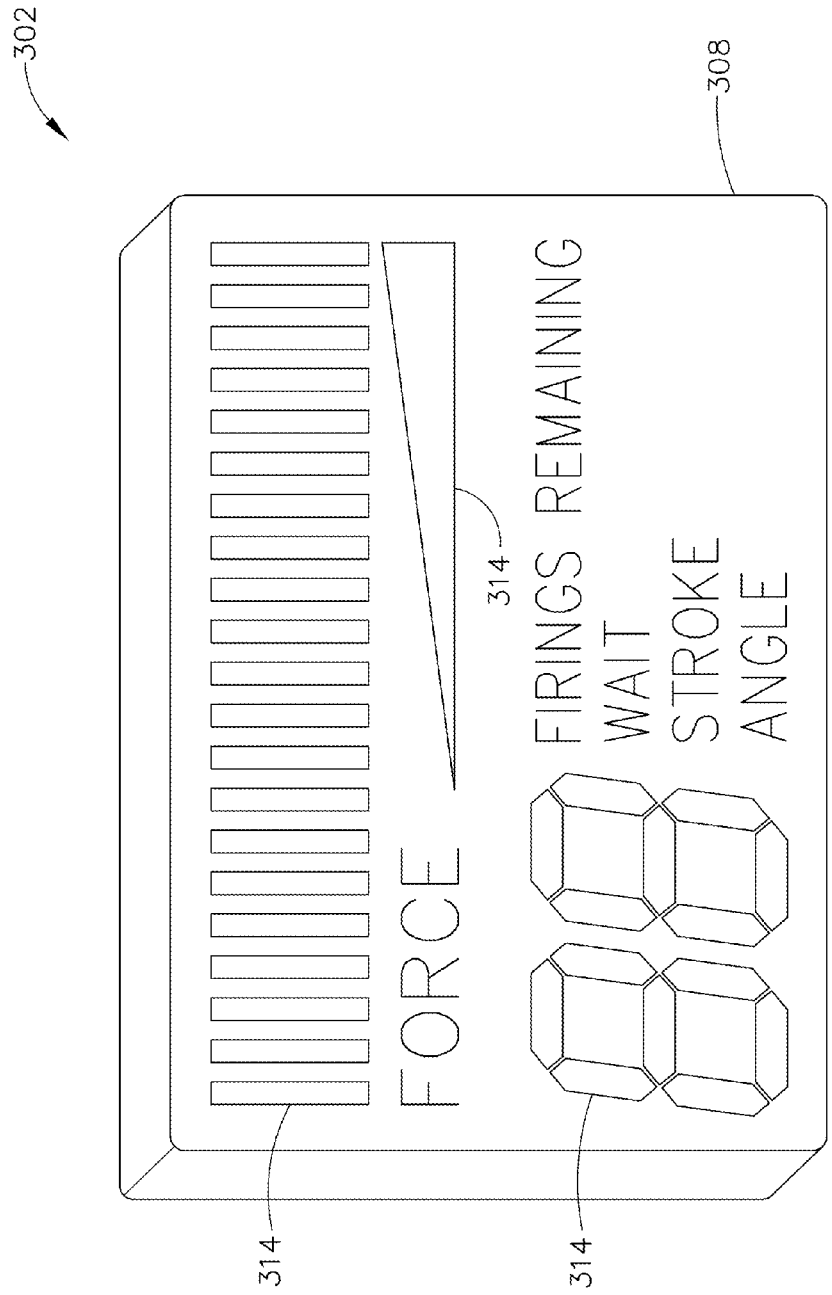

FIGS. 56-58 illustrate various embodiments of the status module 302. As shown, the status module 302 may comprise different types of indicators 314. According to various embodiments, the indicators 314 may comprise one or more visual indicators such as, for example, a light emitting diode, a multi-color light emitting diode, a display, etc. or any combination thereof. The display may comprise, for example, an alpha numeric display, a dot matrix display, a liquid crystal display, etc. According to various embodiments, at least one of the indicators 314 may comprise an audible indicator such as, for example, an audio output device. The audible output device may be embodied as, for example, a speaker, and may be in electrical communication with the switch 316. According to various embodiments, the indicators 314 may comprise at least one visual indicator and at least one audible indicator.

In operation, the indicators 314 may provide visual and audible feedback to a user of the surgical instrument 300. For example, as shown in FIG. 56, an indicator 314 (e.g., a light emitting diode) may be utilized to indicate whether the closure trigger 18 is in the locked position, whether a predetermined post-clamping wait period has been completed, whether a staple cartridge 34 is loaded, etc. Different indicators 314 may emit different colors of light. As used in FIGS. 56 and 57, different hatching indicates different colors. An indicator 314 (e.g., a multi-color light emitting diode) may be utilized for multiple status indications of a particular function of the surgical instrument 300. For example, to indicate the status of the staple cartridge 34, a multi-color light emitting diode may emit green light if a loaded staple cartridge 34 is in the channel 22, yellow light if a spent staple cartridge 34 is in the channel 22, or red light if a staple cartridge 34 is not in the channel 22. Similarly, to indicate the status of a cutting force being exerted by the surgical instrument 300, a multi-color light emitting diode may emit green light if the cutting force being exerted is in a normal range, yellow light if the cutting force being exerted is in an elevated range, or red light if the cutting force being exerted is in a high load range. It is understood that the indicators 314 may be utilized for multiple status indications of other functions of the surgical instrument 300 such as, for example, battery level.

As shown in FIG. 56, a line of indicators 314 (e.g., light emitting diodes) may be utilized to indicate the progression of the knife 32, the percentage of the maximum closure force being exerted, the percentage of the maximum firing force being exerted, the current articulation angle of the end effector 12, etc. Such indications may provide a user of the surgical instrument 300 with feedback concerning the forces involved in operating the surgical instrument 300 and feedback as to how close the surgical instrument 300 is operating to its maximum capacity. Although only one line of indicators 314 is shown in FIG. 56, it is understood that the status module 302 may comprise any number of lines of indicators 314.

As shown in FIG. 57, the status module 302 may comprise indicators 314 (e.g., light emitting diodes) arranged in two circular orientations. For such embodiments, the status module 302 may be capable of providing more concurrent information to a user of the surgical instrument 300 than the status module 302 shown in FIG. 56. Although two circular arrangements of indicators are shown in FIG. 57, it is understood that the status module 302 may comprise any number of indicators 314 arranged in any number of orientations. For example, the status module 302 may comprises indicators 314 arranged in a pyramid pattern.

As shown in FIG. 58, the indicators 314 of the status module 302 may comprise a line of light emitting diodes and at least one display (e.g., a liquid crystal display). For such embodiments, the status module 302 may be capable of providing more concurrent information to a user of the surgical instrument 300 than the status module 302 shown in FIG. 56 or FIG. 57. For example, the light emitting diodes may show reaction force at the anvil 24 and staple cartridge 22, the battery level, the articulation angle, etc. in the form of a bar graph. The display may show information concerning closure forces, firing forces, the number of firings remaining, post-clamping wait time, stroke progression, articulation angle, etc. in the form of digits. Various surgical instruments are disclosed in U.S. patent application Ser. No. 11/343,545, entitled SURGICAL INSTRUMENT HAVING A FEEDBACK SYSTEM, the entire disclosure of which is incorporated by reference herein.

Figure 60:
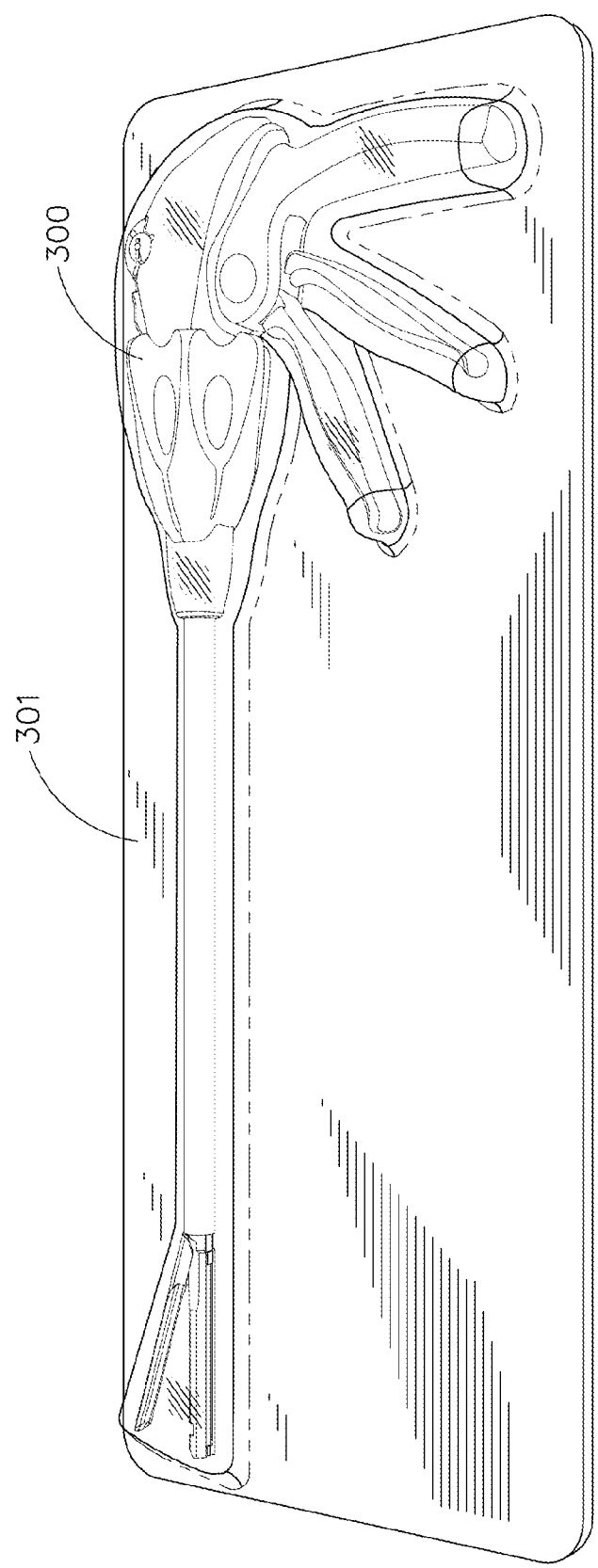
FIG. 60 is a view of a surgical instrument positioned within a sealed container.

In various embodiments, further to the above, a surgical instrument, such as surgical stapler 300, for example, may be sterilized before and/or after the surgical instrument is used. In at least one sterilization technique, referring to FIG. 60, a surgical instrument can be placed in a closed and sealed container, such as container 301, for example, wherein, in certain embodiments, the container can be comprised of plastic, such as high density polyethylene fibers, or TYVEK, for example, and can be in the shape of any suitable enclosure. The container and the instrument can then be placed in a field of radiation that can penetrate the container. In various circumstances, the radiation can comprise gamma radiation, x-rays, and/or high-energy electrons, for example, wherein the radiation can kill bacteria on the instrument 300 and in the container 301. The sealed, sterile container 301 can keep the instrument 300 sterile until it is opened in an operating room or some other suitable environment. In certain circumstances, however, when radiation, such as gamma radiation, for example, is used to sterilize the instrument 300, components of the surgical instrument 300, particularly electronic components such as memory devices and/or processors, for example, may be damaged by the radiation and may become defective or unstable. At least one such memory device can include memory device 2001, as described above, wherein, when memory device 2001 is exposed to radiation, at least some of the data contained within memory map 2300 may be lost and/or corrupted. In certain circumstances, a radiation sterilization process may even damage so-called "radiation hardened" electronics. In view of the above, alternative sterilization processes, such as ethylene oxide, hydrogen peroxide, and/or steam sterilization processes, for example, can be utilized to sterilize the entirety of instrument 300. In certain circumstances, however, such alternative sterilization processes may not be as preferable as radiation sterilization processes, at least with regard to sterilizing an end effector of a surgical instrument, for example.

In various embodiments, a surgical instrument can include first and second portions which can be operably engaged with and/or disengaged from one another. In at least one embodiment, further to the above, the first portion can comprise a handle portion and an end effector of a surgical stapler, such as handle 6 and end effector 12 of surgical stapler 300, for example, and the second portion can comprise a selectively attachable portion, such as status module 302, for example, wherein the first portion and the second portion can be sterilized separately. In certain embodiments, as a result, the handle portion and the end effector of the surgical stapler can be sterilized using a radiation sterilization process, for example, while the selectively attachable portion, which can comprise electronic components and/or any other radiation-sensitive components, can be sterilized using any other suitable sterilization process, such as steam and/or ethylene oxide sterilization processes, for example. In at least one such embodiment, as described in greater detail below, the first and second portions can be assembled together and/or operably engaged with one another after the first and second portions have been sterilized independently.

Figure 59:
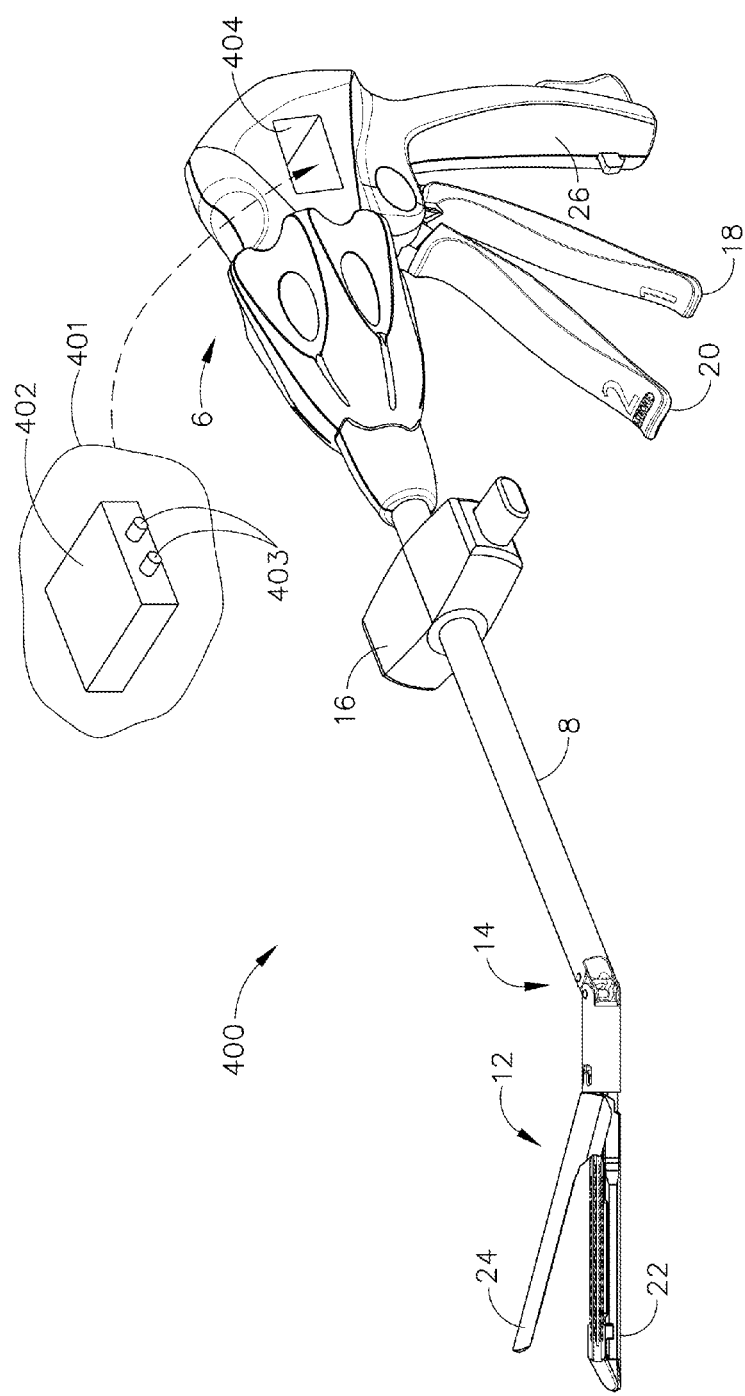
FIG. 59 is a perspective view of a surgical instrument according to various embodiments of the present invention.

In various embodiments, referring to FIG. 59, a surgical instrument can comprise a surgical instrument 400 and a selectively attachable module 402. In certain embodiments, surgical instrument 400 can include cavity 404 which can be configured to receive at least a portion of module 402. In at least one embodiment, module 402 can include one or more terminals or contacts 403 which can be configured to engage one or more terminals or contacts (not illustrated) of surgical instrument 400 in order to place module 402 in communication with surgical instrument 400. More particularly, the terminals or contacts of surgical instrument 400 and module 402 can be placed in communication with one another such that power, analog signals, and/or digital signals, for example, can be transmitted between surgical instrument 400 and module 402. Prior to assembling module 402 to surgical instrument 400, module 402 can be sterilized and then placed within a sterile container. In certain embodiments, module 402 can be sterilized while already placed within a container. In either event, further to the above, surgical instrument 400 can be removed from a sterile container, such as container 301, for example, after it has been sterilized by a gamma radiation process such that module 402 can be operably engaged with surgical instrument 400. In use, in at least one embodiment, module 402 can be removed from its sterile container, or bag, 401, and can be inserted into cavity 404 such that contacts or terminals 403 are in communication with the contacts or terminals of surgical instrument 400.

In various embodiments, further to the above, the first portion of a surgical instrument, such as the handle portion 6 and end effector 12 of surgical instrument 400, for example, can be removed from its sterile container, wherein at least a substantial portion of the second portion of the surgical instrument, such as module 402, for example, can remain in its sterile container. In at least one embodiment, bag 401, for example, can be punctured or incised such that terminals 403 of module 402 can at least partially extend through bag 401 and such that terminals 403 can be engaged with the terminals of surgical instrument 400. In certain embodiments, terminals 403 can be configured to puncture or incise bag 401. In at least one such embodiment, terminals 403 can be configured to puncture bag 401 when they are pressed against bag 401 with sufficient force. In some embodiments, bag 401 can include weakened portions or score marks, for example, which can be configured to allow bag 401 to tear along a predetermined path. In certain embodiments, terminals 403 can comprise male terminals and surgical instrument 400 can include female terminals, wherein the male terminals can be inserted into the female terminals in order to make electrical contact therebetween. In various embodiments, although not illustrated, a selectively attachable module can include one or more female terminals and a surgical instrument can include one or more male terminals which can be configured to puncture bag 401, for example, in order to be engaged with the female terminals of the module.

In any event, as a result of the above, a first portion, such as handle portion 6 and end effector 12 of surgical instrument 400, for example, and a second portion, such as module 402, for example, can undergo different sterilization processes and can be presented to an operating room, for example, in separately sterilized containers. Accordingly, a second portion having radiation-sensitive components can undergo a suitable non-radiation sterilization process and the first portion can undergo a radiation sterilization process without damaging the surgical instrument. In some circumstances, however, such non-radiation sterilization processes may not be able to completely or suitably sterilize the second portion of the surgical instrument. In such circumstances, bacteria or other contamination, for example, may be present within container, or bag, 401, for example, when it is presented to an operating room. In various embodiments, however, bag 401 and module 402 can be configured such that only a very small portion of bag 401 is perforated or incised when terminals 403 are pushed through bag 401, for example. In at least one such embodiment, the bacteria or other contamination contained within bag 401 may remain within, and may not escape from, bag 401 after it has been opened.

Further to the above, in certain embodiments, the container in which the second portion of the surgical instrument is stored can be configured to co-operate with the first portion of the surgical instrument such that the container and the first portion can limit or prevent the migration of bacteria and/or contaminants within the container, if present within the container, from migrating to the surgical site in the patient. In at least one embodiment, referring again to FIG. 59, bag 401 and module 402 can be configured such that, when they are inserted into cavity 404 of surgical instrument 400, bag 401 can sealingly engage, or at least substantially sealingly engage, the sidewalls of cavity 404. In an least one such embodiment, as a result, bacteria and/or contaminants may be prevented, or at least inhibited, from migrating from the interior of bag 401 to the exterior of surgical instrument 400. In various embodiments, module 402 and bag 401 can be inserted into cavity 404 prior to terminals 403 piercing bag 401 such that the holes within bag 401 are not created until terminals 403 are in contact with, or at least nearly in contact with, the terminals of surgical instrument 400. In at least one such embodiment, the puncture site can be protected such that bacteria or contamination inside sealed bag 401 would not be allowed to communicate with any patient contacting areas of surgical instrument 400. In certain embodiments, bag 401 and module 402 can be configured such that they can fit snugly within or be press-fit into cavity 403, for example. In at least some embodiments, although not illustrated, module 402 can include one or more attachment members or portions which can be configured to engage, and/or be engaged by, surgical instrument 400. In at least one embodiment, the attachment members can be configured to puncture bag 401, for example, while, in other embodiments, the attachment members can be configured to engage surgical instrument 400 without puncturing bag 401.

In various embodiments, a first portion of a surgical instrument can be delivered to an operating room, for example, in a first sealed container and a second portion of the surgical instrument can be delivered in a second sealed container, wherein the second portion can remain sealed within its sealed container when it is used with the first portion. In at least one embodiment, the first portion can comprise a handle portion and an end effector of a surgical stapler, for example, and the second portion can comprise a module which can be configured to communicate with the first portion wirelessly. In at least one such embodiment, the module can be contained within a sealed bag, such as bag 401, for example, wherein the module and the sealed bag can be inserted into a cavity, such as cavity 404, for example, within the surgical stapler. In various embodiments, the module can include a wireless signal transmitter and/or receiver and, in addition, the surgical instrument can also include a wireless signal transmitter and/or receiver such that the module and the surgical stapler can communicate via wireless transmissions, or signals. In at least one such embodiment, as a result, the bag or enclosure containing the module may not need to be perforated or incised in order for the module to perform its intended function, or functions, whether they may be displaying information, recording information from the surgical stapler, and/or transmitting information to the surgical stapler, for example. In at least one such embodiment, the module may include a power source which can be configured to supply the module with sufficient power to perform its intended functions. In certain embodiments, a power source can be contained within the second sealed container along with the module. In any event, very little power may be required to operate the module's wireless transmitter and/or receiver owing to the proximity of the module and the surgical stapler during use, especially when the module is at least partially positioned within the surgical stapler.

In certain other embodiments, the second portion of the surgical instrument, or module, may not be attached to or positioned within the first portion of the surgical stapler. In at least one such embodiment, the module can remain contained within its sealed container and can be positioned in any suitable location within the operating room, for example, such that the module can communicate directly with the first portion of the surgical instrument. In such embodiments, as a result, a module sterilized without radiation can be positioned a greater distance away from the patient as compared to various embodiments described above, thereby further reducing the possibility of bacteria or other contaminants migrating to the patient. In at least one embodiment, the module and the container can be positioned on or within a docking station. In certain embodiments, the docking station can include a wireless transmitter and/or receiver such that the module and/or the surgical instrument can communicate wirelessly with the docking station and such that the docking station can relay data or information between the module and the surgical stapler. In at least one embodiment, similar to the above, a second portion, or module, can include one or more terminals or contacts, such as terminals 403, for example, which can be configured to penetrate the container storing the module, such as bag 401, for example, in order to operably engage terminals or contacts of the docking station. In at least one such embodiment, the module can be directly engaged with the docking station, wherein the docking station can include a wireless transmitter and/or receiver which can be configured to wirelessly communicate with the first portion of the surgical instrument. Various surgical instruments are disclosed in U.S. patent application Ser. No. 11/651,771, entitled POST-STERILIZATION PROGRAMMING OF SURGICAL INSTRUMENTS, the entire disclosure of which is incorporated by reference herein.

In certain embodiments, a surgical instrument can comprise a first portion which can be sterilized by a first gamma radiation sterilization process and a second portion which can be sterilized by a second gamma radiation sterilization process. In at least one embodiment, the second gamma radiation sterilization process can have a lower intensity and/or a shorter duration of gamma radiation, for example, than the intensity and/or duration of gamma radiation, for example, of the first gamma radiation sterilization process. In at least one such embodiment, the second portion can include electronic components, such as memory devices or processors, for example, and/or any other radiation sensitive components, which can survive a lower intensity and/or shorter duration of radiation. In various embodiments, as a result, the first portion can be sterilized in a first sealed, sterile enclosure and the second portion can be independently, or separately, sterilized in a second sealed, sterile enclosure. In such embodiments, gamma radiation can be utilized to sterilize both the first and second portions, albeit to possibly different levels of sterilization. In any event, the first and second portions of the surgical instrument can be delivered to an operating room, for example, and can be assembled together, operably engaged, and/or otherwise suitably arranged with respect to each other.

In certain embodiments, a surgical instrument can comprise more than two portions which can be sterilized independently. In at least one embodiment, a surgical instrument can comprise a first portion which can be sterilized by a first sterilization process and delivered to an operating room, for example, in a first sealed, sterile container, a second portion which can be sterilized by a second sterilization process and delivered to the operating room in a second sealed, sterile container, and a third portion which can be sterilized by a third sterilization process and delivered to the operating room in a third sealed, sterile container. In at least one such embodiment, the first portion can comprise an end effector of a surgical instrument, such as end effector 12 of surgical instrument 300, for example, the second portion can comprise a handle, such as handle 6, for example, and the third portion can comprise a selectively attachable module, such as module 402, for example. In certain embodiments, further to the above, the first portion can be sterilized by a gamma radiation sterilization process, for example, the second portion can be sterilized by a gamma radiation sterilization process having a lower intensity and/or shorter duration than the first radiation sterilization process, for example, and the third portion can be sterilized by a non-radiation sterilization process, for example. In any event, one or more of the portions can remain sealed within, and/or only partially removed from, their enclosures when assembled to, operably engaged with, and/or otherwise suitably arranged with respect to the other portions of the surgical instrument.

In some instances, it may be desirable to operably engage and/or disengage a semi-sterile or unsterile power source, other components, and/or other electronic components with a surgical instrument for use during a surgical procedure. In one embodiment, the power source, the other components, and/or the other components can be removably positioned at least partially within a cavity defined in the surgical instrument. In various circumstances, the power source and/or the electronic components may be unsterilized, may be partially sterilized, and/or may comprise unsterilized or partially sterilized portions, for example, while the surgical instrument may be fully sterilized using a sterilization process, such as a gamma radiation sterilization process, for example. The surgical instrument can be fully sterilized while within a sealed container, such as container 301 described above. The sterilization process can be the same as described above. When used herein, the terms "sterile" or "sterilized" can mean treated through a sterilization process to a level sufficient for exposed use (i.e., open to an operating room and/or a patient) during a surgical procedure. The terms "unsterilized," "semi-sterilized," "non-sterile," "not sterile," "unsterile," and/or "partially sterilized" can mean not treated through a sterilization process, partially treated by a sterilization process, and/or treated by a sterilization process, but not to a level sufficient for exposed use during a surgical procedure.

Unsterile power sources and/or other electronic components, or portions thereof, in most cases, should be inhibited from exposure to a patient or an operating room during a surgical procedure to at least minimize contamination of the operating room and/or the patient during the surgical procedure caused by various bacteria, contamination, and/or microbes on the power sources and/or the other electronic components, for example. In various embodiments, the power sources can be configured to provide power to the surgical instrument and the electronic components can be configured to control and/or operate the surgical instrument, for example. In other various embodiments, the electronic components can be configured to record various tasks or operations performed by the surgical instrument. In one embodiment, the electronic components can comprise one or more electronic components. In other various embodiments, the electronic components can be optional and one or more of the power sources can be provided.

In various embodiments, a surgical instrument system can be configured to permit a non-sterile or semi-sterile portion, such as a power source or various electronic components, for example, of a surgical instrument to be at least partially inserted into and used with a sterile portion of the surgical instrument. In certain embodiments, the power source and/or the electronic components can be processed by a first sterilization treatment to a first degree of sterilization and the sterile portion can be processed by a second sterilization treatment to a second, greater degree of sterilization such that the second portion is sterile. In some instances, the first and second sterilization treatments can comprise the same, similar, or different sterilization methods.

Figure 61:
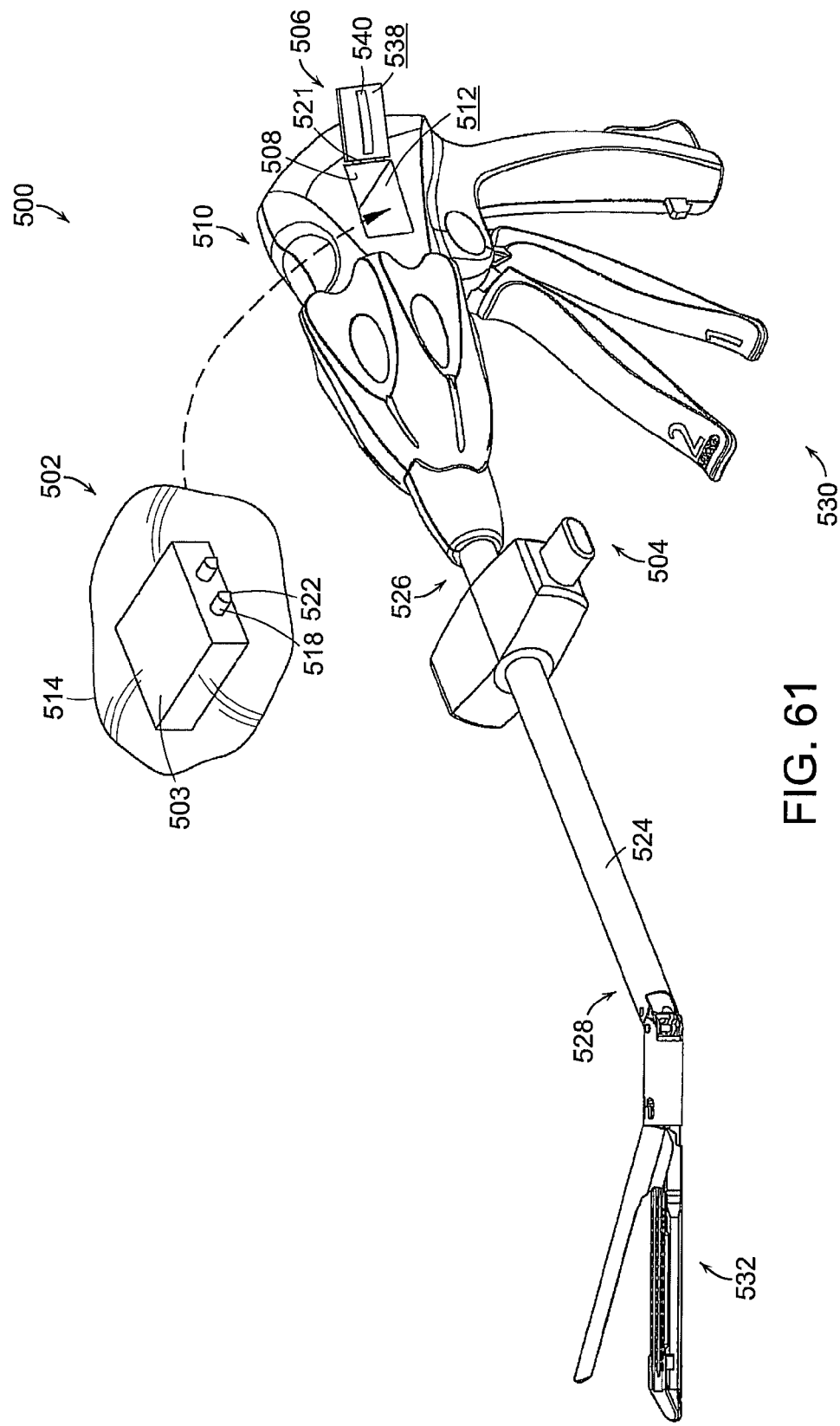
FIG. 61 is a perspective view of a surgical instrument comprising a first portion and a second portion according to various embodiments of the present invention.
Figure 62:
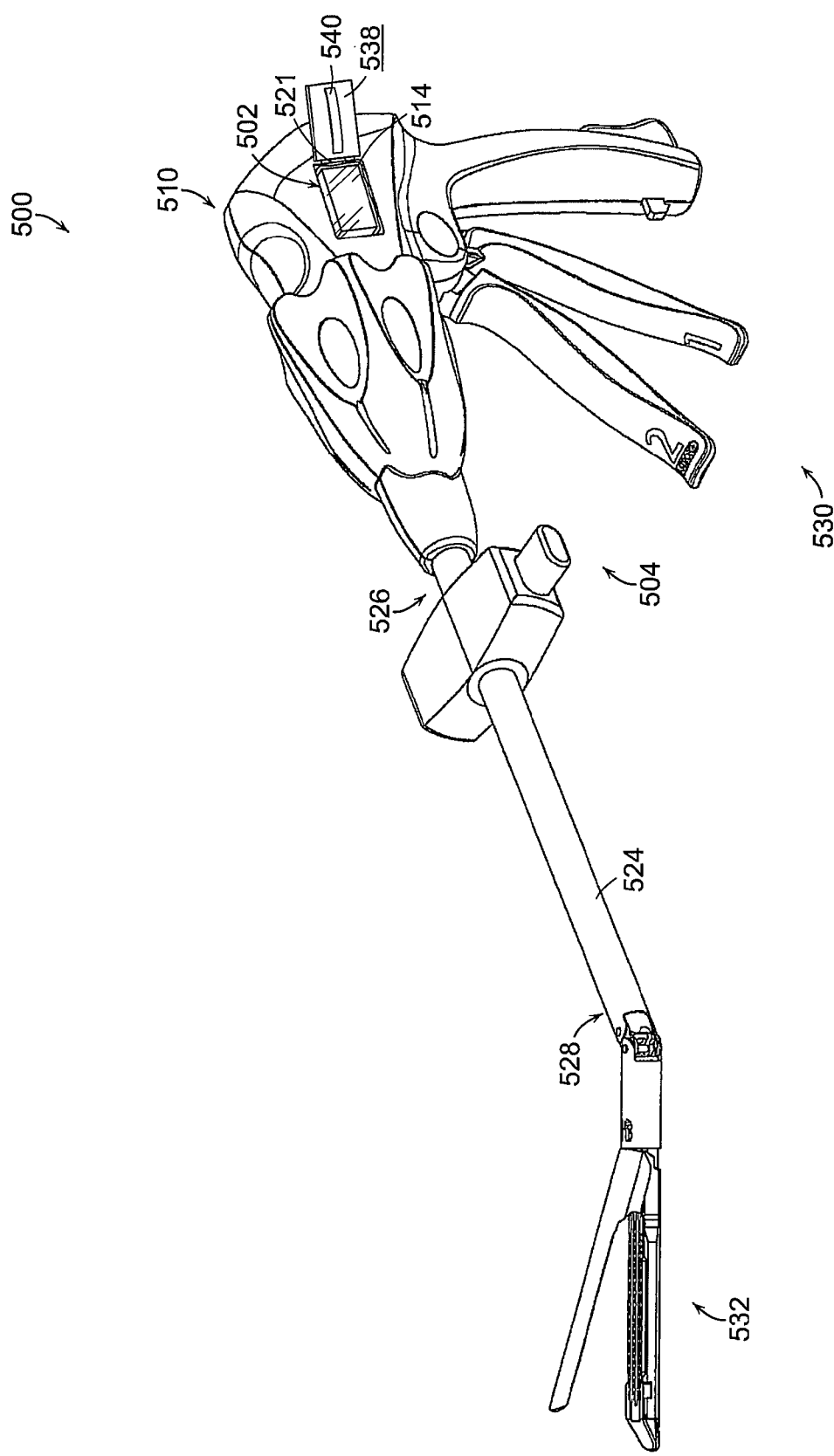
FIG. 62 is a perspective view of the surgical instrument of FIG. 61 where the first portion is at least partially positioned within a cavity defined in the second portion according to various embodiments of the present invention.

In one embodiment, referring to FIGS. 61 and 62, the surgical instrument system can comprise a surgical instrument 500 comprising a first portion 502 and a second portion 504. The surgical instrument 500 can comprise similar components as the surgical instruments 300 and 400 described above, but can also comprise a closure member 506 on or attached to the second portion 504. In various embodiments, the closure member 506 can be configured to be moved between a first position and a second position to cover a cavity 508 or a receiving slot defined in the second portion 504 of the surgical instrument 500. Prior to use, the second portion 504 can be packaged in a sealed container, such as container 301, for example, and sterilized as described above. In one embodiment, the second portion 504 can comprise a surgical instrument body 510 having a wall 512 defining the cavity 508 therein. The first portion 502 can comprise a power source, such as a battery, for example, and/or one or more electronic components, such as a controller chip, for example. The first portion 502 can be encapsulated by a membrane 514 or enclosed within a sealed package (also 514). In one embodiment, the membrane or sealed package 514 can comprise a microbe impermeable barrier layer. Although not illustrated, the first portion 502 can comprise a power source housed in a first membrane and various electronic components housed in a second membrane. Both the first membrane enclosing the power source and the second membrane enclosing the various electronic components can be positioned within the cavity 508 or can each be positioned in a separate cavity defined in the surgical instrument body 510, for example. By providing the surgical instrument systems described above, a non-sterile or semi-sterile first portion 502 can be selectively used with a sterile second portion 504 during a surgical procedure without contamination of the operating room, a patient-exposed surface of the second portion 504, and/or the patient. In other various embodiments, the first portion 502 can be sterile and still can be placed into the membrane 514 for additional precaution.

Figure 63:
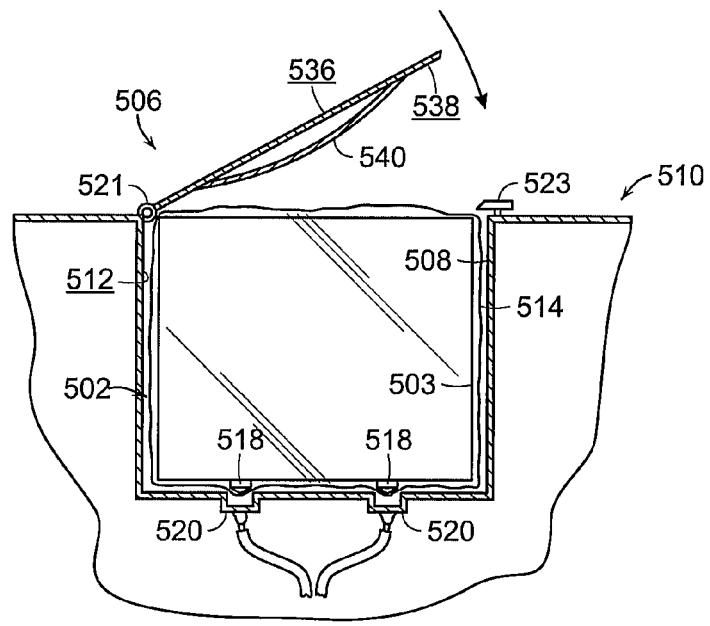
FIG. 63 is an illustration of a closure member of the surgical instrument of FIG. 62 positioned to engage the first portion and force the first portion into the cavity defined in the second portion.

In one embodiment, referring to FIGS. 61-63, the first portion 502 can comprise a power source 503, such as a power supply or source of electrical power, such as a device or system that supplies electrical energy to a load. In various embodiments, the power source 503 can be a battery comprising a single or a combination of multiple electrochemical Galvanic cells to store chemical energy. Multiple electrochemical Galvanic cells can be combined to deliver either higher voltage or higher current than with a single cell. In one embodiment, a battery can comprise non-rechargeable primary cells. Non-rechargeable batteries include alkaline batteries and alkaline cells that can utilize the reaction between zinc and manganese (IV) oxide (Zn/MnO2), zinc-carbon, zinc-chloride, and silver-oxide, among others. The Alkaline battery can comprise an alkaline electrolyte of potassium hydroxide. In one embodiment a battery can comprise rechargeable secondary cells. Rechargeable batteries can use electrochemical reactions that are electrically reversible and can come in many different sizes and use different combinations of chemicals. Commonly used secondary cell ("rechargeable battery") chemistries are lead acid, nickel cadmium (NiCd), nickel metal hydride (NiMH), lithium ion (Li-ion), and lithium ion polymer (Li-ion polymer). In other embodiments, the power source 503 can be a direct current (DC) power supply, alternating current (AC) power supply coupled to mains power or other general-purpose electric power supply at a frequency of 50 or 60 Hz, switched mode power supply. By way of example, a switched mode power supply can be classified into four types according to the input and output waveforms: (1) AC in, DC out: rectifier, off-line converter input stage; (2) DC in, DC out: voltage converter, or current converter, or DC to DC converter; (3) AC in, AC out: frequency changer, cycloconverter, transformer; or (4) DC in, AC out: inverter. In other embodiments, the first portion 502 can comprise a status module, such as status module 302 described above, for example.

Further to the above, in still other various embodiments, the first portion 502 can comprise other optional electronic components, such as a microprocessor, for example, configured to control and/or provide instructions to the surgical instrument 500. In various embodiments, such electronic components can comprise, or be implemented as, a computer system, a computer sub-system, a computer, a microprocessor, a controller, a microcontroller, an integrated circuit such as an application specific integrated circuit (ASIC), a programmable logic device (PLD), a processor such as general purpose processor, a digital signal processor (DSP), an interface, an input/output (I/O) device, a switch, a circuit, a logic gate, a register, a semiconductor device, a chip, a transistor, or any other device, machine, tool, equipment, component, or combination thereof. In one embodiment, the optional electronic components can be controlled by software, a software module, an application, a program, a subroutine, an instruction set, computing code, speech, symbols or combination thereof, according to a predefined computer language, manner or syntax, for instructing a processor to perform a certain function. Examples of a computer language can include C, C++, Java, BASIC, Perl, Matlab, Pascal, Visual BASIC, assembly language, machine code, micro-code for a network processor, and so forth. In yet other various embodiments, the first portion 502 can comprise other optional electronic components, such as a memory device, for example, configured to record various information and/or operations of the surgical instrument 500. In one embodiment, such electronic components can be engaged with the power source 503, positioned on or proximate to the power source 503, and/or positioned on or within a housing of the power source 503, for example.

Further to the above, in various embodiments, the first portion 502 can comprise one or more electrical terminals or contacts 518 which can be configured to electrically engage one or more electrical terminals or contacts 520 on the second portion 504. The terminals or contacts 520 can be positioned within the cavity 508 or positioned proximate to the cavity 508 such that they can be engaged with the terminals 518 when the first portion 502 is positioned within the cavity 508. In one embodiment, the terminals 520 can be positioned in one of the deepest portions of the cavity 508, relative to an outer surface of the surgical instrument body 510, such that any puncturing of the membrane 514 caused by the terminals 518 or 520 is proximate to one of the deepest portions of the cavity 508. When engaged with the cavity 508 of the second portion 504, the first portion 502 can be placed in communication with the second portion 504 such that power, analog, and/or digital signals, for example, can be transmitted between the first portion 502 and the second portion 504. In certain embodiments, the terminals 518 on the first portion 502 can comprise male terminals and the terminals 520 on the second portion 504 can comprise female terminals, wherein the male terminals 518 can be engaged with and/or inserted into the female terminals 520 in order to make electrical contact therebetween. The male terminals 518 of the first portion 502 can each comprise a puncturing tip 522 configured to puncture, pierce, or incise the membrane 514, for example, when pressed against the membrane 514 with sufficient force, in order to be engaged with the female terminals 520 of the second portion 504. The aperture or apertures created in the membrane 514 by the puncturing tip or tips 522 can be only slightly larger than the outer perimeter of the terminals 518 to at least inhibit contamination, bacteria, or microbes from within the membrane 514 from migrating out of the membrane 514. In some instances, sidewalls of the aperture or apertures in the membrane 514 can form a seal or sealing surface with the outer portions of the terminals 518, for example, to again at least inhibit contamination, bacteria, or microbes from within the membrane 514 from migrating out of the membrane 514. In various embodiments, although not illustrated, the first portion 502 can comprise one or more female terminals and the second portion 504 can comprises one or more male terminals, for example. In such an embodiment, the male terminals on the second portion 504 can puncture the membrane 514 and engage the female terminals on the first portion 502 when the first portion 502 is pushed toward the terminals on the second portion 504 with sufficient force.

In other various embodiments, the membrane 514 can comprise weakened portions, perforated portions, and/or score marks, for example, which can be configured to allow the membrane 514 to tear or separate along a predetermined path. In one embodiment, an entire portion of the membrane 514 positioned intermediate the terminals 518 and the terminals 520 can be perforated and/or can comprise score marks such that as the terminals 518 or a region of the first portion 502 is pushed against the membrane 514 with sufficient force, a portion of the membrane 514 can separate from the remainder of the membrane 514 and expose the first portion 502 comprising the terminals 518 or partially expose the first portion 502 comprising the terminals 518. In general, this may occur when the first portion 502 is positioned within the cavity 508 and when the cavity 508 is at least partially sealed from an external sterile environment.

In various embodiments, the first portion 502 can be fully or partially inserted into the cavity 508 prior to the terminals 518 piercing the membrane 514 such that apertures formed in the membrane 514 by the terminals 518 are not created until the terminals 518 are in contact with, or at least nearly in contact with, the terminals 520 of second portion 504 and the closure member 506 is at least mostly in the first position, thereby sealing the cavity 508 from a sterile outer surface of the second portion 504. When the terminals 518 and 520 are engaged with each other, they themselves can create a barrier to the migration of contamination, bacteria, and/or microbes from within the membrane 514, as their engagement can essentially form a press-seal between a part of the second portion 504 and a part of the first portion 502 thereby sandwiching a portion of the membrane 514 therebetween. In such an embodiment, the membrane 514 can act as a seal. As a result, the puncture site in the membrane 514 can be protected such that bacteria, microbes, and/or contamination inside the membrane 514 may not be allowed to communicate with any patient exposed areas or surfaces of the second portion 504.

In certain embodiments, although not illustrated, the second portion 504 can comprise one or more attachment members or portions which can be configured to engage, and/or be engaged by, the first portion 502. In one embodiment, the attachment members can be configured to puncture the membrane 514, for example, while, in other embodiments, the attachment members can be configured to engage the first portion 502 without puncturing membrane 514. Any other suitable form of engagement between the first portion 502 and the second portion 504 can also be used and is within the scope of the present disclosure.

In various embodiments, referring to FIGS. 61-63, the second portion 504 of the surgical instrument 500 can comprise a shaft 524 having a proximal end 526 and a distal end 528. A surgical instrument body 510 can extend from the proximal end 526 and can comprise a trigger portion 530 comprising a first trigger and a second trigger, for example. The trigger portion 530 can be operably engaged with an end-effector 532 extending from the distal end 528 of the shaft 524 such that it can be used to actuate the end-effector 532. In other embodiments, an actuation button or member (not illustrated) can be used in place of the trigger portion 530. In such an embodiment, the end-effector 532 can comprise at least one electrode configured to seal tissue, for example. In certain other embodiments, the end-effector 532 can comprise any suitable end-effector configured to perform a tissue sealing function, a tissue stapling function, a tissue cutting function, a tissue joining function, and/or any other suitable surgical function, for example. In one embodiment, the end-effector 532 can be attachable to or formed with the distal end 528 of the shaft 524, for example.

In various embodiments, still referring to FIGS. 61-63, the cavity 508 can be defined in the surgical instrument body 510 of the second portion 504. In certain embodiments, the wall 512 can define the bounds of the cavity 508 in the surgical instrument body 510. The cavity 508 can define any suitable shape configured for receiving the first portion 502. In one embodiment, the cavity 508 can comprise a first region comprising the one or more electrical terminals 520 and a second region comprising an opening or passage in the surgical instrument body 510 in communication with the cavity 508. The cavity 508 in the second portion 504 can be configured to at least partially or fully receive the first portion 502, while the first portion 502 is encapsulated and/or surrounded by the membrane or sealed package 514. An optional seal or a sealing surface (not illustrated) can be formed about, proximate to, around, or partially around the opening or passage of the second region of the cavity 508. Such a seal or sealing surface can be engaged with a portion of the closure member 506, or a seal or sealing surface on the closure member 506, for example, to create a microbe impermeable or at least partially microbe impermeable seal that can at least inhibit bacteria, microbes, and/or contamination on the first portion 502 or within the membrane 514 from migrating outside of the cavity 508 when the membrane 514 is punctured optionally by the terminals 518, for example.

In certain embodiments, referring again to FIGS. 61-63, the closure member 506 can be attached to, engaged with, or pivotably or rotatably attached to the second portion 504 proximate to the opening of the second region of the cavity 508. In one embodiment, the closure member 506 can be movable, slidable, rotatable, and/or pivotable between a first position in which the closure member 506 is in sealable engagement or sealable contact with the second region of the cavity 508 and a second position in which the closure member 506 is at least partially free from sealable engagement or sealable contact or free from sealable engagement or sealable contact with the second region of the cavity 508. In one embodiment, the first position can be a closed position in which the cavity 508 is at least partially or fully sealed from the outer surface of the surgical instrument body 510 and the second position can be an open position in which the cavity 508 is not fully sealed from the outer surface of the surgical instrument body 510. When in the first position, the closure member 506 can contact the seal or sealing surface of the second region of the cavity 508, for example.

Further to the above, in various embodiments, the closure member 506 can comprise a top surface 536, a bottom surface 538, and an optional seal or sealing surface (not illustrated). The optional seal or sealing surface can be positioned proximate to a perimeter of the bottom surface 538 and/or positioned proximate to, around, or at least partially around an outer perimeter of the closure member 506 which is configured to engage the second region of the cavity 508. The seal or sealing surface can be configured to create a microbe impermeable barrier or at least microbe resistant barrier between the cavity 508 and the sterile outer surface of the surgical instrument body 504, when engaged with the second region or a seal or a sealing surface on the second region of the cavity 508. Such a barrier can at least inhibit microbe contamination of the outer surface of the second portion 504 by the semi-sterile or non-sterile first portion 502.

In various embodiments, when the first portion 502 is positioned at least partially within the cavity 508, the bottom surface 538 of the closure member 506 can contact the first portion 502 and force the first portion 502 deeper into the cavity 508 when the closure member 506 is moved from the second position into the first position. In one embodiment, referring to the exemplary illustration of FIG. 63, the bottom surface 538 can comprise an optional camming surface 540 projecting therefrom. The camming surface 540 can be comprised of a resilient material and/or an inflexible material. In certain embodiments, the closure member 506 can comprise a spring, such as a cantilever spring and/or a leaf spring, for example, which can act upon and bias the camming surface 540. In one embodiment, the camming surface 540 can be configured to be engaged with the first portion 502 and force the first portion 502 deeper or further into the cavity 508 when the closure member 506 is moved from the second position into the first position. The camming surface 540 and/or the bottom surface 538 can transmit a force to the first portion 502 which, can cause the one or more terminals 518 (male) on the first portion 502 to puncture the membrane 514 and engage the one or more terminals 520 (female) on the second portion 504 when the closure member 506 is moved at least partially or fully into the first position. In other various embodiments, the camming surface 540 or the bottom surface 538 can transmit a force to the first portion 502 which can cause the one or more terminals (male) on the second portion 504 to puncture the membrane 514 and engage the one or more terminals (female) on the first portion 502 when the closure member 506 is moved at least partially or fully into the first position. In such an instance, the terminals 518 and 520 can be in electrical communication with each other when engaged. In various embodiments, the closure member 506 can be moved, slid, rotated, and/or pivoted, for example, between the first and second positions manually and/or automatically. In an embodiment in which the closure member 506 is pivoted or rotated, the closure member 506 can comprise or be attached to a hinge 521, for example. In various embodiments, the closure member 506 and/or the second portion 504 can comprise any suitable latching system 523 to hold the closure member 506 in the first position. The latching system 523 can also be used to help seal the first portion 502 within the cavity 508.

By providing for puncturing of the membrane 514 by the puncturing tips 522 of the terminals 518 when the closure member 506 is moved from the second position into the first position, any contamination, bacteria, and/or microbes that may be present on the first portion 502 and/or within the membrane 514 can be contained within the cavity 508 owing to the closure member 506. Stated another way, the membrane 514 may be punctured by the puncturing tips 522 when the first portion 502 is at least partially, and possibly fully, enclosed and sealed within the cavity 508 owing to the closure member 506 and the optional seals or sealing surfaces on the second region of the cavity 508 and/or the closure member 506. As a result, the semi-sterile or non-sterile first portion 502 can be used with the sterile second portion 504 while not contaminating the surgical site, the sterile outer surface of the second portion 504, and/or the patient.

In various embodiments, when the first portion 502, while encapsulated and/or sealed within the membrane 514, is at least partially positioned within the cavity 508, the membrane 514 and the wall 512 of the cavity 508 can be sealably engaged with each other, for example, owing to the snug fit of the first portion 502 within the cavity 508. Such a feature can aid in inhibiting any contamination, bacteria, and/or microbes from escaping from the cavity 508 after the puncturing tips 522 of the terminals 518 have punctured the membrane 514. Further, the puncturing of the membrane 514 can occur in one of the deepest portions of the cavity 508. As a result, any contamination exiting the membrane 514 can not only be maintained within the sealed cavity 508, but can also be maintained within a deep portion of the cavity 508 owing to the sealable engagement between the membrane 514 and the wall 512 of the cavity 508. Stated another way, the sealable engagement between the membrane 514 and the wall 512 can add an additional layer of protection of contamination escaping from the cavity 508.

In certain other embodiments, the closure member 506 can comprise a pushing screw (not illustrated) threaded through an aperture extending through the closure member 506. In such an embodiment, the closure member 506 can be moved into the first, closed position over the second region of the cavity 508 to at least mostly or fully seal the cavity 508 from the exterior environment and/or the second portion 504. An actuator or handle of the pushing screw can then be rotated, or otherwise actuated, to cause an end of the pushing screw distal from the handle to engage the first portion 502 and push the first portion 502 deeper or further into the cavity 508. In such an instance, the aperture in the closure member 506 and/or the portion of the pushing screw contacting sidewalls or threads of the aperture can comprise seals, sealing surfaces, or sealing materials to at least inhibit bacteria, microbes, and/or contamination within the cavity 508 from exiting the cavity 508 through the aperture and contaminating a surface of the sterile second portion 504. In such an embodiment, the membrane 514 can be punctured when the closure member 506 is in the fully closed position to maintain any contamination within the cavity 508.

In various embodiments, the closure member 506 can act in various stages upon the first portion 502 when the closure member 506 is moved between an open position and a closed position. In a first stage, the closure member 506 can be engaged with the first portion 502. In a second stage, the closure member 506 can begin to push the first portion 502 into the cavity 508 as the closure member 506 is moved toward the closed position. In a third stage, the closure member 506 can cause the terminals 518 (male) to engage the terminals 520 (female), for example. During this third stage, a seal about the opening or passage of the second region of the cavity 508 and/or a seal proximate to an outer perimeter of the closure member 506 can be engaged to begin to seal the cavity 508 from the exterior of the surgical instrument 500. In a fourth stage, the closure member 506 can cause the terminals 518 to puncture the membrane 514 and be placed in electrical communication with the terminals 520 as the closure member 506 is moved into the fully closed position. During this puncturing, the one or more appropriately positioned seals, as described herein, can be compressed as the closure member 506 is moved into the fully closed position thereby creating a suitable seal.

In other various embodiments, the first portion 502 may not comprise terminals having puncturing tips extending from the first portion 502 and may be able to communicate with and/or provide power to the second portion 504 wirelessly or through induction, respectively. As a result, in certain embodiments, the membrane 514 may not need to be punctured at all thereby maintaining any microbes, contamination, and/or bacteria within the membrane 514. In an embodiment where the first portion 502 communicates with the second portion 504 through induction, the first portion 502 can be positioned within the cavity 508 and contacts on the first portion 502 can be positioned proximate to contacts on the second portion 504 such that power can be transferred therebetween. In other embodiments where the first portion 502 transmits electrical signals to the second portion 504 wirelessly, the first portion 502 can be positioned at any suitable location within the operating room or location proximate to the operating room, for example. In such an embodiment, the first portion 502 and the second portion 504 can both comprise a wireless transmitter and a wireless receiver to accomplish such wireless communication therebetween. As a result, the non-sterile or semi-sterile first portion 502 can be positioned a distance away from the sterile second portion 504 and/or the patient thereby further reducing the chance that contamination, bacteria, and/or microbes on the first portion 502 and/or within the membrane 514 will contaminate the surgical site, the outer surface of the second portion 504, and/or the patient. Similar to that described above, the first portion 502 can also be positioned at a docking station, for example. When the first portion 502 is in wireless communication with the second portion 504, the cavity 508, in certain embodiments, can be eliminated, for example.

In various embodiments, the membrane 514 can be comprised of a gas permeable, microbe impermeable material or barrier layer such that any bacteria, microbes, and/or contamination on the first portion 502 can be maintained within the membrane 514. In certain embodiments, the membrane 514 can be comprised of a gas impermeable, microbe impermeable material, for example. Suitable membrane materials can comprise a polyethylene material, such as an antimicrobial coated TYVEK® material, for example. The antimicrobial coatings can comprise esters, lipids, and/or silver ions, for example, to provide the polyethylene material with antimicrobial properties. In one embodiment, a fluorocarbon agent, such as FC-808, a fluoro-aliphatic ester, can be used as the antimicrobial coating, for example.

In some instances, the first portion 502 can be positioned within the membrane 514 after the first portion 502 has been subjected to a sterilization treatment, such as a steam, ethylene oxide, ozone, and/or hydrogen peroxide sterilization treatment, for example. In other instances, the first portion 502 can be subjected to a sterilization treatment while sealed within or encapsulated by the membrane 514. In any event, the first portion 502 can be positioned within the membrane 514 and then the membrane 514 can be sealed using any suitable sealing methodologies, such as heat sealing, for example. As such, any bacteria, microbes, and/or contamination on the first portion 502 can be contained within the membrane 514 and may not be exposed to an operating room, the outer surface of the second portion 504, and/or a patient.

In operation, the surgical instrument system can allow the non-sterile or semi-sterile first portion 502 to be engaged with a sterile second portion 504 without contaminating an outer surface of the second portion 504. As such, the second portion 504 can be used within an operating room and exposed to a patient while containing the non-sterile or semi-sterile first portion 502. In one embodiment, the first portion 502 can be positioned and sealed within the membrane 514 outside of a surgical site (i.e., a sterile environment, sometimes an operating room). The first portion 502, while sealed within the membrane 514, can then be taken into the surgical site. The second portion 504 can also be taken into the surgical site within a sterile container, such as container 301, for example. Next, the second portion 504 can be removed from the sterile container and the first portion 502, while still within the membrane 514, and then positioned within the cavity 508 defined in the surgical instrument body 510 of the second portion 504. In some instances, the first portion 502 can fit snugly within and/or be press-fit within the cavity 508 wherein the membrane 514 can sealably engage the wall 512 of the cavity 508 to create a seal or a sealable engagement between the membrane 514 and the wall 512. The closure member 506 can be moved from the second, at least partially open position into the first, closed position. As the closure member 506 is moved from the second position into the first position, the bottom surface 538 of the closure member 506 or the optional camming surface 540 can act against the first portion 502 to push the first portion 502 further into the cavity 508 and cause the terminals 518 or 520 to puncture the membrane 514 and create an electrical connection between the first portion 502 and the second portion 504, for example. A surgeon can then use the surgical instrument system for a surgical procedure while the first portion 502 is contained within the cavity 508 of the second portion 504.

After the surgical procedure, the surgical instrument system can be removed from the surgical site, the closure member 506 can be moved from the first position into the second position, and the first portion 502 can be removed from the second portion 504. The first portion 504 can then be removed from the remaining membrane 514 and the remaining membrane 514 can be discarded. In various embodiments, the first portion 502 can optionally be reconditioned, sterilized, or partially sterilized and then be positioned within a new membrane 514 and prepared for use with another sterile second portion 504. In other various embodiments, the first portion 502 can be positioned within the new membrane 514 without being treated or sterilized at all. As a result, the first portion 502, although generally not sterile, can be reused in multiple surgical procedures without the need for prior or subsequent sterilization or at least sterilization to the level of the second sterile portion 504.

In various embodiments, it may be desirable to provide electronic components, such as power sources, controller chips, programming chips, microcontrollers, microprocessors, status modules, and/or other various electronic components, for example, which are coated with antimicrobial or microbe resistant materials or provided in a housing comprising antimicrobial or microbe resistant materials. As such, these various electronic components may not need to be sterilized using conventional sterilization techniques, such as gamma radiation sterilization techniques, for example. In various embodiments, the materials of the housings and the coatings can actually prevent, kill, or at least inhibit contamination by bacterial or microbes, for example. As these electronic components are generally attachable to or engagable with sterile surgical instruments or portions thereof to control and/or provide power to the surgical instruments, for example, it can be desirable that they do not contaminate the sterile surgical instruments. In one embodiment, the electronic components within the housing or coated with the antimicrobial or microbe resistant materials can be positioned within the membrane 514 described above, for example.

In one embodiment, one or more electronic components can be positioned or encapsulated within a housing comprised of an antimicrobial material or a microbe resistant material, such as silver or antimicrobial lipids, for example. In other embodiments, the housing can comprise an outer surface comprised of the antimicrobial material or the microbe resistant material. In certain other embodiments, the electronic components can be coated with an antimicrobial coating or a microbe resistant coating. In any event, the electronic components can be bathed in antimicrobial soap solutions and/or other antimicrobial solutions prior to being positioned within the housing or prior to being coated to reduce the amount of contamination, bacteria, and/or microbes present on the electronic components. In various embodiments, one or more electrical contacts or terminals that extend from or are positioned on the electronic components can be comprised of conductive antimicrobial materials or conductive microbe resistant materials and/or can be coated with conductive antimicrobial materials or conductive microbe resistant materials. Silver can be one example of such conductive materials.

In an embodiment in which a housing is provided around the electronic components, one or more vents can be provided in the housing to allow for cooling of the electronic components during their operation. The vents can be covered with materials which are gas permeable and microbe impermeable, such as polyethylene materials like TYVEK®, for example, to allow a gas, such as air, for example, to flow into and out of the housing and cool the electronic components, but prevent, or at least inhibit, any microbes, bacteria, and/or contamination on the electronic components or within the housing from exiting the housing. In one embodiment, the material covering the vents can comprise antimicrobial coatings. These antimicrobial coatings can comprise esters, lipids, and/or silver ions, for example, to provide the material covering the vents with antimicrobial properties. In one embodiment, a fluorocarbon agent, such as FC-808, a fluoroaliphatic ester, can be used as the antimicrobial coating, for example. In certain embodiments, the housing or the electronic components themselves can comprise fins or heat sinks configured to dissipate heat away from the electronic components. These fins or heat sinks can be comprised of or coated with thermally conductive antimicrobial or microbe resistant materials.

Figure 64:
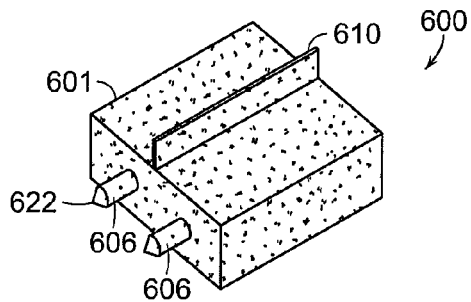
FIG. 64 is a perspective view of a power source according to various embodiments of the present invention.
Figure 65:
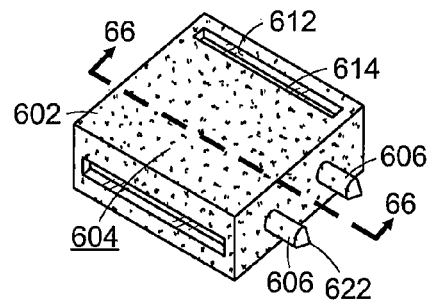
FIG. 65 is a perspective view of another power source according to various embodiments of the present invention.

In various embodiments, one or more electronic components, such as a controller chip, for example, can be coupled to another electronic component, such as a power source, for example. In one embodiment, the electronic components can be attached to the power source, formed with the power source, positioned within the housing with the power source, and/or otherwise combined with the power source. In various embodiments, a power source may not be provided and only the electronic components may be positioned within the housing and/or coated with the antimicrobial or microbe resistant materials. FIGS. 64 and 65 illustrate an exemplary electronic component, such as a power source, for example. Those of skill in the art will understand that the present disclosure is not so limited.

Figure 66:
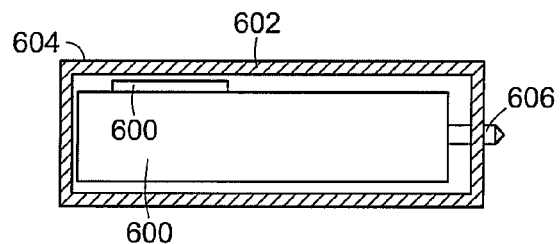
FIG. 66 is a cross-sectional view of the power source of FIG. 65 taken along line 66-66 in FIG. 65 according to various embodiments of the present invention.

In one embodiment, referring to FIGS. 64-66, one or more electronic components 600, such as a power source, a chip for a programmable controller, and/or a programmable controller, for example, can have an antimicrobial coating or a microbe resistant coating 601 thereon (see e.g., FIG. 64) and/or can be surrounded by a housing 602 comprising an outer surface 604 comprised of or partially comprised of an antimicrobial material or a microbe resistant material (see e.g., FIGS. 65 and 66). In various embodiments, some exemplary antimicrobial materials or microbe resistant materials can comprise plastics imbedded with silver ions, plastics or metals comprising nano-structures that repel or kill bacteria, such as shark skin and nano-carbon tubes, for example, and/or materials comprising titanium oxide micro-channels configured to have a trickling electrical current flowing through them from the power source. Shark skin, for example, can prevent, or at least inhibit, bacteria, microbes, and/or other contamination from attaching to its surface. Other nano-structure materials can act like daggers to pierce unwanted cells (i.e., bacterial, microbes, and/or other contamination) to kill the cells and/or break up the cells' viral material. In one embodiment, by using a trickle charge from a power source, the outer housing 602 can be slightly electrified or charged to kill bacteria, microbes, and/or other contamination present thereon. Some antimicrobial or microbe resistant coatings can comprise iodine, antibiotics, such as penicillin, for example, antimicrobial lipids, and/or silver ion coatings, for example. Of course, those of skill in the art will recognize that any other suitable antimicrobial or microbe resistant materials or coatings can be used to comprise a portion of the housing 602 or can be used as a coating on the electronic components 600 or the housing 602.

In various embodiments, referring again to FIGS. 64 and 65, the electronic components 600 can comprise one or more electrical contacts or terminals 606. The one or more electrical terminals 606 can be engaged with one or more electrical contacts or terminals (not illustrated) of a surgical instrument such that the electronic components 600 can communicate with the surgical instrument via digital signals, analog signals, and/or electrical signals, for example. The electrical terminals 606 can be coated with or formed of an antimicrobial material or a microbe resistive material such that the electrical terminals 606 are at least partially resistant to contamination by microbes or bacteria. If the electrical terminals 606 extend from the housing 602, a seal (not illustrated) can be positioned where the electrical terminals 606 extend through the housing 602 to at least inhibit microbes, bacteria, and/or contamination from the electric components 600 from exiting the housing 602. The antimicrobial materials or a microbe resistive materials of the electrical terminals 606 may generally be conductive or at least have conductive portions, such that the electrical terminals 606 can conduct electricity or electrical signals. In various embodiments, the electrical terminals 606 can have puncturing tips 622, like the puncturing tips 522 described above, which can be configured to puncture a membrane or sealed package, like the membrane 514 described above, for example.

In various embodiments, heat dissipating devices or structures can be positioned on the housing 602, attached to the housing 602, integrally formed with the housing 602, formed with the electronic components 600, attached to the electronic components 600, and/or in thermal contact with the electronic components 600 and/or the housing 602, for example. In one example embodiment, referring to FIG. 64, a fin or heat sink 610 is illustrated extending from the electronic component 600. The fin or heat sink 610 can be comprised of a highly thermally conductive antimicrobial material or the microbe resistant material, such as silver, for example, and/or can be coated with an antimicrobial material or the microbe resistant material. In other embodiments, the fin or heat sink 610 can be comprised of aluminum and/or stainless steel, for example, wherein the aluminum and/or stainless steel can be coated with an antimicrobial material or a microbe resistant material, such as silver, for example. In an embodiment where a coating is applied to the fin or heat sink 610, the fin or heat sink 610 can be comprised of a highly thermally conductive material to aid in the dissipation of heat from the electronic components 600. The antimicrobial materials, the microbe resistant materials, the antimicrobial coatings, and the microbe resistant coatings can be the same as described above, for example. In one embodiment, the fin or heat sink 610 can comprise a different antimicrobial material, microbe resistant material, antimicrobial coating, and/or microbe resistant coating than the antimicrobial material, microbe resistant material, antimicrobial coating, and/or microbe resistant coating of the housing 602. For example, the heat sink or fin 610 could be comprised of a material which has better heat transferring properties than the material of the housing 602 or coating on the electronic component 600.

In various embodiments, referring to FIG. 65, one or more vents, such as vents 612, for example, can be defined in the housing 602. The vents 612 can allow a gas, such as air, for example, to flow into and out of the housing 602 such that the one or more electronic components 600 within the housing 602 can be cooled during operation or activation of the electronic components 600. In one embodiment, the vents 612 can be covered with a microbe impermeable, gas permeable barrier layer 614 configured to allow a gas to pass therethrough, but configured to prevent or at least inhibit the passage of microbes from within the housing 602 through the vents 612. The vents 612 can be used on the housing 602 either in addition to or in lieu of the fins or heat sinks 610 described above. In various embodiments, FIG. 66 illustrates a cross-sectional view taken along line 66-66 of FIG. 65. In such an embodiment, the housing 602 is illustrated surrounding two electronic components, each labeled 600, such as a power source and a controller chip, for example. As a result, it is illustrated how any contamination, bacteria, and/or microbes present on the electronic components 600 can be contained within the housing 602 owing to the sealed nature of the housing 602.

While the present disclosure has been illustrated by description of several embodiments and while the illustrative embodiments have been described in considerable detail, it is not the intention of the applicants to restrict or in any way limit the scope of the appended claims to such detail. Additional advantages and modifications may be readily apparent to those skilled in the art. Furthermore, although the embodiments disclosed herein have been described in connection with a surgical instrument, other embodiments are envisioned in connection with any suitable medical device. While this disclosure has been described as having exemplary designs, the disclosure may be further modified within the spirit and scope of the disclosure. This application is therefore intended to cover any variations, uses, or adaptations of the disclosure using its general principles. Further, this disclosure is intended to cover such departures from the present disclosure as come within known or customary practice in the art to which this disclosure pertains.

Further to the above, the various embodiments of the present disclosure have been described above in connection with cutting-type surgical instruments. It should be noted, however, that in other embodiments, the sterilized surgical instrument disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc. In certain embodiments, an ultrasonic instrument can be sterilized and utilized in accordance with the embodiments disclosed herein. In at least one such embodiment, an ultrasonic instrument can include a first portion comprising a handle and/or end effector, for example, and a second portion comprising radiation-sensitive electronics which can be sterilized independently from the first portion. Various ultrasonic instruments are disclosed in U.S. Pat. No. 6,063,098, entitled ARTICULATABLE ULTRASONIC SURGICAL APPARATUS, which issued on May 16, 2000, the entire disclosure of which is incorporated by reference herein. Although the present disclosure has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Further to the above, the various staple cartridges disclosed herein can be disposable. In at least one embodiment, an expended staple cartridge, or an at least partially expended staple cartridge, can be removed from a surgical stapler and replaced with another staple cartridge. In other various embodiments, the staple cartridge may not be removable and/or replaceable during the ordinary use of the surgical instrument but, in some circumstances, may be replaceable while and/or after the surgical stapler is reconditioned as described in greater detail below. In various embodiments, the staple cartridge can be part of a disposable loading unit or end-effector which can further include a staple cartridge carrier, anvil, cutting member, and/or staple driver. In at least one such embodiment, the entire, or at least a portion of, the disposable loading unit or end-effector can be detachably connected to a surgical instrument and can be configured to be replaced.

The devices disclosed herein can be designed to be disposed of after a single use, or they can be designed to be used multiple times. In either case, however, the devices can be reconditioned for reuse after at least one use. Reconditioning can include any combination of the steps of disassembly of the device, followed by cleaning or replacement of particular pieces, and subsequent reassembly. In particular, the devices can be disassembled, and any number of the particular pieces or parts of the devices can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present disclosure.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

What is claimed is:
1. A surgical instrument comprising:
a first portion comprising at least one first electrical contact;
a membrane encapsulating the first portion; and
a second portion, comprising:
 a shaft having a proximal end and a distal end;
 a surgical instrument body extending from the proximal end;
 an end-effector extending from the distal end;
 a wall defining a cavity in the surgical instrument body, wherein the cavity is configured to at least partially receive the first portion while the first portion remains encapsulated by the membrane;
 a first region comprising at least one second electrical contact;
 a second region comprising an opening in communication with the cavity; and
 a closure member movable between a first position and a second position, wherein the closure member is in sealable engagement with the second region when it is in the first position, wherein the closure member is at least partially free from sealable engagement with the second region when it is in the second position, and wherein one of the first electrical contact and the second electrical contact is configured to penetrate the membrane to make an electrical connection between the first portion and the second portion when the closure member moves from the second position into the first position.

2. The surgical instrument of claim 1, wherein the first portion comprises a non-sterile portion, and wherein the second portion comprises a sterile portion.

3. The surgical instrument of claim 1, wherein the closure member is pivotably attached to the second portion, and wherein the closure member is pivotable between the first position and the second position.

4. The surgical instrument of claim 1, wherein the closure member comprises:
   an outer perimeter;
   a seal positioned one of around and proximate to the outer perimeter, wherein the seal is configured to be engaged with the second region when the closure member is in the first position and create a microbe impermeable barrier between the cavity and an outer surface of the second portion to at least inhibit microbe contamination of the outer surface of the second portion by the first portion.

5. The surgical instrument of claim 1, wherein the second portion comprises a seal positioned one of around and proximate to the opening.

6. The surgical instrument of claim 1, wherein the closure member comprises:
   a camming surface configured to push the first portion into the cavity when the closure member is moved from the second position into the first position.

7. The surgical instrument of claim 1, wherein the first portion comprises a power source.

8. The surgical instrument of claim 1, wherein the first portion comprises electronic components configured to operate the second portion.

9. A surgical instrument system comprising:
   a first portion comprising a non-sterile portion comprising at least one first electrical terminal;
   a sealed package, wherein the first portion is positioned within the sealed package, and wherein the sealed packages comprises a microbe impermeable barrier layer; and
   a second portion comprising a sterile portion comprising:
      a surgical instrument body;
      a receiving slot defined in the surgical instrument body, wherein the receiving slot is configured to receive at least part of the first portion while the first portion is positioned within the sealed package;
      a first region comprising at least one second electrical terminal;
      a second region defining a passage into the receiving slot; and
      a closure member movable between a first position and a second position, wherein the closure member is in sealable contact with the second region when it is in the first position, wherein the closure member is at least partially free from sealable contact with the second region when it is in the second position, and wherein the closure member comprises a camming surface configured to force the first portion into the receiving slot and configured to cause one of the first electrical terminal and the second electrical terminal to pierce the sealed package to make an electrical connection between the first portion and the second portion when the closure member moves from the second position into the first position.

10. The surgical instrument system of claim 9, wherein the first portion comprises at least one of a power source configured to provide power to the second portion and electronic components configured to control an operation of the second portion.

* * * * *